(12) United States Patent
Larsen et al.

(10) Patent No.: US 9,107,440 B2
(45) Date of Patent: Aug. 18, 2015

(54) POLYPEPTIDES HAVING TRANSGALACTOSYLATING ACTIVITY

(75) Inventors: Morten Krog Larsen, Sabro (DK); Charlotte Horsmans Poulsen, Brabrand (DK)

(73) Assignee: DuPont Nutrition Biosciences ApS, Copenhagen (DK)

( * ) Notice: Subject to any disclaimer, the term of this patent is extended or adjusted under 35 U.S.C. 154(b) by 246 days.

(21) Appl. No.: 13/637,907

(22) PCT Filed: Mar. 29, 2011

(86) PCT No.: PCT/EP2011/054865
§ 371 (c)(1),
(2), (4) Date: Sep. 27, 2012

(87) PCT Pub. No.: WO2011/120993
PCT Pub. Date: Oct. 6, 2011

(65) Prior Publication Data
US 2013/0059034 A1 Mar. 7, 2013

Related U.S. Application Data

(60) Provisional application No. 61/318,580, filed on Mar. 29, 2010.

(30) Foreign Application Priority Data

Mar. 29, 2010 (EP) .................................. 10158172

(51) Int. Cl.
*A23C 9/00* (2006.01)
*A23L 1/305* (2006.01)
*A23C 9/12* (2006.01)
*A23C 19/032* (2006.01)
*A23C 19/05* (2006.01)
*A23G 9/36* (2006.01)

(52) U.S. Cl.
CPC .............. *A23L 1/3053* (2013.01); *A23C 9/1216* (2013.01); *A23C 19/0328* (2013.01); *A23C 19/054* (2013.01); *A23G 9/36* (2013.01); *C12Y 204/01* (2013.01); *A23V 2002/00* (2013.01)

(58) Field of Classification Search
CPC ........................................................ A23C 9/00
USPC .............................................. 435/42, 43, 522
See application file for complete search history.

(56) References Cited

U.S. PATENT DOCUMENTS

2010/0080866 A1* 4/2010 Araki et al. ..................... 426/43

FOREIGN PATENT DOCUMENTS

| EP | 0323201 A2 | 7/1989 |
|---|---|---|
| WO | 0190317 A2 | 11/2001 |
| WO | 2009071539 A1 | 6/2009 |

OTHER PUBLICATIONS

Weinstock et al., UniProt Database, Accession No. C9LAL1, Nov. 2009.*
Database UniProt [Online] SubName: "Full=Beta-Galactosidase;", XP002591904, retrieved from EBI accession No. UNIPROT:C9LAL1, Database accession No. C9LAL1 the whole document. (Nov. 24, 2009).
Database Geneseq [Online] "*Bifidobacterium bifidum* Beta-Galactosidase OLGA5 protein.", XP002591905, retrieved from EBI accession No. GSP:ABB05030, Database accession No. ABB05030 the whole document. (Mar. 22, 2002).
Database Geneseq [Online] "*B. bifidum* Lactase/Beta-Galactosidase Fragment (residues 28/1331).", XP002591906, retrieved from EBI accession No. GSP:AWY98338, Database accession No. AWY98338 compound & WO 29009/071539 A1 (nOVOZYMES AS[DK]; CHR Hansen AS [DK]; Henriksen Hanne Vang [DK]; ERNS) Jun. 11, 2009 claims 1-13.
Database UniProt [Online] "SubName: Full=Putative Uncharacterized Protein;", XP002610554, retrieved from EBI accession No. UNIPROT:B5CQV4, Database accession No. B5GQV4 the whole document. (Oct. 14, 2008).
Database UniProt [Online] "SubName: Full=Putative Uncharacterized Protein;", XP002654124, retrieved from EBI accession No. UNIPROT:COBEY6 Database accession No. DOBEY6 the whole document. (May 5, 2009).
Dumortier V et al: "Purification and Properties of a Beta-Galactosidase from *Bifidobacterium bifidum* Exhibiting a Transgalactosylation Reaction", Biotechnology and Applied Biochemistry, Academic Press, US, vol. 19, No. 19, (Jan. 1, 1994), pp. 341-354, XP002902258, ISSN: 0885-4513 abstract.
Martinez-Villaluenga et al: "Optimization of Conditions for Galactooligosaccharide Synthesis During Lactose Hydrolysis by Beta-Galactosidase from *Kluyveromyces lactis* (Lactozym 3000 L HP G)", Food Chemistry, Elsevier Ltd, NL LNKD-DOI:10,1016/J. Foodchem.2007-08-011, vol. 107, No. 1, (Oct. 30, 2007), pp. 258-264, XP022322353, ISSN: 0308-8146 abstract.
Jorgensen F et al: "High-Efficiency Synthesis of Oligosaccharides with a truncated beta-galactosidase from *Bifidobacterium bifidum*", Applied Microbiology and Biotechnology, Springer Verlag, Berlin, DE, vol. 57, No. 5-6, (Dec. 1, 2001), pp. 647-652, XP009136121, ISSN: 0175-7598 abstract.
Martinez-Villaluenga et al, "Optimization of Conditions for Galactooligosaccharide Synthesis During Lactose Hydrolysis by Beta-Galactosidase from *Kluyveromyces lactis* (Lactozym 3000 L HP G)", Food Chemistry 107 (2008) 258-264.
European Office Action dated Jul. 4, 2014 in European Application No. 11713215.9, pp. 1-7.

* cited by examiner

*Primary Examiner* — Maryam Monshipouri
(74) *Attorney, Agent, or Firm* — Shook, Hardy & Bacon L.L.P.

(57) ABSTRACT

The present invention relates to polypeptides, specifically polypeptides having transgalactosylating activity and nucleic acids encoding these, and their uses in e.g. dairy product.

3 Claims, 4 Drawing Sheets

POLYPEPTIDES HAVING TRANSGALACTOSYLATING ACTIVITY

CROSS-REFERENCE TO RELATED APPLICATIONS

This application claims priority to PCT Application No. PCT/IB2011/054865 entitled "Polypeptides Having Transgalactosylating Activity," filed Mar. 29, 2011, which claims priority to U.S. Provisional Application No. 61/318,580, filed Mar. 29, 2010 and EP No. 10158172.6, filed Mar. 29, 2010, all of which are expressly incorporated by reference herein in their entirety.

SEQUENCE LISTING

A text file in compliance with ASCII and having a ".txt" extension has been electronically submitted via EFS-Web. The text file named "Sequence Listing" was created on Nov. 7, 2012 and is 87,924 bytes. The text file is expressly incorporated by reference herein in its entirety.

FIELD OF THE INVENTION

The present invention relates to polypeptides, specifically polypeptides having transgalactosylating activity and nucleic acids encoding these, and their uses in e.g. dairy product.

BACKGROUND OF THE INVENTION

Galactooligosaccharides (GOS) are carbohydrates which are nondigestable in humans and animals comprising two or more galactose molecules, typically up to nine, linked by glycosidic bonds. GOS's may also include one or more glucose molecules. One of the beneficial effects of GOS's is their ability of acting as prebiotic compounds by selectively stimulating the proliferation of beneficial colonic microorganisms such as bacteria to give physlologicai benefits to the consumer. The established health effects have resulted in a growing interest In GOSs as food ingredients for various types of food.

The enzyme β-galactosidase (EC 3.2.1.23) usually hydrolyses lactose to the monosaccharides D-glucose and D-galactose. In the normal enzyme reaction of β-galactosidases, the enzyme hydrolyses lactose and transiently binds the galactose monosaccharide in a galactose-enzyme complex that transfers galactose to the hydroxyl group of water, resulting in the liberation of D-galactose and D-glucose. However, at high lactose concentrations some β-galactosidases are able to transfer galactose to the hydroxyl groups of D-galactose or D-glucose in a process called transgalactosylation whereby galacto-oligosaccharides are produced.

The genus *Bifidobacterium* is one of the most commonly used types of bacteria cultures in the dairy industry for fermenting a variety of diary products. Ingestion of *Bifidobacterium*-containing products furthermore has a health-promoting effect. This effect is not only achieved by a lowered pH of the intestinal contents but also by the ability of *Bifidobacterium* to repopulate the intestinal flora in individuals who have had their intestinal flora disturbed by for example intake of antibiotics. *Bifidobacterium* furthermore has the potential of outcompeting potential harmful intestinal micro-organisms.

Galacto-oligosaccharides are known to enhance the growth of *Bifidobacterium*. This effect is likely achieved through the unique ability of *Bifidobacterium* to exploit galacto-oilgosaccharides as a carbon source. Dietary supplement of dalacto-oligosaccharides is furthermore thought to have a number of long-term disease protecting effects. For example, galacto-oligosaccharide intake has been shown to be highly protective against development of colorectal cancer in rats. There is therefore a great interest in developing cheap and efficient methods for producing galacto-oligosaccharides for use in the industry for improving dietary supplements and dairy products.

A beta-galactosidase polypeptide from *Ruminococcus/Blautia hansenii* having 1807 amino acids (having SEQ ID NO: 12) is known from the database UniProt, 24 Nov. 2009, "Subname: Full=Beta-galactosidase" XP002591904 retrieved from EBI accession no. UNIPROT:C9LAL1.

A glycosidase having 1768 amino acids (having SEQ ID NO: 13) is known from the database UniProt, 14 Oct. 2008, "Subname: Full=Putative uncharacterised protein" XP002610554 retrieved from EBI accession no. UNIPROT: B5CQV4.

An extracellular lactase from *Bifidobacterium bificium* DSM20215 truncated with approximately 580 amino acids (BIF3) has been described as a transgalactosylating enzyme in a solution containing lactose solubilised in water (Jørgensen et al. (2001), Appl. Microbiol. Biotechnol., 57: 647-652). In WO 2009/071539 a differently truncated fragment compared to BIF3 is described as resulting in efficient hydrolysis and very low production of GOS when tested in milk.

The *Bifidobacterium bifidum* lactase enzymes described above have the drawback of either requiring high lactose concentrations in order to exhibit transgalactosylase activity or predominantly having beta-galactosylase (hydrolase) activity.

There is still a need to develop enzymes that are efficient at producing GOS and which furthermore can work at low lactose substrate levels such as in milk.

OBJECT OF THE INVENTION

It is an object of embodiments of the invention to provide a polypeptide which has a useful ratio of transgalactosylation to hydrolysis activity and thus are efficient producers of GOS when incubated with lactose even at low lactose levels such as in a milk-based product. It is a further object of embodiments of the invention to provide a method for production of galacto-oligosaccharides (GOS) in situ in dairy products. It is a further object of embodiments of the invention to provide a method for developing a cheaper and more efficient method for production of galacto-oligosaccharides (GOS) for use in the industry.

SUMMARY OF THE INVENTION

The present invention discloses two related polypeptides, which surprisingly are able to produce galacto-oligosaccharidesin situ when incubated with lactose such as milk. Thus, when the polypeptide, as described herein, or a host cell expressing the polypeptide is incubated with lactose under appropriate conditions, galacto-oligosaccharides are produced at a high efficiency and thus lactose is reduced. The presence of galacto-oligosaccharides diary products or other comestible products has the advantage of enhancing the growth of healthpromoting *Bifidobacterium* sp. in the product or in the intestinal flora of the consumer after intake of the product or both.

In one aspect, the invention relates to an isolated polypeptide having transgalactosylating activity selected from the group consisting of:

a. a polypeptide comprising an amino acid sequence having at least 66% sequence identity to the amino acid sequence of the mature polypeptide of SEQ ID NO: 1,
b. a polypeptide comprising an amino acid sequence having at least 66% sequence identity to the amino acid sequence of the mature polypeptide of SEQ ID NO: 2,
c. a polypeptide encoded by a polynucleotide that hybridizes under at least low stringency conditions with i) the nucleic acid sequence comprised in SEQ ID NO: 10 encoding the mature polypeptide of SEQ ID NO: 1; ii) the cDNA sequence of i) or iii) the complementary strand of i) or ii);
d. a polypeptide encoded by a polynucleotide that hybridizes under at least low stringency conditions with i) the nucleic acid sequence comprised in SEQ ID NO: 11 encoding the mature polypeptide of SEQ ID NO: 2; ii) the cDNA sequence of i) or iii) the complementary strand of i) or ii);
e. a polypeptide comprising a conservative substitution, deletion and/or insertion of one or more amino acids of SEQ ID NO: 1, and
f. a polypeptide comprising a conservative substitution, deletion and/or insertion of one or more amino acids of SEQ ID NO: 2, provided that the polypeptide of above items a, c, and e at the most has a length of 1806 amino acids and provided that the polypeptide of above items b, d, and f at the most has a length of 1767 amino acids.

In one aspect, disclosed herein is a method of expressing a polypeptide, the method comprising obtaining a cell as disclosed herein and expressing the polypeptide from the cell, and optionally purifying the polypeptide. In a further aspect, disclosed herein is a composition comprising a polypeptide as disclosed herein, preferably a food composition, more preferably a dairy product. In a further aspect, disclosed herein is a method for producing a food product by treating a substrate comprising lactose with a polypeptide as disclosed herein such as producing a dairy product by treating a milk-based substrate comprising lactose with a polypeptide as disclosed herein. In a further aspect, the polypeptides are used for treating a substrate with a hydrolysing beta-galactosidase. In a further aspect, disclosed herein is a food product, preferably a dairy product, comprising a transgalactosylating enzyme obtained from *Ruminococcus hansenii* or *Ruminococcus lactaris*, preferably as defined in item a-f in above, and more preferably a polypeptide as further defined herein. In yet an aspect, disclosed herein is a galacto-oligosaccharide or composition thereof obtained by treating a substrate comprising lactose with a polypeptide as disclosed herein.

In one aspect, a polypeptide having transoalactosylating activity comprising an amino add sequence having
a. at least 66% sequence identity to the amino acid sequence of SEQ ID NO: 1, and/or
b. at least 66% sequence identity to the amino acid sequence of SEQ ID NO: 2, is provided.

In another aspect, a polypeptide having a ratio of transgalactosylting activity:β-galactosidase activity of at least 1 as measured at a concentration of 6 LAU/ml in a milk-based assay at 37° C. and 5 w/w % lactose after 30 minutes reaction comprising an amino add sequence having
a. at least 66% sequence identity to the amino acid sequence of SEQ ID NO: 1, and/or
b. at least 66% sequence identity to the amino acid sequence of SEQ ID NO: 2, is provided.

In a further aspect, a polypeptide comprising an amino acid sequence having at least 60% sequence identity to the amino acid sequence of SEQ ID NO: 5, is provided. In a further aspect, a polypeptide comprising an amino acid sequence having at least 94% sequence identity to the amino acid sequence of SEQ ID NO: 8, is provided. In a further aspect, the use of a polypeptide having transgalactosylating activity comprising an amino acid sequence having at least 60% sequence identity to the amino acid sequence of SEQ ID NO: 5 for producing galacto-oligosaccharides, is provided. In a further aspect, the use of a polypeptide having transgalactosylating activity comprising an amino acid sequence having at least 94% sequence identity to the amino acid sequence of SEQ ID NO: 8 for producing galacto-oligosaccharides, is provided.

In a further aspect, the use of a polypeptide having transgalactosylating activity comprising an amino acid sequence having
a. at least 60% sequence identity to the amino acid sequence of SEQ ID NO: 3,
b. at least 60% sequence identity to the amino acid sequence of SEQ ID NO: 4,
c. at least 60% sequence identity to the amino acid sequence of SEQ ID NO: 6, or
d. at least 80% sequence identity to the amino acid sequence of SEQ ID NO: 7, for producing galacto-oligosaccharides, is provided.

In a further aspect, a polypeptide having a ratio of transgalactosylating activity:β-galactosidase activity of at least 1 as measured at a concentration of 6 LAU/ml in a milk-based assay at 37° C. and 5 w/w % lactose after 30 minutes reaction, is provided. In a further aspect, a nucleic acid capable of encoding a polypeptide as disclosed herein, is provided. In a further aspect, a plasmid comprising a nucleic acid as disclosed herein, is provided. In a further aspect, an expression vector comprising a nucleic acid as disclosed herein, or capable of expressing a polypeptide as disclosed herein, is provided. In a further aspect, a host cell comprising, preferably transformed with, a plasmid as disclosed herein, or an expression vector as disclosed herein, is provided. In a further aspect, a cell capable of expressing a polypeptide as disclosed herein, is provided. In a further aspect, a method of expressing a polypeptide, the method comprising obtaining a host cell or a cell as disclosed herein and expressing the polypeptide from the cell or host cell, and optionally purifying the polypeptide, is provided. In a further aspect, a composition comprising a polypeptide as disclosed herein and a stabilizer, is provided. In a further aspect, a composition comprising a polypeptide as disclosed herein and a carbohydrate substrate, is provided. In a further aspect, a method for producing a dairy product by treating a milk-based substrate comprising lactose with a polypeptide having a ratio of transgalactosylating activity:β-galactosidase activity of at least 1, at least 2.5, at least 3, at least 4, at least 5, at least 6, at least 7, at least 8, at least 9, at least 10, at least 11, or at least 12 as measured at a concentration of 6 LAU/ml in a milk-based assay at 37° C. and 5 w/w % lactose after 30 minutes reaction is provided. In a further aspect, a method for producing a dairy product by treating a milk-based substrate comprising lactose with a polypeptide as disclosed herein, is provided. In a further aspect, a use of a cell as disclosed herein for producing a product selected from the group consisting of yoghurt, cheese, fermented milk product, dietary supplement and probiotic comestible product, is provided. In a further aspect, a dairy product comprising a cell as disclosed herein, is provided. In a further aspect, a dairy product comprising a polypeptide as disclosed herein, is provided. In a further aspect, a dairy product comprising a polypeptide as disclosed herein in a concentration of 001-1000 ppm, is provided. In a further aspect, a dairy product comprising an inactivated polypeptide as disclosed herein, is provided. In a further aspect, a dairy product comprising GOS formed in situ by a polypeptide as disclosed herein, is provided. In a further aspect, a use of a transgalactosylating polypeptide as disclosed herein or a cell as disclosed herein for producing galacto-oligosaccharides, is provided. In a further aspect, a use of a transgalactosylating polypeptide as disclosed herein or a cell as disclosed herein, for producing galacto-oligosaccharides to be part of a product selected from the group consisting of yoghurt, cheese, fermented dairy products, dietary supplements and probiotic comestible products, is provided. In a further aspect, a use of a transgalactosylating polypeptide as disclosed herein or a cell as disclosed herein, for producing galacto-oligosaccharides to enhance the growth of Bifidobacterium, is provided. In a further aspect, a use of a transgalactosylating polypeptide as disclosed herein or a cell as disclosed herein, for producing galacto-oligosaccharides to enhance the growth of Bifidobacterium in a mixed culture fermentation, is provided. In a further aspect, a process for producing a transgalactosylating polypeptide as disclosed herein, comprising culturing a cell as disclosed herein in a suitable culture medium under conditions permitting expression of said polypeptide, and recovering the resulting polypeptide from the culture, is provided. In a further aspect, a process for producing galacto-oligosaccharides, comprising contacting of an polypeptide as disclosed herein or a cell as disclosed herein with a milk-based solution comprising lactose.

SEQUENCE LISTING

SEQ ID NO: 1 is a 1125 amino acid truncated fragment of SEQ ID NO: 12.
SEQ ID NO: 2 is 1150 amino acid truncated fragment of SEQ ID NO: 13.
SEQ ID NO: 3 is amino acid residues 559-649 of SEQ ID No: 1.
SEQ ID NO: 4 is amino acid residues 579-649 of SEQ ID No: 1.
SEQ ID NO: 5 is amino acid residues 579-636 of SEQ ID No: 1.
SEQ ID NO: 6 is amino acid residues 575-665 of SEQ ID No: 2.
SEQ ID NO: 7 is amino acid residues 594-665 of SEQ ID No: 2.
SEQ ID NO: 8 is amino acid residues 594-652 of SEQ ID No: 2.
SEQ ID NO: 9 is a signal peptide from the pBN Bacillus subtilis expression vector.
SEQ ID NO: 10 is the nucleotide sequence encoding SEQ ID NO: 1 including sequence encoding the signal peptide.
SEQ ID NO: 11 is the nucleotide sequence encoding SEQ ID NO: 2 including sequence encoding the signal peptide.
SEQ ID NO: 12 is a beta-galactosidase from Ruminococcus/Blautia hansenii DSM 20583.
SEQ ID NO: 13 is a glycosidase from Ruminococcus lactaris, ATCC 29176.
SEQ ID NO: 14 is the nucleotide sequence encoding SEQ ID NO: 12 without the signal sequence.
SEQ ID NO: 15 is the nucleotide sequence encoding SEQ ID NO: 13 without the signal sequence.
SEQ ID NO: 16 is the nucleotide sequence encoding SEQ ID NO: 1.
SEQ ID NO: 17 is the nucleotide sequence encoding SEQ ID NO: 2.

LEGENDS TO THE FIGURE

FIG. 1 shows a plasmid map of the Ruminococcus hansenii expression construct. The rhBIF3d3 coding sequence was fused inframe with the aprE signal sequence using BssHII and PacI as restriction sites.

FIG. 2 shows accumulation of galactose and glucose during enzymatic treatment of a 5% w/w lactose solution in T-buffer with Lactozym® as control, Ruminococcus hansenii (SEQ ID NO: 1), Ruminococcus lactaris (SEQ ID NO:2) and Bifidobacterium bifidum BIF3d3 (truncated) (as described by Jørgensen et al. (2001), Appl. Microbiol. Biotechnol., 57: 647-652 and EP patent 1,283,876).

DETAILED DISCLOSURE OF THE INVENTION

Figure 1:
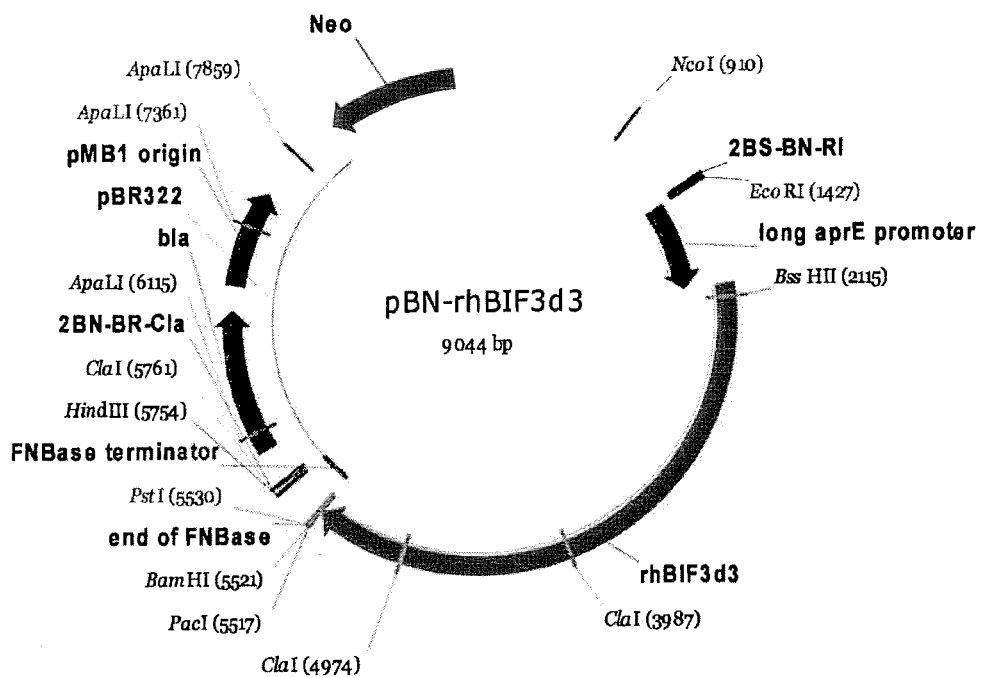

Disclosed herein is an isolated polypeptide having transgalactosylating activity selected from the group consisting of:
  a. a polypeptide comprising an amino acid sequence having at least 66% sequence identity to the amino acid sequence of the mature polypeptide of SEQ ID NO: 1,
  b. a polypeptide comprising an amino acid sequence having at least 66% sequence identity to the amino acid sequence of the mature polypeptide of SEQ ID NO: 2,
  c. a polypeptide encoded by a polynucleotide that hybridizes under at least low stringency conditions with i) the nucleic acid sequence comprised in SEQ ID NO: 10 encoding the mature polypeptide of SEQ ID NO: 1; ii) the cDNA sequence of i) or iii) the complementary strand of i) or ii);
  d. a polypeptide encoded by a polynucleotide that hybridizes under at least low stringency conditions with i) the nucleic acid sequence comprised in SEQ ID NO: 11 encoding the mature polypeptide of SEQ ID NO: 2; ii) the cDNA sequence of i) or iii) the complementary strand of i) or ii);
  e. a polypeptide comprising a conservative substitution, deletion and/or insertion of one or more amino acids of SEQ ID NO: 1, and
  f. a polypeptide comprising a conservative substitution, deletion and/or insertion of one or more amino acids of SEQ ID NO: 2,
provided that the polypeptide of above items a, c, and e at the most has a length of 1806 amino acids and provided that the polypeptide of above items b, d, and f at the most has a length of 1767 amino acids.

In accordance with this detailed description, the following abbreviations and definitions apply; It should be noted that as used herein, the singular forms "a," "an," and "the" include plural referents unless the context clearly dictates otherwise. Thus, for example, reference to "an polypeptide" includes a plurality of such polypeptides, and reference to "the formulation" includes reference to one or more formulations and equivalents thereof known to those skilled in the art, and so forth.

Unless defined otherwise, all technical and scientific terms used herein have the same meaning as commonly understood by one of ordinary skill in the art. The following terms are provided below.

"Transgalactosylase" means an enzyme that, among other things, is able to transfer galactose to the hydroxyl groups of D-galactose or D-glucose whereby galacto-oligosaccharides are produced. In one aspect, a transgalactosylase is identified by reaction of the enzyme on lactose in which the amount of galactose generated is less than the amount of glucose generated at any given time.

In the present context, the term "transgalactosylating activity" means the transfer of a galactose moiety to a molecule other than water and is measured as [glucose]−[galactose] generated at any given time during reaction.

In the present context the term "β-galactosidase activity" means the ability of an enzyme to hydrolyse β-galactosides such as for example lactose into monosaccharides, glucose and galactose.

In the present context, the term "relative transgalactosylation activity" means ([Glucose]-[Galactose]100)/[Glucose]) measured at a timepoint after 15 minutes of reaction time.

In the present context, the term [Glucose] means the glucose concentration in % by weight as measured by HPLC.

In the present context, the term [Galactose] means the galactose concentration in % by weight as measured by HPLC.

In the present context, the term "after 15 min. reaction" means the amount of time which should pass before measurement of activity after incubation with the herein described polypeptide in an assay.

In one aspect, the activity is measured after 15 min. reaction, 30 min. reaction, 60 min. reaction, 90 min. reaction, 120 min. reaction or 180 min. reaction. Thus in one aspect, as an example the relative transgalactosylation activity is measured 15 minutes after addition of enzyme, such as 30 minutes after addition of enzyme, such as 60 minutes after addition of enzyme, such as 90 minutes after addition of enzyme, such as 120 minutes after addition of enzyme or such as 180 minutes after addition of enzyme.

In the present context, the term "ratio of transgalactosylating activity; β-galactosidase activity" means ([Glucose]−[Galactose]/[Galactose]).

In the present context, the term "lactose has been transgalactosylated" means that a galactose molecule has been covalently linked to the lactose molecule such as for example covalently linked to any of the free hydroxyl groups in the lactose molecule or as generated by internal transgalatosylation for example forming allolactose.

In the present context, the term "milk-based assay" means an assay performed in milk, reconstituted milk or solutions containing main milk constituents such as for example lactose. In one embodiment, a milk-based assay is performed by preparing samples in 9% reconstituted milk from skimmed milk powder (such as e.g. Humana Milk Union, DE NW508 EG) giving a final concentration of lactose of 5% w/w. Enzymes are dosed based upon the LAU activity determined as described below giving the desired final concentration in LAU/ml.

A sample is taken prior to addition of enzyme and additional samples are taken at indicated time points and the enzymes are immediately inactivated by incubating at 95° C. for 10 minutes. Samples are diluted 1:10 and 2 µL are applied onto activated (161° C. for 10 min) HPTLC silica gel 60 (Merck Cat#1.05541.0001) plates with a CAMAG Automatic TLC Sampler 4. The TLC plates are eluted with an eluent containing (80) Acetonitril: (20) Ethylacetat: (50) 1-Propanol: (40) Water. Samples are visualised by heating (161° C. for 10 min) and allowed to cool down before soaking in 5% w/w H2SO4 in 99.9% w/w ethanol. Plates are developed with heating 161° C. for 3 min.

In one aspect, such an assay is as described in example 3.

In the context of the present application, 1 lactase unit (1 LAU) is the amount of enzyme which releases 1 micromole glucose per minute in M-buffer at pH 6.5 and 37° C. with a lactase concentration of 4.75% w/v. M-buffer is prepared by dissolving 3.98 g $C_6H_5Na_3O_7$-5 $2H_2O$, 8.31 g citric acid, 0.9 g $K_2SO_4$, 2.6 g $K_2HPO_4$, 7.35 g $KH_2PO_4$, 5.45 g KOH, 4.15 g, $MgCl_2$ $6H_2O$, 3.75 g CaCl2 $2H_2O$ and 1.4 g $NaHCO_3$ in 4 liter water, adding 12.5 ml 4N NaOH, adjusting to pH 6.5 using HCl, and adding water up to a total volume of 5 liter.

The activity in LAU of a specific lactase may be determined by direct measurement of glucose released from lactose under the conditions described above. The skilled person will know how to determine such activity. Alternatively, the activity may be determined by using the lactase activity assay described in Example 1 of the present application. Here, the activity is obtained by comparing to a standard curve with a lactase of known activity, and the activity of the unknown sample calculated from this. The lactase of known activity may e.g., be Lactozym obtained from Novozymes A/S, Denmark.

In the present context, the term "which polypeptide is freeze-dried" means that the polypeptide has been obtained by freeze-drying a liquid of the polypeptide at an appropriate pressure and for an appropriate period removing the water.

In the present context, the term "which polypeptide is in solution" relates to a polypeptide which is soluble in a solvent without precipitating out of solution. A solvent for this purpose includes any millieu in which the polypeptide may occur, such as an aqueous buffer or salt solution, a fermentation broth, or the cytoplasm of an expression host.

In the present context, the term "stabilizer" means any stabilizer for stabilizing the polypeptide e.g., a polyol such as e.g., glycerol or propylene glycol, a sugar or a sugar alcohol, lactic acid, boric add, or a boric acid derivative (e.g., an aromatic borate ester). In one aspect, the stabilizer is glycerol.

In the present context, the term "carbohydrate substrate" means an organic compound with the genera; formula $C_m(H_2O)_n$, that is, consisting only of carbon, hydrogen and oxygen, the last two in the 2:1 atom ratio such as a disaccharide.

In the present context, the term "disaccharide" is two monosaccharide units bound together by a covalent bond known as a olycosidic linkage formed via a dehydration reaction, resulting in the loss of a hydrogen atom from one monosaccharide and a hydroxyl group from the other. The formula of unmodified disaccharides is $C_{12}H_{22}O_{11}$. In one aspect, the disaccharide is lactulose, trehalose, rhamnose, maltose, sucrose, lactose, or celloblose. In a further aspect, the disaccharide is lactose.

The term "isolated" means that the sequence is at least substantially free from at least one other component with which the sequence is naturally associated in nature and as found in nature. In one aspect, "isolated polypeptide" as used herein refers to a polypeptide which is at least 30% pure, at least 40% pure, at least 60% pure, at least 80% pure, at least 90% pure, and at least 95% pure, as determined by SDS-PAGE.

The term "substantially pure polypeptide" means herein a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides disclosed herein are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods. Herein, the term "substantially pure polypeptide" is synonymous with the terms "isolated polypeptide" and "polypeptide in isolated form."

The term "purified" or "pure" means that a given component is present at a high level state—e.g. at least about 51% pure, or at least about 75%, or at least about 80%, or at least about 90% pure, or at least about 95% pure or at least about 98% pure. The component is desirably the predominant active component present in a composition.

The term "microorganism" in relation to the present invention includes any microorganism that could comprise a nucleotide sequence according to the present invention or a nucleotide sequence encoding for a polypeptide having the specific properties as defined herein and/or products obtained therefrom.

In the present context, "microorganism" may include any bacterium or fungus being able to ferment a milk substrate.

The term "host cell"—in relation to the present invention includes any cell that comprises either a nucleotide, sequence encoding a polypeptide having the specific properties as defined herein or an expression vector as described above and which is used in the production of a polypeptide having the specific properties as defined herein. In one aspect, the production is recombinant production.

The term "milk", in the context of the present invention, is to be understood as the lacteal secretion obtained from any mammal, such as cows, sheep, goats, buffaloes or camels.

In the present context, the term "milk-based substrate" means any raw and/or processed milk material or a material derived from milk constituents. Useful milk-based substrates include, but are not limited to solutions/suspensions of any milk or milk like products comprising lactose, such as whole or low fat milk, skim milk, buttermilk, reconstituted milk powder, condensed milk, solutions of dried milk, UHT milk, whey, whey permeate, acid whey, or cream. Preferably, the milk-based substrate is milk or an aqueous solution of skim milk, powder. The milk-based substrate may be more concentrated than raw milk. In one embodiment, the milk-based substrate has a ratio of protein to lactose of at least 0.2, preferably at least 0.3, at east 0.4, at east 0.5, at least 0.5 or, most preferably, at least 0.7. The milk-based substrate may be homogenized and/or pasteurized according to methods known in the art.

"Homogenizing" as used herein means intensive mixing to obtain a soluble suspension or emulsion. It may be performed so as to break up the milk fat into smaller sizes so that it no longer separates from the milk. This may be accomplished by forcing the milk at high pressure through small orifices.

"Pasteurizing" as used herein means reducing or eliminating the presence of live organisms, such as microorganisms, in the milk-based substrate. Preferably, pasteurization is attained by maintaining a specified temperature for a specified period of time. The specified temperature is usually attained by heating. The temperature and duration may be selected in order to kill or inactivate certain bacteria, such as harmful bacteria, and/or to inactivate enzymes in the milk. A rapid cooling step may follow.

A "food product" or "food composition" in the context of the present invention may be any comestible food or feed product suitable for consumption by an animal or human.

A "dairy product" in the context of the present invention may be any food product wherein one of the major constituents is milk-based. Preferable, the major constituent is milk-based. More preferably, the major constituent is a milk-based substrate which has been treated with an enzyme having transgalactosylating activity.

In the present context, "one of the major constituents" means a constituent having a dry matter which constitutes more than 20%, preferably more than 30% or more than 40% of the total dry matter of the dairy product, whereas "the major constituent" means a constituent having a dry matter which constitutes more than 50%, preferably more than 60% or more than 70% of the total dry matter of the dairy product.

A "fermented dairy product" in present context is to be understood as any dairy product wherein any type of fermentation forms part of the production process. Examples of fermented dairy products are products like yoghurt, buttermilk, creme fraiche, quark and fromage frail. A fermented dairy product may be produced by any method known in the art.

The term "fermentation" means the conversion of carbohydrates into alcohols or acids through the action of a microorganism such as a starter culture. In one aspect, fermentation comprises conversion of lactose to lactic acid.

In the present context the term "Pfam domains" means regions within a protein sequence that are identified as either Pfam-A or Pfam-B based on multiple sequence alignments and the presence of Hidden Markov Motifs ("*The Pfam protein families database*": R. D. Finn, J. Mistry, Tate, P. Coggill, A. Heger, J. E. Pollington, O. L. Gavin, P. Gunesekaran, G. Ceric, K. Forslund, L. Holm, E. L. Sonnhammer, S. R. Eddy, A. Bateman Nucleic Acids Research (2010) Database Issue 38:D211-222.). As examples of Pfam domains mention may be made of Glyco_hydro2N (PF02837), Glyco_hydro (PF00703), Glyco_hydro 2C (PF02836) and Bacterial Ig-like domain (group 4) (PF07532).

As used herein "a position corresponding to position" means that an alignment as described herein is made between a particular query polypeptide and the reference polypeptide. The position corresponding to a specific position in the reference polypeptide is then identified as the corresponding amino acid in the alignment with the highest sequence identity.

In one aspect, a polypeptide having transgalactosylating activity comprising an amino acid sequence having
  a. at least 66% sequence identity to the amino acid sequence of SEQ ID NO: 1, and/or
  b. at least 66% sequence identity to the amino acid sequence of SEQ ID NO: 2, is provided.

In one aspect, a polypeptide, wherein the amino acid sequence comprises at least one or more amino acid residue(s) selected from the following groups:
  a. an amino acid residue selected from the group consisting of D/E/N/Q at a position corresponding to position 576 in SEQ ID NO: 1, b. an amino acid residue selected from the group consisting of D/E/N/Q at a position corresponding to position 588 in SEQ ID NO: 1,
c. an amino acid residue selected from the group consisting of E/D/Q/N at a position corresponding to position 592 in SEQ ID NO: 1 and/or
d. an amino acid residue selected from the group consisting of D/E/Q/N at a position corresponding to position 625 in SEQ ID NO: 1, is provided.

In one aspect, a polypeptide, wherein the amino acid sequence comprises at least one or more amino acid residue(s) selected from the following groups:
a. an amino acid residue selected from the group consisting of D/E/N/Q at a position corresponding to position 592 in SEQ ID NO: 2,
b. an amino acid residue selected from the group consisting of D/E/N/Q at a position corresponding to position 604 in SEQ ID NO: 2,
c. an amino acid residue selected from the group consisting of E/D/Q/N at a position corresponding to position 608 in SEQ ID NO: 2 and/or
d. an amino acid residue selected from the group consisting of D/E/Q/N at a position corresponding to position 641 in SEQ ID NO: 2, is provided.

It has been found that the amino acid at a position corresponding to position 576, 588, 592 and 625 in SEQ ID NO:1 and the respective amino acids at a position corresponding to position 592, 604, 608 and 641 in SEQ ID NO:2 have an effect on the activity of the polypeptides disclosed herein.

In one aspect, disclosed herein is a polypeptide, wherein the amino acid sequence comprises at least one or more acidic amino acid residue(s) such as D or E, in a position corresponding to position 576, 588, 592 and 625 in SEQ ID NO:1 or in a position corresponding to position 592, 604, 608 and 641 in SEQ ID NO:2.

In another aspect, the present invention relates to a polypeptide having a ratio of transgalactosylating activity:β-galactosidase activity of at least 1 as measured at a concentration of 6 LAU/ml in a milk-based assay at 37° C. and 5 w/w % lactose after 30 minutes reaction comprising an amino acid sequence having
a. at least 66% sequence identity to the amino acid sequence of SEQ ID NO: 1, and/or
b. at least 66% sequence identity to the amino acid sequence of SEQ ID NO: 2, is provided.

In a further aspect, a polypeptide comprising an amino acid sequence having at least 60% sequence identity to the amino acid sequence of SEQ ID NO: 5, is provided. In a further aspect, a polypeptide comprising an amino acid sequence having at least 94% sequence identity to the amino acid sequence of SEQ ID NO: 8, is provided. In a further aspect, the use of a polypeptide having transgalactosylating activity comprising an amino acid sequence having at least 60% sequence identity to the amino acid sequence of SEQ ID NO: 5 for producing galacto-oligosaccharides, is provided. In a further aspect, the use of a polypeptide having transgalactosylating activity comprising an amino acid sequence having at least 94% sequence identity to the amino acid sequence of SEQ ID NO: 8 for producing galacto-oligosaccharides, is provided.

In a further aspect, the use of a polypeptide having transgalactosylating activity comprising an amino acid sequence having
a. at least 60% sequence identity to the amino acid sequence of SEQ ID NO: 3,
b. at least 60% sequence identity to the amino acid sequence of SEQ ID NO: 4,
c. at least 60% sequence identity to the amino acid sequence of SEQ ID NO: 6, or
d. at least 60% sequence identity to the amino acid sequence of SEQ ID NO: 7, for producing galacto-oligosaccharides, is provided.

In a further aspect, a polypeptide comprising an amino acid sequence having at least 66% sequence identity to the amino acid sequence of SEQ ID NO: 1, and at least 60% sequence identity to the amino acid sequence of SEQ ID NO: 5, is provided.

In a further aspect, a polypeptide comprising an amino acid sequence having at least 66% sequence identity to the amino acid sequence of SEQ ID NO: 2, and at least 94% sequence identity to the amino acid sequence of SEQ ID NO: 8, is provided.

In a further aspect, a polypeptide containing one or more Pfam domains selected from: Glyco_hydro2N (PF02837), Glyco_hydro (PF00703), Glyco_hydro 2C (PF02836) and Bacterial Ig-like domain (group 4) (PF07532), is provided. In yet a further aspect, a polypeptide containing the Pfam domains Glyco_hydro2N (PF02837), Glyco_hydro (PF00703), Glyco_hydro 2C (PF02836) and Bacterial Ig-like domain (group 4) (PF07532), is provided. In yet a further aspect, a polypeptide containing the Glyco_hydro2N (PF02837), Glyco_hydro (PF00703), and Glyco_hydro 2C (PF02836) domains which domains constitutes the catalytic domain of the polypeptide, is provided.

In a further aspect, a polypeptide comprising an amino acid sequence and having a ratio of transgalactosylating activity:β-galactosidase activity of at least 1, at least 2.5, at least 3, at least 4, at least 5, at least 6, at least 7, at least 8, at least 9, at least 10, at least 11, or at least 12 as measured at a concentration of 6 LAU/ml in a milk-based assay at 37° C. and 5 w/w % lactose after 15 or 30 minutes reaction, is provided. In a further aspect, the polypeptide is derived from *Ruminococcus hansenii* or *Ruminococcus lactaris*.

In one aspect, the herein disclosed polypeptide(s) has a transgalactosylating activity such that more than 20%, more than 30%, more than 40%, up to 50% of the initial lactose is transgalactosylated as measured at a concentration of 6 LAU/ml in a milk-based assay at 37° C. and 5 w/w % lactose after 30 minutes of reaction.

In a further aspect, the herein disclosed polypeptide(s) has a β-galactosidase activity such that less than 80%, less than 70%, less than 60%, less than 50%, less than 40%, less than 30%, less than 20% of the lactose has been hydrolysed as measured at a concentration of 6 LAU/ml in a milk-based assay at 37° C. and 5 w/w % lactose after 30 minutes of reaction.

In one aspect, the β-galactosidase activity and/or the transgalactosylating activity are measured at a concentration of 6 LAU/ml, 3 LAU/ml or 1 LAU/ml.

In a further aspect, the herein disclosed polypeptide(s) has one or more of the following characteristics:
a) a ratio of transgalactosylating activity:β-galactosidase activity of at least of at least 1, at least 2.5, at least 3, at least 4, at least 5, at least 6, at least 7, at east 8, at least 9, at least 10, at least 11, or at least 12 as measured at a concentration of 6 LAU/ml in a milk-based assay at 37° C. and 5 w/w % lactose after 30 minutes reaction, and/or
b) has a transgalactosylating activity such that more than 20%, more than 30%, more than 40%, and up to 50% of the initial lactose has been transgalactosylated as measured at a concentration of 6 LAU/ml in a milk-based assay at 37° C. and 5 w/w % lactose after 30 minutes of reaction.

In a further aspect, a polypeptide comprising an amino acid sequence having at least 60% sequence identity to the amino acid sequence of SEQ ID NO: 5, is provided. In a further aspect, a polypeptide comprising an amino acid sequence having at least 94% sequence identity to the amino acid sequence of SEQ ID NO: 8, is provided. In yet a further aspect, a polypeptide comprising an amino acid sequence having at least 60% sequence identity to the amino acid sequence of SEQ ID NO: 3, is provided. In yet a further aspect, a polypeptide comprising an amino acid sequence having at least 60% sequence identity to the amino acid sequence of SEQ ID NO: 4, is provided. In yet a further aspect, a polypeptide comprising an amino acid sequence having at least 94% sequence identity to the amino acid sequence of SEQ ID NO: 6, is provided. In yet a further aspect, a polypeptide comprising an amino acid sequence having at least 94% sequence identity to the amino acid sequence of SEQ ID NO: 7, is provided.

Proteins are generally comprised of one or more functional regions, commonly termed domains. The presence of different domains in varying combinations in different proteins gives rise to the diverse repertoire of proteins found in nature. One way of describing the domains are by the help of the Pfam database which is a large collection of protein domain families as described in "*The Pfam protein families database*": R. D. Finn, 1 Mistry J. Tate, P. Coggill, A. Heger, J. E. Pollington, O. L. Gavin, P. Gunesekaran, G. Ceric, K. Forslund, L. Holm, E. L. Sonnhammer, S. R. Eddy, A. Bateman Nucleic Acids Research (2010) Database Issue 38:D211-222. Each family is represented by multiple sequence alignments and hidden Markov models (HMMs). In a further aspect, the present inventors have found that the herein provided polypeptide(s) contains one or more of the Pfam domains Glyco_hydro2N (PF02837), Glyco_hydro (PF00703), Glyco_hydro 2C (PF02836) and Bacterial Ig-like domain (group 4) (PF07532). In one aspect, the herein provided polypeptide(s) contains Glyco_hydro2N (PF02837), Glyco_hydro (PF00703), Glyco_hydro 2C (PF02836) and Bacterial Ig-like domain (group 4) (PF07532).

In one aspect, the herein disclosed polypeptide(s) comprises an amino acid sequence having an amino acid residue selected from the group consisting of D, E, N and Q at a position corresponding to position 576 in SEQ ID NO: 1. In one aspect, the herein disclosed polypeptide(s) comprises an amino acid sequence having an amino acid residue selected from the group consisting of D, E and N at a position corresponding to position 576 in SEQ ID NO: 1. In one aspect, the herein disclosed polypeptide(s) comprises an amino acid sequence having an amino acid residue selected from the group consisting of D and E at a position corresponding to position 576 in SEQ ID NO: 1. In one aspect, the herein disclosed polypeptide(s) comprises an amino acid sequence the amino acid residue D at a position corresponding to position 576 in SEQ ID NO: 1.

In one aspect, the herein disclosed polypeptide(s) comprises an amino acid sequence having an amino acid residue selected from the group consisting of D, E, N and Q at a position corresponding to position 588 in SEQ ID NO: 1. In one aspect, the herein disclosed polypeptide(s) comprises an amino acid sequence having an amino acid residue selected from the group consisting of D, E and N at a position corresponding to position 588 in SEQ ID NO: 1. In one aspect, the herein disclosed polypeptide(s) comprises an amino acid sequence having an amino acid residue selected from the group consisting of D and E at a position corresponding to position 588 in SEQ ID NO: 1. In one aspect, the herein disclosed polypeptide(s) comprises an amino acid sequence the amino acid residue D at a position corresponding to position 588 in SEQ ID NO: 1.

In one aspect, the herein disclosed polypeptide(s) comprises an amino acid sequence having an amino acid residue selected from the group consisting of D, E, N and Q at a position corresponding to position 592 in SEQ ID NO: 1. In one aspect, the herein disclosed polypeptide(s) comprises an amino acid sequence having an amino acid residue selected from the group consisting of D, E and Q at a position corresponding to position 592 in SEQ ID NO: 1. In one aspect, the herein disclosed polypeptide(s) comprises an amino acid sequence having an amino acid residue selected from the group consisting of D and E at a position corresponding to position 592 in SEQ ID NO: 1. In one aspect, the herein disclosed polypeptide(s) comprises an amino acid sequence the amino acid residue E at a position corresponding to position 592 in SEQ ID NO: 1.

In one aspect, the herein disclosed polypeptide(s) comprises an amino acid sequence having an amino acid residue selected from the group consisting of D, E, N and Q at a position corresponding to position 625 in SEQ ID NO: 1. In one aspect, the herein disclosed polypeptides) comprises an amino acid sequence having an amino acid residue selected from the group consisting of D, E and N at a position corresponding to position 625 in SEQ ID NO: 1. In one aspect, the herein disclosed polypeptide(s) comprises an amino acid sequence having an amino acid residue selected from the group consisting of D and E at a position corresponding to position 625 in SEQ ID NO: 1. In one aspect, the herein disclosed polypeptide(s) comprises an amino acid sequence the amino acid residue D at a position corresponding to position 625 in SEQ ID NO: 1.

In one aspect, the polypeptides have useful transgalactosylating activity over a range of pH of 4-9, such as 5-8, such as 5.5-7.5.

The present invention encompasses polypeptides having a certain degree of sequence identity or sequence homology with amino acid sequence(s) defined herein or with a polypeptide having the specific properties defined herein. The present invention encompasses, in particular, peptides having a degree of sequence identity with any one of SEQ ID NO: 1-8, defined below, or homologues thereof.

In one aspect, the homologous amino acid sequence and/or nucleotide sequence should provide and/or encode a polypeptide which retains the functional transgalactosylating activity and/or enhances the transgalactosylating activity compared to a polypeptide of SEQ ID NO: 1 or 2.

In the present context, a homologous sequence is taken to include an amino acid sequence which may be at least 66%, 70%, 75%, 78%, at least 80%, at least 85%, at least 90%, at least 95%, at least 96%, at least 97%, at least 98% or at least 99%, identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

Sequence identity comparisons can be conducted by eye, or more usually, with the aid of readily available sequence comparison programs. These commercially available computer programs use complex comparison algorithms to align two or more sequences that best reflect the evolutionary events that might have led to the difference(s) between the two or more sequences. Therefore, these algorithms operate with a scoring system rewarding alignment of identical or similar amino acids and penalising the insertion of gaps, gap extensions and alignment of non-similar amino acids. The scoring system of the comparison algorithms include:

i) assignment of a penalty score each time a gap is inserted (gap penalty score),
ii) assignment of a penalty score each time an existing gap is extended with an extra position (extension penalty score),
iii) assignment of high scores upon alignment of identical amino acids, and
iv) assignment of variable scores upon alignment of non-identical amino acids.

Most alignment programs allow the gap penalties to be modified. However, it is preferred to use the default values when using such software for sequence comparisons.

The scores given for alignment of non-identical amino acids are assigned according to a scoring matrix also called a substitution matrix. The scores provided in such substitution matrices are reflecting the fact that the likelihood of one amino acid being substituted with another during evolution varies and depends on the physical/chemical nature of the amino acid to be substituted. For example, the likelihood of a polar amino acid being substituted with another polar amino acid is higher compared to being substituted with a hydrophobic amino acid. Therefore, the scoring matrix will assign the highest score for identical amino acids, lower score for non-identical but similar amino acids and even lower score for non-identical non-similar amino acids. The most frequently used scoring matrices are the PAM matrices (Dayhoff et al. (1978), Jones et al. (1992)), the BLOSUM matrices (Henikoff and Henikoff (1992)) and the Gonnet matrix (Gonnet et al. (1992)).

Suitable computer programs for carrying out such an alignment include, but are not limited to, Vector NTI (Invitrogen Corp.) and the ClustalV, ClustalW and ClustalW2 programs (Higgins D G & Sharp P M (1988), Higgins et al. (1992), Thompson et al. (1994), Larkin et al. (2007). A selection of different alignment tools is available from the ExPASy Proteomics server at www.expasy.org. Another example of software that can perform sequence alignment is BLAST (Basic Local Alignment Search Tool), which is available from the webpage of National Center for Biotechnology Information which can currently be found at www.ncbi.nlm.nih.gov/ and which was firstly described in Altschul et al. (1990) J. Mol. Biol. 215; 403-410.

Once the software has produced an alignment, it is possible to calculate % similarity and % sequence identity. The software typically does this as part of the sequence comparison and generates a numerical result.

In one embodiment, it is preferred to use the ClustalW software for performing sequence alignments. Preferably, alignment with ClustalW is performed with the following parameters for pairwise alignment:

| Substitution matrix: | Gonnet 250 |
|---|---|
| Gap open penalty: | 20 |
| Gap extension penalty: | 0.2 |
| Gap end penalty: | None |

ClustalW2 is for example made available on the Internet by the European Bioinformatics Institute at the EMBL-EBI webpage www.ebl.ac.uk under tools—sequence analysis—ClustalW2. Currently, the exact address of the ClustalW2 tool is www.ebi.ac.uk/Tools/clustalw2.

In another embodiment, it is preferred to use the program Align X in Vector NTI (Invitrogen) for performing sequence alignments. In one embodiment, Exp10 has been may be used with default settings:

Gap opening penalty: 10
Gap extension penalty: 0.05
Gapseparation penalty range: 8

In a particular embodiment, the percentage of identity of one amino acid sequence with, or to, another amino acid sequence is determined by the use of the score matrix: blosum62mt2 and the VectorNTI Pairwise alignment settings

| Settings | K-tuple | 1 |
|---|---|---|
| | Number of best diagonals | 5 |
| | Window size | 5 |
| | Gap Penalty | 3 |
| | Gap opening Penalty | 10 |
| | Gap extension Penalty | 0.1 |

Thus, the present invention also encompasses variants, homologues and derivatives of any amino acid sequence of a protein or polypeptide as defined herein, particularly those of SEQ ID NO: 1 or those of SEQ ID NO: 2, 3, 4, 5, 6, 7 or 8 defined below.

The sequences, particularly those of variants, homologues and derivatives of SEQ ID NO: 1, 2, 3, 4, 5, 6, 7 or 8 defined below, may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic add; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

The present invention also encompasses conservative substitution (substitution and replacement are both used herein to mean the interchange of an existing amino acid residue, with an alternative residue) that may occur i.e. like-for-like substitution such as basic for basic, acidic for acidic, polar for polar etc. Non-conservative substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Conservative substitutions that may be made are, for example within the groups of basic amino acids (Arginine, Lysine and Histidine), acidic amino acids (glutamic acid and aspartic acid), aliphatic amino acids (Alanine, Valine, Leucine, Isoleucine), polar amino acids (Glutamine, Asparagine, Serine, Threonine), aromatic amino acids (Phenylalanine, Tryptophan and Tyrosine), hydroxyl amino acids (Serine, Threonine), large amino acids (Phenylalanine and Tryptophan) and small amino acids (Glycine, Alanine).

In one embodiment, the polypeptide is a polypeptide having the sequence shown in SEQ ID NO: 1 or a polypeptide variant having at least at least 66%, at least 70%, at least 75%, at least 78%, at least 80%, at least 85%, at least 90%, at least 95%, at least 96%, at least 97%, at least 98% or at least 99% amino acid sequence identity therewith. In one embodiment, the polypeptide is a polypeptide having the sequence shown in SEQ ID NO: 1 or a polypeptide variant having at least at least 70% amino acid sequence identity therewith. In one embodiment, the polypeptide is a polypeptide having the sequence shown in SEQ ID NO: 1 or a polypeptide variant having at least at least 75% amino acid sequence identity therewith. In one embodiment, the polypeptide is a polypeptide having the sequence shown SEQ ID NO: 1 or a polypeptide variant having at least at least 80% amino acid sequence identity therewith.

In one embodiment, the polypeptide is a polypeptide having the sequence shown in SEQ ID NO: 3 or a polypeptide variant having at least at least 60%, at least 65%, at least 70%, at least 75%, at least 78%, at least 80%, at least 85%, at least 90%, at least 95%, at least 96%, at least 97%, at least 98% or at least 99% amino acid sequence identity therewith.

In one embodiment, the polypeptide is a polypeptide having the sequence shown in SEQ ID NO: 4 or a polypeptide variant having at least 60%, at least 65%, at least 70%, at least 75%, at least 78%, at least 80%, at east 85%, at least 90%, at least 95%, at least 96%, at least 97%, at least 98% or at least 99% amino acid sequence identity therewith.

In one embodiment, the polypeptide is a polypeptide having the sequence shown in SEQ ID NO: 5 or a polypeptide variant having at least 60%, at least 65%, at least 70%, at least 75%, at least 78%, at least 80%, at least 85%, at least 90%, at least 95%, at least 96%, at least 97%, at least 98% or at least 99% amino acid sequence identity therewith.

In one embodiment, the polypeptide is a polypeptide having the sequence shown in SEQ ID NO: 2 or a polypeptide variant having at least 60%, at least 65%, at least 75%, at least 78%, at least 80%, at least 85%, at least 90%, at least 95%, at least 96%, at least 97%, at least 98% or at least 99% amino acid sequence identity therewith. In one embodiment, the polypeptide is a polypeptide having the sequence shown in SEQ ID NO: 2 or a polypeptide variant having at least at least 70% amino acid sequence identity therewith. In one embodiment, the polypeptide is a polypeptide having the sequence shown in SEQ ID NO: 2 or a polypeptide variant having at least at least 75% amino acid sequence identity therewith. In one embodiment, the polypeptide is a polypeptide having the sequence shown in SEQ ID NO: 2 or a polypeptide variant having at least at least 80% amino acid sequence identity therewith.

In one embodiment, the polypeptide is a polypeptide having the sequence shown in SEQ ID NO: 6 or a polypeptide variant having at Beast at least 65%, at least 70%, at least 75%, at least 75%, at least 80%, at least 85%, at least 90%, at least 94%, at least 95%, at least 96%, at least 97%, at least 98% or at least 99% amino acid sequence identity therewith.

In one embodiment, the polypeptide is a polypeptide variant having the sequence shown in SEQ ID NO: 7 or a polypeptide variant having at least at least 65%, at least 70%, at least 75%, at least 78%, at least 80% at least 85%, at least 90%, at least 94%, at least 95%, at least 96%, at least 97%, at least 98% or at least 99% amino acid sequence identity therewith.

In one embodiment, the polypeptide is a polypeptide variant having the sequence shown in SEQ ID NO: 8 or a polypeptide variant having at least at east 65% at least 70%, at least 75%, at least 78%, at least 80%, at least 85%, at least 90%, at least 94%, at least 95%, at least 96%, at least 97%, at least 98% or at least 99% amino acid sequence identity therewith.

In one aspect, the polypeptide sequence used in the present invention is in a purified form.

In one aspect, the polypeptide or protein for use in the present invention is in an isolated form.

A "variant" or "variants" refers to either polypeptides or nucleic acids. The term "variant" may be used interchangeably with the term "mutant". Variants include insertions, substitutions, transversions, truncations, and/or inversions at one or more locations in the amino acid or nucleotide sequence, respectively. The phrases "variant polypeptide", "polypeptide variant", "polypeptide", "variant" and "variant enzyme" mean a polypeptide/protein that has an amino acid sequence that either has or comprises the amino acid sequence of or is modified compared to the amino acid sequence of SEQ ID NO: 1, 2, 3, 4, 5, 6, 7, or 5. The variant polypeptides include a polypeptide having a certain percent, e.g., 60%, 65%, 66%, 68%, 70%, 72%, 74%, 76%, 78%, 80%, 85%, 90%, 91%, 92%, 93%, 94%, 95%, 96%, 97%, 98%, or 99%, of sequence identity with SEQ ID NO: 1, 2, 3, 4, 5, 6, 7, or 8. As used herein, "parent enzymes," "parent sequence," "parent polypeptide" mean enzymes and polypeptides from which any of the variant polypeptides are based, e.g., SEQ ID NO: 1 or 2. A "parent nucleic acid" means a nucleic acid sequence encoding the parent polypeptide. The signal sequence of a "variant" may be the same or may differ from the signal sequence of the wild-type *Ruminococcus lactaris* or *Blautia/Ruminococcus hansenii* or a *Bacillus* signal peptide or any signal sequence that will secrete the polypeptide. A variant may be expressed as a fusion protein containing a heterologous polypeptide. For example, the variant can comprise a signal peptide of another protein or a sequence designed to aid identification or purification of the expressed fusion protein, such as a His-Tag sequence.

To describe the various variants that are contemplated to be encompassed by the present disclosure, the following nomenclature will be adopted for ease of reference. Where the substitution includes a number and a letter, e.g., 592P, then this refers to {position according to the numbering system/substituted amino acid}. Accordingly, for example, the substitution of an amino acid to proline in position 592 is designated as 592P, Where the substitution includes a letter, a number, and a letter, e.g., D592P, then this refers to {original amino add/position according to the numbering system/substituted amino acid}. Accordingly, for example, the substitution of alanine with proline in position 592 is designated as A592P.

Where two or more substitutions are possible at a particular position, this will be designated by contiguous letters, which may optionally be separated by slash marks "/", e.g., G303ED or G303E/D.

Position(s) and substitutions are listed with reference to either SEQ ID NO: 1 or SEQ ID NO: 2. Equivalent positions in another sequence may be found by aligning this sequence with either SEQ ID NO: 1 or SEQ ID NO: 2 to find an alignment with the highest percent identity and thereafter determining which amino acid aligns to correspond with an amino acid of a specific position of either SEQ ID NO: 1 or SEQ ID NO: 2. Such alignment and use of one sequence as a first reference is simply a matter of routine for one of ordinary skill in the art.

"Variant nucleic acids" can include sequences that are complementary to sequences that are capable of hybridizing to the nucleotide sequences presented herein, in particular to SEQ ID NO:10-11. For example, a variant sequence is complementary to sequences capable of hybridizing under stringent conditions, e.g., 50° C. and 0.2×SSC (1×SSC=0.15 M NaCl, 0.015 M sodium citrate, pH 7.0), to the nucleotide sequences presented herein, in particular to SEQ ID NO: 10-11. More particularly, the term variant encompasses sequences that are complementary to sequences that are capable of hybridizing under highly stringent conditions, e.g., 65° C. and 0.1×SSC, to the nucleotide sequences presented herein, in particular to SEQ ID NO: 10-11. The melting point (Tm) of a variant nucleic acid may be about 1, 2, or 3° C. lower than the Tm of the wild-type nucleic acid.

In one aspect, the present invention relates to isolated polypeptides having transgalactosylating activity as stated above which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with i) the nucleic acid sequence comprised in SEQ ID NO: 10 encoding the mature polypeptide of SEQ ID NO: 1; the cDNA sequence of i) or iii) the complementary strand of i) or ii) or with i) the nucleic acid sequence comprised in SEQ ID NO: 11 encoding the mature polypeptide of SEQ ID NO: 2; ii) the cDNA sequence of i) or iii) the complementary strand of i) or ii); (J. Sambrook, E. F. Fritsch, and T. Maniatis, 1989, *Molecular Cloning, A Laboratory Manual,* 2d edition, Cold Spring Harbor, N.Y.). A subsequence of SEQ ID NO: 10 or 11 contains at least 100 contiguous nucleotides or preferably at least 200 contiguous nucleotides. Moreover, the subsequence may encode a polypeptide fragment which has lactase activity.

The nucleotide sequence of SEQ ID NO: 10 or 11 or a subsequence thereof, as well as the amino acid sequence of SEQ ID NO: 1 or 2 or a fragment thereof, may be used to design a nucleic acid probe to identify and done DNA encoding polypeptides having transgalactosylase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}$P, $^{3}$H, $^{33}$S, biotin, or avidin). Such probes are encompassed by the present invention.

A genomic DNA library prepared from such other organisms may, therefore, be screened for DNA which hybridizes with the probes described above and which encodes a polypeptide having lactase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 10 or 11 or a subsequence thereof, the carrier material is used in a Southern blot.

For purposes of the present invention, hybridization indicates that the nucleotide sequence hybridizes to a labelled nucleic acid probe corresponding to the nucleotide sequence shown in SEQ ID NO: 10 or 11, its complementary strand, or a subsequence thereof, under very low to very high stringency conditions. Molecules to which the nucleic acid probe hybridizes under these conditions can be detected using X-ray film.

In a preferred aspect, the nucleic acid probe is nucleotides 175 to 2011 or nucleotides 198 to 2040 of SEQ ID NO: 10 or SEQ ID NO: 11 respectively. In another preferred aspect, the nucleic acid probe is a polynucleotide sequence which encodes the polypeptide of SEQ ID NO: 1 or SEQ ID NO: 2, or a subsequence thereof. In another preferred aspect, the nucleic acid probe is SEQ ID NO: 10 or SEQ ID NO: 11. In another preferred aspect, the nucleic acid probe is the mature polypeptide coding region of SEQ ID NO: 10 or SEQ ID NO: 11.

For long probes of at least 100 nucleotides in length, very low to very high stringency conditions are defined as prehybridization and hybridization at 42° C. in 5×SSPE, 0.3% SDS, 200 g/ml sheared and denatured salmon sperm DNA, and either 25% formamide for very low and low stringencies, 35% formamide for medium and medium-high stringencies, or 50% formamide for high and very high stringencies, following standard Southern blotting procedures for 1.2 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

In a particular embodiment, the wash is conducted using 0.2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency). In another particular embodiment, the wash is conducted using 0.1×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

Under salt-containing hybridization conditions, the effective $T_m$ is what controls the degree of identity required between the probe and the filter bound DNA for successful hybridization. The effective $T_m$ may be determined using the formula below to determine the degree of identity required for two DNAs to hybridize under various stringency conditions.

$$\text{Effective } T_m = 81.5 + 16.6(\log M[Na^+]) + 0.41(\% G + C) - 0.72(\% \text{ formamide})$$

(See www.ndsu.nodak.edu/instruct/mcclean/plsc731/dna/dna6.htm)

The G+C content of SEQ ID NO: 10 is 42% and the G+C content of SEQ ID NO: 11 is 44%. For medium stringency, the formamide is 35% and the Na⁺ concentration for 5×SSPE is 0.75 M.

Another relevant relationship is that a 1% mismatch of two DNAs lowers the $T_m$ by 1.4° C. To determine the degree of identity required for two DNAs to hybridize under medium stringency conditions at 42° C., the following formula is used:

% Homology=100−[(Effective $T_m$−Hybridization Temperature)/1.4]

(See www.ndsu.nodak.edu/instruct/mcclean/plsc731/dna/dna6.htm)

The variant nucleic acids include a polynucleotide having a certain percent, e.g., 60%, 65%, 70%, 75%, 50%, 85%, 90%, 95%, or 99%, of sequence identity with the nucleic acid encoding SEQ ID NO: 1 or 2. In one aspect, a nucleic acid capable of encoding a polypeptide as disclosed herein, is provided. In a further aspect, the herein disclosed nucleic acid has a nucleic acid sequence which is at least 60%, such as at least 65%, such as at least 70%, such as at least 75%, such as at least 80%, such as at least 85%, such as at least 90%, such as at least 95%, such as at least 99% identical SEQ ID NO: 10 or 11.

In one aspect, the polypeptides disclosed herein comprises an amino acid sequence having at least 66% sequence identity to the amino acid sequence of the mature polypeptide encoded by the nucleotide sequence encoding the transgalatosylase contained in DSM accession no: 20583. In one aspect, the polypeptides disclosed herein comprises an amino acid sequence having at least 66% sequence identity to the amino acid sequence of the mature polypeptide encoded by the nucleotide sequence encoding the transgalatosylase contained in ATCC accession no: 29176. All considerations and limitations relating to sequence identities and functionality discussed in terms of the SEQ ID NO: 1 or 2 apply mutatis mutandis to sequence identities and functionality of these polypeptides and nucleotides.

As used herein, the term "expression" refers to the process by which a polypeptide is produced based on the nucleic acid sequence of a gene. The process includes both transcription and translation.

As used herein, "polypeptide" is used interchangeably with the terms "amino acid sequence", "enzyme", "peptide" and/or "protein". As used herein, "nucleotide sequence" or "nucleic add sequence" refers to an oligonucleotide sequence or polynucleotide sequence and variants, homologues, fragments and derivatives thereof. The nucleotide sequence may be of genomic, synthetic or recombinant origin and may be double-stranded or single-stranded, whether representing the sense or anti-sense strand. As used herein, the term "nucleotide sequence" includes genomic DNA, cDNA, synthetic DNA, and RNA.

"Homologue" means an entity having a certain degree of identity or "homology" with the subject amino acid sequences and the subject nucleotide sequences. In one aspect, the subject amino acid sequence is SEQ ID NO: 1-8, and the subject nucleotide sequence preferably is SEQ ID NO: 10-11.

A "homologous sequence" includes a polynucleotide or a polypeptide having a certain percent, e.g., 80%, 85%, 90%, 95%, or 99%, of sequence identity with another sequence. Percent identity means that, when aligned, that percentage of bases or amino acid residues are the same when comparing the two sequences. Amino acid sequences are not identical, where an amino acid is substituted, deleted, or added compared to the subject sequence. The percent sequence identity typically is measured with respect to the mature sequence of the subject protein, i.e., following removal of a signal sequence, for example, Typically, homologues will comprise the same active site residues as the subject amino acid sequence. Homologues also retain enzymatic activity, although the homologue may have different enzymatic properties than the wild-type As used herein, "hybridization" includes the process by which a strand of nucleic acid joins with a complementary strand through base pairing, as well as the process of amplification as carried out in polymerase chain reaction (PCR) technologies. The variant nucleic acid may exist as single- or double-stranded DNA or RNA, an RNA/DNA heteroduplex or an RNA/DNA copolymer. As used herein, "copolymer" refers to a single nucleic acid strand that comprises both ribonucieotides and deoxyribonucleotides. The variant nucleic acid may be codon-optimized to further increase expression.

As used herein, a "synthetic" compound is produced by in vitro chemical or enzymatic synthesis. It includes, but is not limited to, variant nucleic acids made with optimal codon usage for host organisms, such as a yeast cell host or other expression hosts of choice.

As used herein, "transformed cell" includes cells, including both bacterial and fungal cells, which have been transformed by use of recombinant DNA techniques. Transformation typically occurs by insertion of one or more nucleotide sequences into a cell. The inserted nucleotide sequence may be a heterologous nucleotide sequence, i.e., is a sequence that is not natural to the cell that is to be transformed, such as a fusion protein.

As used herein, "operably linked" means that the described components are in a relationship permitting them to function in their intended manner. For example, a regulatory sequence operably linked to a coding sequence is ligated in such a way that expression of the coding sequence is achieved under condition compatible with the control sequences.

As used herein, the term "fragment" is defined as a polypeptide having one or more (several) amino acids deleted from the amino and/or carboxyl terminus for example of the polypeptide of SEQ ID NO:12 or 13; wherein the fragment has transgalactosylating activity.

In one aspect, the term "polypeptide fragment" is defined herein as a polypeptide having one or more (several) amino acids deleted from the amino and/or carboxyl terminus of the polypeptide of SEQ ID NO:1 or 2; wherein the fragment has transgalactosylating activity.

In one aspect, a fragment contains at least 500, 700, 900 or 1000 amino acid residues. In one aspect, a fragment contains at the most 1250, 1200, 1180, 1170, 1150 or 1125 amino acid residues.

In a further aspect, the length of the polypeptide disclosed herein is 500 to 1250 amino acids. In a further aspect, the length of the polypeptide variant is 500 to 1200 amino acids. In a further aspect, the length of the polypeptide variant is 700 to 1170 amino acids. In a further aspect, the length of the polypeptide variant is 900 to 1180 amino acids. In a further aspect, the length of the polypeptide variant is 900 to 1150 amino acids. In a further aspect, the length of the polypeptide variant is 1000 to 1125 amino acids.

In one aspect, a plasmid comprising a nucleic acid as described herein, is provided.

In one aspect, an expression vector comprising a nucleic acid as described herein, or capable of expressing a polypeptide as described herein, is provided.

In a further aspect, a host cell comprising, preferably transformed with, a plasmid as described herein or an expression vector as described herein, is provided.

In a further aspect, a cell capable of expressing a polypeptide as described herein, is provided.

In one aspect, the host cell as described herein, or the cell as described herein is a bacterial, fungal or yeast cell.

In a further aspect, the host cell is selected from the group consisting of *Ruminococcus, Bifidobacterium, Lactococcus, Lactobacillus, Streptococcus, Leuconostoc, Escherichia, Bacillus, Streptomyces, Saccharomyces, Kluyveromyces, Candida, Torula, Torulopsis* and *Aspergillus*.

In a further aspect, the host cell is selected from the group consisting of *Ruminococcus hansenii, Bifidobacterium breve, Bifidobacterium longum, Bifidobacterium infantis, Bifidobacterium bifidum* and *Lactococcus lactis*.

In a further aspect, a method of expressing a polypeptide as described herein comprises obtaining a host cell or a cell as described herein and expressing the polypeptide from the cell or host cell, and optionally purifying the polypeptide.

Polypeptide Variants of SEQ ID NO: 1 or SEQ ID NO:2

In one aspect, a variant of SEQ ID NO:1 or 2 having a substitution at one or more positions which effects an altered property such as improved transgalactosylation, relative to SEQ ID NO: 1 or 2, is provided. Such variant polypeptides are also referred to in this document for convenience as "variant polypeptide", "polypeptide variant" or "variant". In one aspect, the polypeptides as defined herein have an improved transgalactosylating activity as compared to the polypeptide of SEQ ID NO: 1 or 2. In another aspect, the polypeptides as defined herein have an improved reaction velocity as compared to the polypeptide of SEQ ID No: 1 or 2.

In one aspect, the polypeptides and variants as defined herein exhibit enzyme activity. In one aspect, the polypeptides and the variant polypeptides described herein comprise transgalactosylation activity.

In one aspect, the ratio of transgalactosylating activity:β-galactosidase activity is at least 2.5, such as at least 3, such as at least 4, such as at least 5, such as at least 6, such as at least 7, such as at least 8, such as at least 9, such as at least 10, such as at least 11, or such as at least 12 after 30 min. reaction.

In one aspect, the polypeptides and the variants as defined herein are derivable from microbial sources, in particular from a filamentous fungus or yeast, or from a bacterium. The enzyme may, e.g., be derived from a strain of *Agaricus*, e.g. *A. bisporus; Ascovaginospora; Aspergillus*, e.g. *A. niger, A. awamori, A. foetidus, A. japonicus, A. oryzae; Candida; Chaetomium; Chaetotomastia; Dictyostelium*, e.g. *D. discoideum; Kluveromyces*, e.g. *K. fragilis, K. lactis; Mucor*, e.g. *M. javanicus, M. mucedo, M. subtilissimus; Neurospora*, e.g. *N. crassa; Rhizomucor*, e.g. *R. pusillus; Rhizopus*, e.g. *R. arrhizus, R. japonicus, R. stolonifer; Sclerotinia*, e.g. *S. libertiana; Torula; Torulopsis; Trichophyton*, e.g. *T. rubrum; Whetzelinia*, e.g. *W. sclerotiorum; Bacillus*, e.g. *B. coagulans, B. circulans, B. megaterium, B. novalis, B. subtilis, B. pumilus, B. stearothermophilus, B. thuringiensis; Bifidobacterium*, e.g. *B. Iongum, B. bifidum, B. animalis; Chryseobacterium; Citrobacter*, e.g. *C. freundii; Clostridium*, e.g. *C. perfringens; Diplodia*, e.g. *D. gossypina; Enterobacter*, e.g. *E. aerogenes, E. cloacae Edwardsiella, E. tarda; Erwinia*, e.g. *E. herbicola; Escherichia*, e.g. *E. coli; Klebsiella*, e.g. *K. pneumoniae; Miriococcum; Myrothesium; Mucor; Neurospora*, e.g. *N. crassa; Proteus*, e.g. *P. vulgaris; Providencia*, e.g. *P. stuartii; Pycnoporus*, e.g. *Pycnoporus cinnabarinus, Pycnoporus sanguineus; Ruminococcus*, e.g. *R. torques; Salmonella*, e.g. *S. typhimurium; Serratia*, e.g. *S. liquefasciens, S. marcescens; Shigella*, e.g. *S. flexneri; Streptomyces*, e.g. *S. antibioticus, S. castaneoglobisporus, S. violeceoruber; Trametes; Trichoderma* e.g. *T. reesei, T. viride; Yersinia* e.g. *Y. enterocolitica*.

An isolated and/or purified polypeptide comprising a polypeptide or a variant polypeptide as defined herein is provided. In one embodiment, the variant polypeptide is a mature form of the polypeptide (SEQ ID NO: 1 or 2). In one aspect, the variants include a C-terminal domain.

In one aspect, a variant polypeptide as defined herein includes variants wherein between one and about 25 amino acid residues have been added or deleted with respect to SEQ ID NO: 1 or SEQ ID NO: 2. In one aspect, the variant has the amino acid sequence of SEQ ID NO: 1 or SEQ ID NO: 2, wherein any number between one and about 25 amino acids have been substituted. In a further aspect, the variant has the amino acid sequence of SEQ ID NO: 1 or SEQ ID NO: 2, wherein any number between three and twelve amino acids has been substituted. In a further aspect, the variant has the amino acid sequence of SEQ ID NO: 1 or SEQ ID NO: 2, wherein any number between five and nine amino acids has been substituted.

In one aspect, at least two, in another aspect at least three, and yet in another aspect at least five amino acids of SEQ ID NO: 1 or SEQ ID NO: 2 have been substituted.

In one aspect, the herein disclosed polypeptide(s) has the sequence of SEQ ID NO: 1 or 2.

In one aspect, the herein disclosed polypeptide(s) has the sequence of SEQ ID NO: 1 or 2, wherein the 10, such as 9, such as 8, such as 7, such as 6, such 5, such as 4, such as 3, such as 2, such as 1 amino acid in the N-terminal end are substituted and/or deleted.

In a further aspect, the length of the polypeptide variant is 500 to 1250 amino acids. In a further aspect, the length of the polypeptide variant is 500 to 1200 amino acids. In a further aspect, the length of the polypeptide variant is 700 to 1170 amino acids. In a further aspect, the length of the polypeptide variant is 900 to 1180 amino acids. In a further aspect, the length of the polypeptide variant is 900 to 1150 amino acids. In a further aspect, the length of the polypeptide variant is 1000 to 1125 amino acids.

Polypeptide Characterization

Enzymes and enzyme variants thereof can be characterized by their nucleic acid and primary polypeptide sequences, by three dimensional structural modeling, and/or by their specific activity. Additional characteristics of the polypeptide or polypeptide variants as defined herein include stability, pH range, oxidation stability, and thermostability, for example. Levels of expression and enzyme activity can be assessed using standard assays known to the artisan skilled in this field. In another aspect, variants demonstrate improved performance characteristics relative to the polypeptide with SEQ ID NO: 1 or 2, such as improved stability at high temperatures, e.g., 65-85° C.

An expression characteristic means an altered level of expression of the variant, when the variant is produced in a particular host cell. Expression generally relates to the amount of active variant that is recoverable from a fermentation broth using standard techniques known in this art over a given amount of time. Expression also can relate to the amount or rate of variant produced within the host cell or secreted by the host cell. Expression also can relate to the rate of translation of the mRNA encoding the variant polypeptide.

A nucleic acid complementary to a nucleic acid encoding any of the polypeptide variants as defined herein set forth herein is provided. Additionally, a nucleic acid capable of hybridizing to the complement is provided. In another embodiment, the sequence for use in the methods and compositions described here is a synthetic sequence. It includes, but is not limited to, sequences made with optimal codon usage for expression in host organisms, such as yeast.

The polypeptide variants as provided herein may be produced synthetically or through recombinant expression in a host cell, according to procedures well known in the art. In one aspect, the herein disclosed polypeptide(s) is recombinant polypeptide(s). The expressed polypeptide variant as defined herein optionally is isolated prior to use.

In another embodiment, the polypeptide variant as defined herein is purified following expression. Methods of genetic modification and recombinant production of polypeptide variants are described, for example, in U.S. Pat. Nos. 7,371,552, 7,166,453; 6,890,572; and 6,667,065; and U.S. Published Application Nos. 2007/0141693; 2007/0072270; 2007/0020731; 2007/0020727; 2006/0073583; 2006/0019347; 2006/0018997; 2006/0008890; 2006/0008888; and 2005/0137111. The relevant teachings of these disclosures, including polypeptide-encoding polynucleotide sequences, primers, vectors, selection methods, host cells, purification and reconstitution of expressed polypeptide variants, and characterization of polypeptide variants as defined herein, including useful buffers, pH ranges, $Ca^{2+}$ concentrations, substrate concentrations and enzyme concentrations for enzymatic assays, are herein incorporated by reference.

In another embodiment, suitable host cells include a Gram positive bacterium selected from the group consisting of Bacillus subtilis, B. licheniformis, B. lentus, B. brevis, B. stearothermophilus, B. alkalophilus, B. amyloliquefaciens, B. coagulans, B. circulans, B. lautus, B. thuringiensis, Streptomyces lividans, or S. murinus; or a Gram negative bacterium, wherein said Gram negative bacterium is Escherichia coil or a Pseudomonas species. In one aspect, the host cell is a B. subtilus or B. lichenformis. In one embodiment, the host cell is B. subtilis and the expressed protein is engineered to comprise a B. subtilis signal sequence, as set forth in further detail below. In one aspect, the host cell expresses the polynucleotide as set out in the claims.

In some embodiments, a host cell is genetically engineered to express a polypeptide variant as defined herein with an amino acid sequence having at least about 66%, 68%, 70%, 72%, 74%, 78%, 80%, 85%, 90%, 91%, 92%, 93%, 94%, 95%, 96%, 97%, 98%, 99%, 100% identity with the polypeptide of SEQ ID NO:1 or 2, in some embodiments, the polynucleotide encoding a polypeptide variant as defined herein will have a nucleic acid sequence encoding the protein of SEQ ID NO; 1 or a nucleic acid sequence having at least about 66%, 68%, 70%, 72%, 74%, 78%, 80%, 85%, 90%, 95%, 96%, 97%, 98%, 99% or 100% sequence identity with a nucleic acid encoding the protein of SEQ ID NO: 1 or 2. In one embodiment, the nucleic acid sequence has at least about 60%, 66%, 68%, 70%, 72%, 74%, 78%, 80% 85%, 90%, 95%, 96%, 97%, 98% or 99% sequence identity to the nucleic acid of SEQ ID NO: 10-11.

Vectors

In one aspect, the invention relates to a vector comprising a polynucleotide. In one aspect, a bacterial cell comprises the vector. In some embodiments, a DNA construct comprising a nucleic acid encoding a variant is transferred to a host cell in an expression vector that comprises regulatory sequences operably linked to an encoding sequence. The vector may be any vector that can be integrated into a fungal host cell genome and replicated when introduced into the host cell. The FGSC Catalogue of Strains, University of Missouri, lists suitable vectors. Additional examples of suitable expression and/or integration vectors are provided in Sambrook et al., MOLECULAR CLONING: A LABORATORY MANUAL, $3^{rd}$ ed., Cold Spring Harbor Laboratory Press, Cold Spring Harbor, N.Y. (2001); Bennett et al., MORE GENE MANIPULATIONS IN FUNGI, Academic Press, San Diego (1991), pp. 396-428; and U.S. Pat. No. 5,874,276. Exemplary vectors include pFB6, pBR322, PUC18, pUC100 and pENTR/D, pDON™201, pDONR™221, pENTR™, pGEW®3Z and pGEM®4Z. Exemplary for use in bacterial cells include pBR322 and pUC19, which permit replication in E. coli, and pE194, for example, which permits replication in Bacillus.

In some embodiments, a nucleic acid encoding a variant is operably linked to a suitable promoter, which allows transcription in the host cell. The promoter may be derived from genes encoding proteins either homologous or heterologous to the host cell. Suitable non-limiting examples of promoters include cbh1, cbh2, egl1, and egl2 promoters. In one embodiment, the promoter is one that is native to the host cell. For example, when P. saccharophila is the host, the promoter is a native P. saccharophila promoter. An "inducible promoter" is a promoter that is active under environmental or developmental regulation. In another embodiment, the promoter is one that is heterologous to the host cell.

In some embodiments, the coding sequence is operably linked to a DNA sequence encoding a signal sequence. A representative signal peptide is SEQ ID NO; 9 which is the native signal sequence of the Bacillus subtilis aprE precursor. In other embodiments, the DNA encoding the signal sequence is replaced with a nucleotide sequence encoding a signal sequence from other extra-cellular Bacillus subtilis pre-cursors. In one embodiment, the polynucleotide that encodes the signal sequence is immediately upstream and in-frame of the polynucleotide that encodes the polypeptide. The signal sequence may be selected from the same species as the host cell.

In additional embodiments, a signal sequence and a promoter sequence comprising a DNA construct or vector to be introduced into a fungal host cell are derived from the same source. In some embodiments, the expression vector also includes a termination sequence. In one embodiment, the termination sequence and the promoter sequence are derived from the same source. In another embodiment, the termination sequence is homologous to the host cell.

In some embodiments, an expression vector includes a selectable marker. Examples of suitable selectable markers include those that confer resistance to antimicrobial agents, e.g., hygromycin or phleomycin. Nutritional selective markers also are suitable and include amdS, argB, and pyr4. In one embodiment, the selective marker is the amdS gene, which encodes the enzyme acetamidase; it allows transformed cells to grow on acetamide as a nitrogen source. The use of an A. nidulans amdS gene as a selective marker is described in Kelley et al., EMBO J. 4: 475-479 (1985) and Penttila et al., Gene 61: 155-164 (198).

A suitable expression vector comprising a DNA construct with a polynucleotide encoding a variant may be any vector that is capable of replicating autonomously in a given host organism or integrating into the DNA of the host. In some embodiments, the expression vector is a plasmid. In some embodiments, two types of expression vectors for obtaining expression of genes are contemplated. The first expression vector comprises DNA sequences in which the promoter, coding region, and terminator all originate from the gene to be expressed. In some embodiments, gene truncation is obtained by deleting undesired DNA sequences to leave the domain to be expressed under control of its own transcriptional and translational regulatory sequences. The second type of expression vector is preassembled and contains sequences required for high-level transcription and a selectable marker.

In some embodiments, the coding region for a gene or part thereof is inserted into this general-purpose expression vector, such that it is under the transcriptional control of the expression construct promoter and terminator sequences. In some embodiments, genes or part thereof are inserted downstream of the strong cbh1 promoter.

Transformation, Expression and Culture of Host Cells

Introduction of a DNA construct or vector into a host cell includes techniques such as transformation; electroporation; nuclear microinjection; transduction; transfection, e.g., lipofection mediated and DEAE-Dextrin mediated transfection; incubation with calcium phosphate DNA precipitate; high velocity bombardment with DNA-coated microprojectiles; and protoplast fusion. General transformation techniques are known in the art. See, e.g., Ausubel et al. (1987), supra, chapter 9; Sambrook et al. (2001), supra; and Campbell at al., *Curr. Genet.* 16: 53-56 (1989). The expression of heterologous protein in *Trichoderma* is described, for example, in U.S. Pat. No. 6,022,725; U.S. Pat. No. 6,268,328; Harkki at al., *Enzyme Microb. Technol.* 13: 227-233 (1991); Harkki et al., *BioTechnol.* 7: 596-603 (1989); EP 244,234; and EP 215,594. In one embodiment, genetically stable transformants are constructed with vector systems whereby the nucleic acid encoding a variant is stably integrated into a host cell chromosome. Transformants are then purified by known techniques.

In one non-limiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on solid non-selective medium, e.g., a medium that lacks acetamide, harvesting spores from this culture medium and determining the percentage of these spores that subsequently germinate and grow on selective medium containing acetamide. Other methods known in the art may be used to select transformants.

Identification of Activity

To evaluate the expression of a variant in a host cell, assays can measure the expressed protein, corresponding mRNA, or β-galactosidase activity. For example, suitable assays include Northern and Southern blotting, RT-PCR (reverse transcriptase polymerase chain reaction), and in situ hybridization, using an appropriately labeled hybridizing probe. Suitable assays also include measuring activity in a sample. Suitable assays of the activity of the variant include, but are not limited to, ONPG based assays or determining glucose in reaction mixtures such for example described in the examples herein.

Methods for Purifying Herein Disclosed Polypeptides

In general, a variant produced in cell culture is secreted into the medium and may be purified or isolated, e.g., by removing unwanted components from the cell culture medium. In some cases, a variant may be recovered from a cell lysate. In such cases, the enzyme is purified from the cells in which it was produced using techniques routinely employed by those of skill in the art. Examples include, but are not limited to, affinity chromatography, ion-exchange chromatographic methods, including high resolution ion-exchange, hydrophobic interaction chromatography, two-phase partitioning, ethanol precipitation, reverse phase HPLC, chromatography on silica or on a cation-exchange resin, such as DEAF, chromatofocusing, SDS-PAGE, ammonium sulfate precipitation, and gel filtration using Sephadex G-75, for example. Depending on the intended use the herein disclosed polypeptide(s) may for example be either freeze-dried or prepared in a solution. In one aspect, the herein disclosed polypeptide(s) is freeze-dried form. In another aspect, the herein disclosed polypeptide(s) is in solution.

Methods for Immobilising and Formulation of the Herein Disclosed Polypeptides

The polypeptide compositions may be prepared in accordance with methods known in the art and may be in the form of a liquid or a dry composition. For instance, the polypeptide composition may be in the form of a granulate or a microaranulate. The polypeptide to be included in the composition may be stabilized in accordance with methods known in the art.

The enzyme preparation, such as in the form of a food ingredient prepared according to the present invention, may be in the form of a solution or as a solid—depending on the use and/or the mode of application and/or the mode of administration. The solid form can be either as a dried enzyme powder or as a granulated enzyme.

Examples of dry enzyme formulations include spray dried products, mixer granulation products, layered products such as fluid bed granules, extruded or pelletized granules, prilled products, or lyophilised products.

The enzyme preparation, such as in the form of a food ingredient prepared according to the present invention, may be in the form of a solution or as a solid—depending on the use and/or the mode of application and/or the mode of administration. The solid form can be either as a dried enzyme powder or as a granulated enzyme.

In one aspect the invention provides an enzyme complex preparation comprising the enzyme complex according to the invention, an enzyme carrier and optionally a stabilizer and/or a preservative.

In yet a further aspect of the invention, the enzyme carrier is selected from the group consisting of glycerol or water.

In a further aspect, the preparation comprises a stabilizer. In one aspect, the stabilizer is selected from the group consisting of inorganic salts, polyols, sugars and combinations thereof. In one aspect, the stabilizer is an inorganic salt such as potassium chloride. In another aspect, the polyol is glycerol, propylene glycol, or sorbitol. In yet another aspect, the sugar is a small-molecule carbohydrate, in particular any of several sweet-tasting ones such as glucose, galactose, fructose and saccharose.

In yet at further aspect, the preparation comprises a preservative. In one aspect, the preservative is methyl paraben, propyl paraben, benzoate, sorbate or other food approved preservatives or a mixture thereof.

The method of the invention can be practiced with immobilized enzymes, e.g. an immobilized lactase or other galactooligosaccharide producing enzymes. The enzyme can be immobilized on any organic or inorganic support. Exemplary inorganic supports include alumina, celite, Dowex-1-chloride, glass beads and silica gel. Exemplary organic supports include DEAE-cellulose, alginate hydrogels or alginate beads or equivalents. In various aspects of the invention, immobilization of the lactase can be optimized by physical adsorption on to the inorganic support. Enzymes used to practice the invention can be immobilized in different media, including water, Tris-HCl buffer and phosphate buffered solution. The enzyme can be immobilized to any type of substrate, e.g. filters, fibers, columns, beads, colloids, gels, hydrogels, meshes and the like.

Use of the Herein Disclosed Polypeptides

In one aspect, a method for producing a dairy product by treating a milk-based substrate comprising lactose with a polypeptide as described herein is provided. In a further aspect, a method for producing a dairy product by treating a milk-based substrate comprising lactose with a polypeptide having a relative transgalactosylation activity above 60%, such as above 70%, such as above 75% after 15 min. reaction, is provided. In one aspect, the relative transgalactosylation activity is above 3 after 30 min. reaction. In a further aspect, the relative transgalactosylation activity is above 6 after 30 min. reaction. In yet a further aspect, the relative transgalactosylation activity is above 12 after 30 min. reaction. In one aspect, a method is provided, wherein the treatment with a polypeptide as described herein takes place at an optimal temperature for the activity of the enzyme. In a further aspect, the polypeptide is added to the milk-based substrate at a concentration of 0.01-1000 ppm. In yet a further aspect, the polypeptide is added to the milk-based substrate at a concentration of 0.1-100 ppm. In a further aspect, the polypeptide is added to the milk-based substrate at a concentration of 1-10 ppm. In one aspect, a method further comprising fermenting a substrate such as a dairy product with a microorganism, is provided. In a further aspect, the dairy product is yogurt. In a further aspect, the treatment with the polypeptide and the microorganism is performed essentially at the same time. In one aspect, the polypeptide and the microorganism are added to the milk-based substrate essentially at the same time.

In one aspect, a composition preferably a food composition, more preferably a dairy product comprising a cell or a polypeptide as described herein, is provided.

In one aspect, a dairy product comprising a cell or a polypeptide as described herein, is provided. In one aspect, the polypeptide as defined herein is added in a concentration of 0.01-1000 ppm. In one aspect, a dairy product comprising an inactivated polypeptide as defined herein, is provided. In one aspect, a dairy product comprising an inactivated polypeptide as defined herein in a concentration of 0.01-1000 ppm, is provided. In one aspect, a dairy product comprising GOS formed in situ by a polypeptide as defined herein, is provided. In one aspect, a dairy product comprising a cell as defined herein, is provided.

A dairy product as described herein may be, e.g., skim milk, low fat milk, whole milk, cream, UHT milk, milk having an extended shelf life, a fermented milk product, cheese, yoghurt, butter, dairy spread, butter milk, acidified milk drink, sour cream, whey based drink, ice cream, condensed milk, dulce de leche or a flavoured milk drink. A dairy product may be manufactured by any method known in the art.

A dairy product may additionally comprise non-milk components, e.g. vegetable components such as, e.g., vegetable oil, vegetable protein, and/or vegetable carbohydrates. Dairy products may also comprise further additives such as, e.g., enzymes, flavouring agents, microbial cultures such as probiotic cultures, salts, sweeteners, sugars, acids, fruit, fruit juices, or any other component known in the art as a component of, or additive to, a dairy product.

In one embodiment of the invention, one or more milk components and/or milk fractions account for at east 50% (weight/weight), such as at least 70%, e.g., at least 80%, preferably at least 90%, of the dairy product.

In one embodiment of the invention, one or more milk-based substrates having been treated with an enzyme as defined herein having transgalactosylating activity account for at least 50% (weight/weight), such as at least 70%, e.g. at least 80%, preferably at least 90%, of the dairy product.

In one embodiment of the invention, the dairy product is a dairy product which is not enriched by addition of pre-produced galacto-oligosaccharides.

In one embodiment of the invention, the polypeptide-treated milk-based substrate is not dried before being used as an ingredient in the dairy product.

In one embodiment of the invention, the dairy product is ice cream. In the present context, ice cream may be any kind of ice cream such as full fat ice cream, low fat ice cream, or ice cream based on yoghurt or other fermented milk products. Ice cream may be manufactured by any method known in the art.

In one embodiment of the invention, the dairy product is milk or condensed milk.

In one embodiment of the invention, the dairy product is UHT milk, UHT milk in the context of the present invention is milk which has been subjected to a sterilization procedure which is intended to kill all microorganisms, including the bacterial spores. UHT (ultra high temperature) treatment may be, e.g., heat treatment for 30 seconds at 130° C., or heat treatment for one second at 145° C.

In one preferred embodiment of the invention, the dairy product is ESL milk. ESL milk in the present context is milk which has an extended shelf life due to microfiltration and/or heat treatment and which is able to stay fresh for at least 15 days, preferably for at least 20 days, on the store shelf at 2-5° C.

In another preferred embodiment of the invention, the dairy product is a fermented dairy product, e.g., yoghurt.

The microorganisms used for most fermented milk products are selected from the group of bacteria generally referred to as lactic acid bacteria. As used herein, the term "lactic add bacterium" designates a gram-positive, microaerophilic or anaerobic bacterium, which ferments sugars with the production of acids including lactic acid as the predominantly produced acid, acetic acid and propionic acid. The industrially most useful lactic, acid bacteria are found within the order "Lactobacillales" which includes *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp. and *Propionibacterium* spp. Additionally, lactic add producing bacteria belonging to the group of anaerobic bacteria, bifidobacteria, i.e. *Bifidobacterium* spp., which are frequently used as food cultures alone or in combination with lactic acid bacteria, are generally included in the group of lactic acid bacteria. Lactic acid bacteria are normally supplied to the dairy industry either as frozen or freeze-dried cultures for bulk starter propagation or as so-called "Direct Vat Set" (DVS) cultures, intended for direct inoculation into a fermentation vessel or vat for the production of a fermented dairy product. Such cultures are in general referred to as "starter cultures" or "starters".

Commonly used starter culture strains of lactic acid bacteria are generally divided into mesophilic organisms having optimum growth temperatures at about 30° C. and thermophilic organisms having optimum growth temperatures in the range of about 40 to about 45° C. Typical organisms belonging to the mesophilic group include *Lactococcus lactis, Lactococcus lactis* subsp. *cremoris, Leuconostoc mesenteroides* subsp. *cremoris, Pseudoleuconostoc mesenteroldes* subsp. *cremoris, Pediococcus pentosaceus, Lactococcus lactis* subsp. *lactis biovar. diacetylactis, Lactobacillus casei* subsp. *casei* and *Lactobacillus paracasei* subsp. *paracasei*. Thermophilic lactic acid bacterial species include as examples *Streptococcus thermophilus, Enterococcus faecium, Lactobacillus delbrueckii* subsp. *lactis, Lactobacillus helveticus, Lactobacillus delbrueckii* subsp. *bulgaricus* and *Lactobacillus acidophilus*, Also the anaerobic bacteria belonging to the genus *Bifidobacterium* including *Bifidobacterium bifidum, Bifidobacterium animalis* and *Bifidobacterium longum* are commonly used as dairy starter cultures and are generally included in the group of lactic acid bacteria. Additionally, species of *Propionibacteria* are used as dairy starter cultures, in particular in the manufacture of cheese. Additionally, organisms belonging to the *Brevibacterium* genus are commonly used as food starter cultures.

Another group of microbial starter cultures are fungal cultures, including yeast cultures and cultures of filamentous fungi, which are particularly used in the manufacture of certain types of cheese and beverage. Examples of fungi include *Penicillium roqueforti, Penicillium candidum, Geotrichum candidum, Torula kefir, Saccharomyces kefir* and *Saccharomyces cerevisiae.*

In one embodiment of the present invention, the microorganism used for fermentation of the milk-based substrate is *Lactobacillus casei* or a mixture of *Streptococcus thermophilus* and *Lactobacillus delbrueckii* subsp. *bulgaricus.*

Fermentation processes to be used in a method of the present invention are well known and the person of skill in the art will know how to select suitable process conditions, such as temperature, oxygen, amount and characteristics of microorganism's, additives such as e.g. carbohydrates, flavours, minerals, enzymes, and process time. Obviously, fermentation conditions are selected so as to support the achievement of the present invention. As a result of fermentation, pH of the milk-based substrate will be lowered. The pH of a fermented dairy product of the invention may be, e.g., in the range 3.5-6, such as in the range 3.5-5, preferably in the range 3.8-4.8.

In one aspect, a method of using the polypeptides or using any one or more of the above mentioned cell types for producing oligosaccharides, is provided. The oligosaccharides comprise, but are not limited to fructooligo-saccharides, galacto-oligosaccharides, isomalto-oligosaccharides, malto-oligosaccharides, lactosucrose and xylo-oligosaccharides.

In one embodiment of the invention, the oligosaccharides are produced by incubating the cell expressing the polypeptide in a medium that comprises a disaccharide substrate such as for example lactulose, trehalose, rhamnose, maltose, sucrose, lactose, or cellobiose. The incubation is carried out under conditions where oligosaccarides are produced. The cells may be part of a product selected from the group consisting of yoghurt, cheese, fermented milk products, dietary supplements, and probiotic comestible products. Alternatively, the oligosaccharides can be recovered and subsequently be added to the product of interest before or after its preparation.

In one aspect, the use of a herein disclosed cell for producing a product selected from the group consisting of yoghurt, cheese, fermented milk product, dietary supplement and probiotic comestible product, is provided.

In one aspect, the polypeptides described herein may be used to prepare cheese products and in methods for making the cheese products. Cheese products may e.g. be selected from the group consisting of cream cheese, cottage cheese, and process cheese. By adding polypeptides the cheeses may contain significantly increased levels of galacto-oligosaccharides and reduced levels of lactose. In one aspect, the lactose levels in the final cheese product may be reduced by at least about 25 percent, preferably at least about 50 percent, and more preferably at least about 75 percent. The polypeptides may be used to reduce Lactose in cheese products to less than about 1 gram per serving, an amount that can be tolerated by most lactose-intolerant individuals.

The cheese products provided herein are nutritionally-enhanced cheese products having increased soluble fiber content, reduced caloric content, excellent organoleptic properties, improved texture, and flavor. Further, the polypeptides described herein may reduce the glycemic index of the cheese products because GOS are more slowly absorbed than lactose or its hydrolysis products. Finally, the polypeptides may reduce the cost of production of cheese products, particularly cream cheese products, because GOS surprisingly provide improved texture to the cream cheese product, thus permitting reduced use of stabilizers, or by allowing for increased moisture content without syneresis.

In a further aspect, a composition comprising a polypeptide as described herein and a carbohydrate substrate, is provided. In a further aspect, the carbohydrate substrate is a disaccharide. In a further aspect, the disaccharide is for example lactulose, trehalose, rhamnose, maltose, sucrose, lactose or cellobiose. In yet a further aspect, the carbohydrate substrate is lactose. The composition is prepared such that oligosaccarides are produced. The polypeptide as described herein may be part of a product selected from the group consisting of yoghurt, cheese, fermented milk products, dietary supplements, and probiotic comestible products. In one aspect, a composition comprising a polypeptide as described herein and a stabilizer, is provided. Examples of stabilizers is e.g., a polyol such as, e.g., glycerol or propylene glycol, a sugar or a sugar alcohol, lactic acid, boric add, or a boric acid derivative (e.g., an aromatic borate ester).

In one aspect, the use of a transgalactosylating polypeptide as disclosed herein or a cell as disclosed herein, for producing galacto-oligosaccharides, is provided. In one aspect, the use of a transgalactosylating polypeptide as disclosed herein or a cell as disclosed herein, for producing galacto-oligosaccharides to be part of a product selected from the group consisting of yoghurt, cheese, fermented dairy products, dietary supplements and probiotic comestible products, is provided. In one aspect, the product is yoghurt, cheese, or fermented dairy products. In one aspect, the use of a transgalactosylating polypeptide as disclosed herein or a cell as disclosed herein, for producing galacto-oligosaccharides to enhance the growth of *Bifidobacterium*, is provided. In one aspect, the use of a transgalactosylating polypeptide as disclosed herein or a cell as disclosed herein, for producing galacto-oligosaccharides to enhance the growth of *Bifidobacterium* in a mixed culture fermentation, is provided.

In one aspect, a process for producing a transgalactosylating polypeptide as disclosed herein, comprising culturing a cell as disclosed herein in a suitable culture medium under conditions permitting expression of said polypeptide, and recovering the resulting polypeptide from the culture, is provided. A process for producing galacto-oligosaccharides, comprising contacting of an polypeptide of as disclosed herein or a cell as disclosed herein with a milk-based solution comprising lactose, is provided.

Addition of oligosaccharides may enhance growth of either *Bifidobacterium* alone or of *Bifidobacterium* in a mixed culture.

The treatment of milk products with enzymes that converts lactose into monosaccharides or GOS have several advantages. First the products can be consumed by people with lactose intolerance that would otherwise exhibit symptoms such as flatulence and diarrhea. Secondly, dairy products treated with lactase will have a higher sweetness than similar untreated products due to the higher perceived sweetness of glucose and galactose compared to lactose. This effect is particularly interesting for applications such as yoghurt and ice-cream where high sweetness of the end product is desired and this allows for a net reduction of carbohydrates in the consumed product. Thirdly, in ice-cream production a phenomenon termed sandiness is often seen, where the lactose molecules crystallizes due to the relative low solubility of the lactose. When lactose is converted into monosaccharides or GOS the mouth feeling of the ice-cream is much improved over the non-treated products. The presence of a sandy feeling due to lactose crystallization can be eliminated and the raw material costs can be decreased by replacement of skimmed milk powder by whey powder. The main effects of the enzymatic treatment were increased sweetness.

In one aspect, the transgalactosylating polypeptide(s) as disclosed herein may be used together with other enzymes such as proteases such as chymosin or rennin, lipases such as phospholipases, amylases, transferases, and lactases. In one aspect, the transgalactosylating polypeptide(s) as disclosed herein may be used together with lactase. This may especially be useful when there is a desire to reduce residual lactose after treatment with the transgalactosylating polypeptide(s) as disclosed herein especially at low lactose levels. A lactase in the context of the present invention is any glycoside hydrolase having the ability to hydrolyse the disaccharide lactose into constituent galactose and glucose monomers. The group of lactases comprises but is not limited to enzymes assigned to subclass EC 3.2.1.108. Enzymes assigned to other subclasses, such as, e.g., EC 3.2.1.23, may also be lactases the context of the present invention. A lactase in the context of the invention may have other activities than the lactose hydrolysing activity, such as for example a transgalactosylating activity. In the context of the invention, the lactose hydrolysing activity of the lactase may be referred to as its lactase activity or its beta-galactosidase activity. Enzymes having lactase activity to be used in a method of the present invention may be of animal, of plant or of microbial origin. Preferred enzymes are obtained from microbial sources, in particular from a filamentous fungus or yeast, or from a bacterium. The enzyme may, e.g. be derived from a strain of *Agaricus*, e.g. *A. bisporus*; *Ascovaginospora*; *Aspergillus*, e.g. *A. niger, A. awamori, A. foetidus, A. japonicus, A. oryzae*; *Candida*; *Chaetomium*; *Chaetotomastia*; *Dictyostelium* e.g. *D. discoideum*; *Kluveromyces*, e.g. *K. fragilis, K. lactis*; *Mucor*, e.g. *M. javanicus, M. mucedo, M. subtilissimus*; *Neurospora*, e.g. *N. crassa*; *Rhizomucor*, e.g. *R. pusillus*; *Rhizopus*, e.g. *R. arrhizus, R. japonicus, R. stolonifer*; *Sclerotinia*, e.g. *S. libertiana*; *Torula*; *Torulopsis*; *Trichophyton*, e.g. *T. rubrum*; *Whetzelinia*, e.g. *W. sclerotiorum*; *Bacillus*, e.g. *B. coagulans, B. circulans, B. megaterium, B. novalis, B. subtilis, B. pumilus, stearothermophilus, B. thuringiensis*; *Bifidobacterium* e.g. *B. longum, B. bifidum, B. animalis*; *Chryseobacterium*; *Citrobacter*, e.g. *C. freundii*; *Clostridium*, e.g. *C. perfringens*; *Diplodia*, e.g. *D. gossypiria*; *Enterobacter*, e.g. *E. aerogenes, E. cloacae Edwardsiella, E. tarda*; *Erwinia*, e.g. *E. herbicola*; *Escherichia*, e.g. *E. coli*; *Klebsiella*, e.g. *K. pneumoniae*; *Miriococcum*; *Myrothesium*; *Mucor*; *Neurospora*, e.g. *N. crassa*; *Proteus*, e.g. *P. vulgaris*; *Providencia*, e.g. *P. stuartii*; *Pycnoporus* e.g. *Pycnoporus cinnabarinus, Pycnoporus sanguineus*; *Ruminococcus*, e.g. *R. torques*; *Salmonella*, e.g. *S. typhimurium*; *Serratia*, e.g. *S. liquefasciens, S. marcescens*; *Shigella*, e.g. *S. flexneri*; *Streptomyces*, e.g. *S. antibioticus, S. castaneoglobisporus, S. violeceoruber*; *Trametes*; *Trichoderma*, e.g. *T. reesei, T. viride*; *Yersinia*, e.g. *Y. enterocolitica*. In one embodiment, the lactase is an intracellular component of microorganisms like *Kluyveromyces* and *Bacillus*. *Kluyveromyces*, especially *K. fragilis* and *K. lactis*, and other fungi such as those of the genera *Candida, Torula* and *Torulopsis*, are a common source of fungal lactases, whereas *B. coagulans* and *B. circulans* are well known sources for bacterial lactases. Several commercial lactase preparations derived from these organisms are available such as Lactozym® (available from Novozymes, Denmark), HA-Lactase (available from Chr. Hansen, Denmark) and Maxilact® (available from DSM, the Netherlands), all from *K. lactis*. All these lactases are so called neutral lactases having a pH optimum between pH 6 and pH 8. When such lactases are used in the production of, e.g. low-lactose yoghurt, the enzyme treatment will either have to be done in a separate step before fermentation or rather high enzyme dosages have to be used, because their activity drop as the pH decreases during fermentation. Also, these lactases are not suitable for hydrolysis of lactose in milk performed at high temperature, which would in some cases be beneficial in order to keep the microbial count low and thus ensure good milk quality.

In one embodiment, the enzyme is a lactase from a bacterium, e.g. from the family is Bifidobacteriaceae, such as from the genus *Bifidobacterium* such as the lactase described in WO 2009/071539.

Further aspects according to the invention:

Aspect 1. An isolated polypeptide having transgalactosylating activity selected from the group consisting of:
  a. a polypeptide comprising an amino acid sequence having at least 66% sequence identity to the amino acid sequence of the mature polypeptide of SEQ ID NO: 1,
  b. a polypeptide comprising an amino acid sequence having at least 66% sequence identity to the amine acid sequence of the mature polypeptide of SEQ ID NO: 2,
  c. a polypeptide encoded by a polynucleotide that hybridizes under at least low stringency conditions with i) the nucleic acid sequence comprised in SEQ ID NO: 10 encoding the mature polypeptide of SEQ ID NO: 1; ii) the cDNA sequence of i) or iii) the complementary strand of i) or ii);
  d. a polypeptide encoded by a polynucleotide that hybridizes under at least low stringency conditions with i) the nucleic acid sequence comprised in SEQ ID NO: 11 encoding the mature polypeptide of SEQ ID NO: 2; ii) the cDNA sequence of i) or iii) the complementary strand of i) or ii);
  e. a polypeptide comprising a conservative substitution, deletion and/or insertion of one or more amino acids of SEQ ID NO: 1,
  f. a polypeptide comprising a conservative substitution, deletion and/or insertion of one or more amino acids of SEQ ID NO: 2,
  g. a polypeptide encoded by a polynucleotide comprising a nucleotide sequence having at least 70% identity to the nucleotide sequence encoding for the mature polypeptide of SEQ ID NO: 1 or the nucleotide sequence comprised in SEQ ID NO:10 encoding a mature polypeptide,
  h. a polypeptide encoded by a polynucleotide comprising a nucleotide sequence having at least 70% identity to the nucleotide sequence encoding for the mature polypeptide of SEQ ID NO: 2 or the nucleotide sequence comprised in SEQ ID NO:11 encoding a mature polypeptide,
  i. a polypeptide comprising an amino acid sequence having at least 66% sequence identity to the amino acid sequence of the mature polypeptide encoded by the nucleotide sequence encoding the transgalatosylase contained in DSM accession no: 20583, and
  j. a polypeptide comprising an amino acid sequence having at least 66% sequence identity to the amino acid sequence of the mature polypeptide encoded by the nucleotide sequence encoding the transgalatosylase, contained in ATCC accession no: 29176.

Aspect 2. The polypeptide according to aspect 1, wherein the polypeptide of above items a, c, e, g and i at the most has a length of 1806 amino acids and the polypeptide of above items b, d, f, h and j at the most has a length of 1767 amino acids Aspect 3, A polypeptide having transgalactosylating activity selected from the group consisting of:

a. a polypeptide comprising an amino acid sequence having at least 66% sequence identity to the amino acid sequence of the mature polypeptide of SEQ ID NO: 1,
b. a polypeptide comprising an amino acid sequence having at least 66% sequence identity to the amino acid sequence of the mature polypeptide of SEQ ID NO: 2,
c. a polypeptide encoded by a polynucleotide that hybridizes under at least low stringency conditions with i) the nucleic acid sequence comprised in SEQ ID NO: 10 encoding the mature polypeptide of SEQ ID NO: 1; ii) the cDNA sequence of i) the complementary strand of i) or ii);
d. a polypeptide encoded by a polynucleotide that hybridizes under at least low stringency conditions with i) the nucleic acid sequence comprised in SEQ ID NO: 11 encoding the mature polypeptide of SEQ ID NO: 2; ii) the cDNA sequence of i) or iii) the complementary strand of i) car ii);
e. a polypeptide comprising a conservative substitution, deletion and/or insertion of one or more amino acids of SEQ ID NO: 1, and
f. a polypeptide comprising a conservative substitution, deletion and/or insertion of one or more amino acids of SEQ ID NO: 2.

Aspect 4. The polypeptide according to aspect 3, wherein the polypeptide of above items a, c, and e at the most has a length of 1806 amino acids and the polypeptide of above items h, d, and f at the most has a length of 1767 amino acids.

Aspect 5. A polypeptide having transgalactosylating activity selected from the group consisting of:
a. a polypeptide comprising an amino acid sequence having at least 66% sequence identity to the amino acid sequence of the mature polypeptide of SEQ ID NO: 1,
b. a polypeptide encoded by a polynucleotide that hybridizes under at least low stringency conditions with i) the nucleic acid sequence comprised in SEQ ID NO: 10 encoding the mature polypeptide of SEQ ID NO: 1; ii) the cDNA sequence of i) or iii) the complementary strand of i) or ii); and
c. a polypeptide comprising a conservative substitution, deletion and/or insertion of one or more amino acids of SEQ ID NO: 1.

Aspect 6. The polypeptide according to aspect 5, wherein the polypeptide of above items a, b, and c at the most has a length of 1806 amino acids.

Aspect 7. A polypeptide having transgalactosylating activity selected from the group consisting of:
a. a polypeptide comprising an amino acid sequence having at least 66% sequence identity to the amino acid sequence of the mature polypeptide of SEQ ID NO: 2,
b. a polypeptide encoded by a polynucleotide that hybridizes under at least low stringency conditions with i) the nucleic acid sequence comprised in SEQ ID NO: 11 encoding the mature polypeptide of SEQ ID NO: 2; ii) the cDNA sequence of i) or iii) the complementary strand of i) or ii); and
c. a polypeptide comprising a conservative substitution, deletion and/or insertion of one or more amino acids of SEQ ID NO: 2, Aspect 8. The polypeptide according to aspect 7, wherein the polypeptide of above items a, b and c at the most has a length of 1767 amino acids.

Aspect 9. The polypeptide according to any one of aspects 1-8 having a ratio of transgalactosylating activity:β-galactosidase activity of at least 1, at least 2.5, at least 3, at least 4, at least 5, at least 6, at least 7, at least 8, at least 9, at least 10, at least 11, or at least 12.

Aspect 10. The polypeptide according to any one of aspect 1-9, wherein the amino add sequence has at east 68%, 70%, 72%, 74%, 76%, 78%, 80%, 85%, 90%, 91%, 92%, 93%, 94%, 95%, 96%, 97%, 98%, or 99%, sequence identity to the mature amino add sequence of SEQ ID NO: 1 or 2.

Aspect 11. The polypeptide according to aspects 1-10 containing the catalytic domain of glycosyl hydrolase class 2 (GH 2), preferably containing one or more Pfam domains selected from: Glyco_hydro2N (PF02837), Glyco_hydro (PF00703), Glyco_hydro 2C (PF02536) and Bacterial Ig-like domain (group 4) (PF07532).

Aspect 12. The polypeptide according to any one of aspects 1-11 comprising or consisting of the amino acid sequence of SEQ ID NO: 1.

Aspect 13. The polypeptide according to any one of aspects 1-12 being a fragment of the mature polypeptide of SEQ ID NO: 12.

Aspect 14. The polypeptide according to any one of aspects 1-11 comprising or consisting of the amino acid sequence of SEQ ID NO: 2

Aspect 15. The polypeptide according to any one of aspects 1-11 and 14 being a fragment of the mature polypeptide of SEQ ID NO: 13.

Aspect 16. A polypeptide having transgalactosylating activity comprising an amino acid sequence having
a. at least 66% sequence identity to the amino acid sequence of SEQ ID NO: 1, and/or
b. at least 66% sequence identity to the amino acid sequence of SEQ ID NO: 2, Aspect 17. The polypeptide according to any one of aspects 1-16 comprising an amino acid sequence having at least 66% sequence identity to the amino acid sequence of SEQ ID NO: 1.

Aspect 18. The polypeptide according to any one of aspects 1-17 provided that the polypeptide is not the beta-galactosidase from *Ruminococcus hansenii* having SEQ ID NO: 12.

Aspect 19. The polypeptide according to any one of aspects 146 comprising an amino acid sequence having at least 66% sequence identity to the amino acid sequence of SEQ ID NO: 2.

Aspect 20. The polypeptide according to any one of aspects 1-16 and 19 provided that the polypeptide is not the beta-galactosidase from *Ruminococcus lactaris* having SEQ ID NO: 13.

Aspect 21. The polypeptide according to any one of aspects 1-15 comprising an amino add sequence having at least 60% sequence identity to the amino acid sequence of SEQ ID NO: 5.

Aspect 22. The polypeptide according to any one of aspects 1-21 comprising an amino add sequence having at least 94sequence identity to the amino acid sequence of SEQ ID NO: 8.

Aspect 23. The polypeptide according to any one of the aspects 1-22 containing one or more Pfam domains selected from: Glyco_hydro2N (PF02837), Glyco_hydro (PF00703), Glyco_hydro 2C (PF02836) and Bacterial Ig-like domain (group 4) (PF07532).

Aspect 24. A polypeptide having a ratio of transgalactosylating activity:β-galactosidase activity of at least 1, at least 2.5, at least 3, at least 4, at least 5, at least 6, at least 7, at least 8, at least 9, at least 10, at least 11, or at least 12 as measured at a concentration of 6 LAU/ml in a milk-based assay at 37° C. and 5 w/w % lactose after 30 minutes reaction.

Aspect 25. The polypeptide according to any one of the aspects 1-24, which is derived from *Ruminococcus hansenii* or *Ruminococcus lactaris*.

Aspect 26. The polypeptide according to any one of the aspects 24-25, wherein the polypeptide comprises an amino acid sequence as defined in any one of aspects 1-23.

Aspect 27. The polypeptide according to any one of the aspects 1-26 having a ratio of transgalactosylating activity:β-galactosidase activity of at least 1, at least 2.5, at least 3, at least 4, at least 5, at least 6, at least 7, at least 8, at least 9, at least 10, at least 11, or at least 12 as measured at a concentration of 6 LAU/ml in a milk-based assay at 37° C. and 5 w/w % lactose after 30 minutes reaction.

Aspect 28. The polypeptide according to any one of the aspects 1-27, wherein the amino acid sequence comprises at least one or more amino acid residue(s) selected from the following groups:
 a. an amino acid residue selected from the group consisting of D/E/N/Q at a position corresponding to position 576 in SEQ ID NO: 1,
 b. an amino acid residue selected from the group consisting of D/E/N/Q at a position corresponding to position 583 in SEQ ID NO: 1,
 c. an amino acid residue selected from the group consisting of E/D/Q/N at a position corresponding to position 592 in SEQ ID NO: 1 and/or
 d. an amino acid residue selected from the group consisting of D/E/Q/N at a position corresponding to position 625 in SEQ ID NO: 1.

Aspect 29. The polypeptide according to any one of the aspects 1-28, wherein the amino acid sequence comprises at least one or more amino acid residue(s) selected from the following groups:
 a. an amino acid residue selected from the group consisting of D/E/N/Q at a position corresponding to position 592 in SEQ ID NO: 2,
 b. an amino acid residue selected from the group consisting of D/E/N/Q at a position corresponding to position 604 in SEQ ID NO: 2,
 c. an amino acid residue selected from the group consisting of E/D/Q/N at a position corresponding to position 608 in SEQ ID NO: 2 and/or
 d. an amino acid residue selected from the group consisting of D/E/Q/N at a position corresponding to position 641 in SEQ ID NO: 2.

Aspect 30. The polypeptide according to any one of the aspects 1-29, wherein the percentage of identity of one amino acid sequence with, or to, another amino acid sequence is determined by the use of the score matrix: blosum62mt2 and the VectorNTI Pair wise alignment settings

| Settings | K-tuple | 1 |
|---|---|---|
| | Number of best diagonals | 5 |
| | Window size | 5 |
| | Gap Penalty | 3 |
| | Gap opening Penalty | 10 |
| | Gap extension Penalty | 0.1 |

Aspect 31. The polypeptide according to any one of the aspects 1-30, which polypeptide has a transgalactosylating activity such that more than 20%, more than 30%, more than 40%, and up to 50% of the initial lactose is transgalactosylated as measured at a concentration of 6 LAU/ml in a milk-based assay at 37° C. and 5 w/w % lactose after 30 minutes of reaction.

Aspect 32. The polypeptide according to any one of the aspects 1-31, which polypeptide has a β-galactosidase activity such that less than 80%, less than 70%, less than 60%, less than 50%, less than 40%, less than 30%, or less than 20% of the lactose has been hydrolysed as measured at a concentration of 6 LAU/ml in a milk-based assay at 37° C. and 5 w/w % lactose.

Aspect 33. The polypeptide according to any one of the aspects 1-32, wherein the activity is measured at a concentration of 3 LAU/ml or 1 LAU/ml.

Aspect 34. The polypeptide according to any one of the aspects 1-33, wherein the activity is measured 15 minutes after addition of polypeptide, 30 minutes after addition of polypeptide, 60 minutes after addition of polypeptide, 90 minutes after addition of polypeptide, 120 minutes after addition of polypeptide or 180 minutes after addition of polypeptide.

Aspect 35. The polypeptide according to any one of the aspects 1-34, wherein the amino acid sequence has at least 68%, 70%, 72%, 74%, 76%, 78%, 80%, 85%, 90%, 91%, 92%, 93%, 94%, 95%, 96%, 97%, 98%, or 99%, sequence identity to the amino acid sequence of SEQ ID NO: 1.

Aspect 36. The polypeptide according to any one of the aspects 1-35, wherein the amino acid sequence has at least 80% sequence identity to the amino acid sequence of SEQ ID NO: 1.

Aspect 37. The polypeptide according to any one of the aspects 1-34, wherein the amino acid sequence has at east 68%, 70%, 72%, 74%, 76%, 78%, 80%, 85%, 90%, 91%, 92%, 93%, 94%, 95%, 96%, 97%, 98%, or 99%, sequence identity to the amino acid sequence of SEQ ID NO: 2.

Aspect 38. The polypeptide according to any one of the aspects 1-34 and 37, wherein the amino acid sequence has at least 80% sequence identity to the amino acid sequence of SEQ ID NO: 2.

Aspect 39. The polypeptide according to any one of the aspects 1-38, wherein the amino acid sequence has at least 64%, 66%, 68%, 70% 72%, 74%, 76%, 78%, 80%, 85%, 90%, 91%, 92%, 93%, 94%, 95%, 96%, 97%, 98%, or 99%, sequence identity to the amino add sequence of SEQ ID NO: 5.

Aspect 40. The polypeptide according to any one of the aspects 1-39, wherein the amino acid sequence has at least 95%, 96%, 97%, 98%, or 99%, sequence identity to the amino acid sequence of SEQ ID NO: 8.

Aspect 41. The polypeptide according to any one of the aspects 1-40, which polypeptide is a recombinant polypeptide.

Aspect 42. The polypeptide according to any one of the aspects 1-41, which polypeptide is freeze-dried.

Aspect 43. The polypeptide according to any one of the aspects 1-42, which polypeptide is in solution.

Aspect 44. The polypeptide according to any one of the aspects 1-43, which polypeptide is isolated.

Aspect 45. The polypeptide according to any one of the aspects 1-44, which polypeptide is purified.

Aspect 46. A polypeptide having the sequence of SEQ ID NO: 1 or 2.

Aspect 47. The polypeptide according to any one of the aspects 1-46 having one or more of the following characteristics:
 a) a ratio of transgalactosylating activity:β-galactosidase activity of at least 1, at least 2.5, at least 3, at least 4, at least 5, at least 6, at least 7, at least 8, at least 9, at least 10, at least 11, or at least 12 as measured at a concentration of 6 LAU/ml in a milk-based assay at 37° C. and 5 w/w % lactose after 30 minutes reaction, and/or
 b) has a transgalactosylating activity such that more than 20%, more than 30%, more than 40%, and up to 50% of the initial lactose has been transgalactosylated as measured at a concentration of 6 LAU/ml in a milk-based assay at 37° C. and 5 w/w % lactose after 30 minutes of reaction.

Aspect 48. A nucleic acid capable of encoding a polypeptide according to any one of the aspects 1-47.

Aspect 49. The nucleic acid according to aspect 48 having a nucleic acid sequence which is at least 60% identical to SEQ ID NO: 10 or 11.

Aspect 50. A plasmid comprising a nucleic acid according to any one of the aspects 48-49.

Aspect 51. An expression vector comprising a nucleic acid according to any one of the aspects 48-49, or capable of expressing a polypeptide according to any one of the aspects 1-47.

Aspect 52. A host cell comprising, preferably transformed with, a plasmid according to aspect 50 or an expression vector according to aspect 51.

Aspect 53. A cell capable of expressing a polypeptide according to any one of the aspects 1-47.

Aspect 54. The host cell according to aspect 52, or the cell according to aspect 53, which is a bacterial, fungal or yeast cell.

Aspect 55. The cell according to aspect 53, wherein the cell is selected from the group consisting of *Ruminococcus, Bifidobacterium, Lactococcus, Lactobacillus, Streptococcus, Leuconostoc, Escherichia, Bacillus, Streptomyces, Saccharomyces, Kluyverornyces, Candida, Torula, Torulopsis* and *Aspergillus*.

Aspect 56. The cell according to aspect 53, wherein the cell is selected from the group consisting of *Ruminococcus hansenii, Ruminococcus lactaris, Bifidobacterium breve, Bifidobacterium longum, Bifidobacterium infantis, Bifidobacterium bifidum* and *Lactococcus lactis*.

Aspect 57. A method of expressing a polypeptide, the method comprising obtaining a host cell or a cell according to any one of aspects 52-56 and expressing the polypeptide from the cell or host cell, and optionally purifying the polypeptide.

Aspect 58. A method of expressing a polypeptide, the method comprising obtaining a cell according aspect 53 and expressing the polypeptide from the cell, and optionally purifying the polypeptide.

Aspect 59. A composition comprising a polypeptide according to any one of aspects 1-47, preferably a food composition, more preferably a dairy product.

Aspect 60. A composition comprising a polypeptide as defined in any of aspects 1-47 and a stabilizer.

Aspect 61. A composition comprising a polypeptide as defined in any of aspects 1-47 and a carbohydrate substrate.

Aspect 62. The composition according to aspect 61, wherein the carbohydrate substrate is a disaccharide.

Aspect 63. The composition according to aspect 62, wherein the disaccharide is lactase.

Aspect 64. A method for producing a dairy product by treating a milk-based substrate comprising lactose with a polypeptide having a ratio of transgalactosylating activity:β-galactosidase activity of at least 1, at least 2.5, at least 3, at least 4, at least 5, at least 6, at least 7, at least 8, at least 9, at least 10, at least 11, or at least 12 as measured at a concentration of 6 LAU/ml in a milk-based assay at 37° C. and 5 w/w % lactose after 30 minutes reaction.

Aspect 65. A method for producing a food product by treating a substrate comprising lactose with a polypeptide as defined in any one of aspects 1-47.

Aspect 66. A method for producing a dairy product by treating a milk-based substrate comprising lactose with a polypeptide according to any one of aspects 1-47.

Aspect 67. The method according to any one of aspects 64-66 further treating the substrate with a hydrolysing beta-galactosidase.

Aspect 68. The method according to any one of aspects 64-67, wherein the polypeptide has a ratio of transgalactosylation activity as defined in aspect 64.

Aspect 69. The method according to any one of aspects 64-68, wherein the milk-based substrate is yoghurt, cheese, or fermented dairy products.

Aspect 70. The method according to any one of aspects 64-69 further comprising fermenting said substrate with a microorganism capable of fermenting said substrate.

Aspect 71. The method according to any one of aspects 64-70, wherein substrate such as the milk-based substrate is yogurt.

Aspect 72. The method according to any one of aspects 64-71, wherein the treatment with the polypeptide and the microorganism is performed essentially at the same time.

Aspect 73. The method according to any one of aspects 64-72, wherein the polypeptide and the microorganism are added to the milk-hared substrate essentially at the same time.

Aspect 74. The method according to any one of aspects 64-73, wherein the polypeptide Is derived from a microorganism of the genus *Ruminococcus*.

Aspect 75. Use of a cell of any one of aspects 53 and 55-56 for producing a product selected from the group consisting of yoghurt, cheese, fermented milk product, dietary supplement and probiotic comestible product.

Aspect 76. A food product, preferably a dairy product, comprising a transgalactosylating enzyme obtained from *Ruminococcus hansenii* or *Ruminococcus lactaris*, preferably as defined in item a-h in aspect 1, and more preferably a polypeptide as defined in any one of aspects 1-47.

Aspect 77. A dairy product comprising a cell of any one of aspects 53 and 55-56.

Aspect 78. A dairy product comprising a polypeptide as defined in any one of aspects 1-47.

Aspect 79. A dairy product comprising a polypeptide as defined in any one of aspects 1-47 in a concentration of 0.01-1000 ppm.

Aspect 80. A dairy product comprising an inactivated polypeptide as defined in any one of aspects 1-47.

Aspect 81. A dairy product comprising an inactivated polypeptide as defined in any one of aspects 1-47 in a concentration of 0.01-1000 ppm.

Aspect 82. A dairy product comprising GOS formed in situ by a polypeptide as defined in any one of aspects 1-27.

Aspect 83. Use of a transgalactosylating polypeptide of any one of aspects 1-47 or a cell of any one of aspects 53 and 55-56, for producing galacto-oligosaccharides.

Aspect 84. Use of a transgalactosylating polypeptide of any one of aspects 1-47 or a cell of any one of aspects 53 and 55-56, for producing galacto-oligosaccharides to be part of a product selected from the group consisting of yoghurt, cheese, fermented dairy products, dietary supplements and probiotic comestible products.

Aspect 85. Use of a transgalactosylating polypeptide of any one of aspects 1-47 or a cell of any one of aspects 53 and 55-56, for producing galacto-oligosaccharides to enhance the growth of *Bifidobacterium*.

Aspect 86. Use of a transgalactosylating polypeptide of any one of aspects 1-47 or a cell of any one of aspects 53 and 55-56, for producing galacto-oligosaccharides to enhance the growth of *Bifidobacterium* in a mixed culture fermentation.

Aspect 87. A process for producing a transgalactosylating polypeptide of any one of aspects 1-47, comprising culturing a cell of any one of aspects 53 and 55-56 in a suitable culture medium under conditions permitting expression of said polypeptide, and recovering the resulting polypeptide from the culture.

Aspect 88. A process for producing galacto-oligosaccharides, comprising contacting of an polypeptide of any one of aspects 1-47 or a cell of any one of aspects 53 and 55-56 with a milk-based solution comprising lactose.

Aspect 89. A galacto-oligosaccharide or composition thereof obtained by treating a substrate comprising lactose with a polypeptide as defined in any one of aspects 1-47.

Example 1

Production of Polypeptide

A synthetic *Ruminococcus hansenii* gene with codons optimised for expression in *Bacillus subtilis* was purchased from GeneART (Regensburg, Germany). The synthetic gene was cloned into the pBN *Bacillus subtilis* expression vector (FIG. 1) and transformed into the *Bacillus subtilis* strain BG6006. Transformants were restreaked twice onto LB plates containing 10 μg/mL Neomycin as selection.

A preculture was setup in LB media containing 10 μg/mL Neomycin and cultivated for 7 hours at 37° C. and 180 rpm shaking. 500 μl of this preculture was used to inoculate 50 mL Grant's modified medium containing 10 μg/mL Neomycin at allowed to grow for 48 hours at 33° C. and 180 rpm shaking.

Cultures were harvested by centrifugation at 10.000×g and sterile filtered. The fermentation broths were up-concentrated using Sartorius Vivaspin20 MWCO 10,000 Dalton (Product code VS2002) at 4000 rpm in a tabletop centrifuge. The concentrate was stabilised with 20 w/w % glycerol.

Grant's modified media was prepared according to the following directions:

| PART I (Autoclave) | |
|---|---|
| Soytone | 10 g |
| Bring to | 500 mL per liter |
| PART II | |
| 1M K$_2$HPO$_4$ | 3 mL |
| Glucose | 75 g |
| Urea | 3.6 g |
| Grant's 10X MOPS | 100 mL |
| Bring to 400 mL per liter | |

PART I (2 w/w % Soytone) was prepared, and treated in an autoclave for 20-25 mins.

PART II was prepared, and mixed with PART 1 and pH was adjusted to pH to 7.3 with HCl/NaOH.

The volume was brought to full volume and sterilized through 0.22-um PES filter.

10×MOPS Buffer was re tired according to the following directions:

| | |
|---|---|
| 83.72 g | Tricine |
| 7.17 g | KOH Pellets |
| 12 g | NaCl |
| 29.22 g | 0.276M K2SO4 |
| 10 mL | 0.528M MgCl2 |
| 10 mL | Grant's Micronutrients 100X |
| Bring to 100 mL. | |

100× Micronutrients was prepared according to the following directions:

| | |
|---|---|
| Sodium Citrate•2H2O | 1.47 g |
| CaCl2•2H2O | 1.47 g |
| FeSO4•7H2O | 0.4 g |
| MnSO4•H2O | 0.1 g |
| ZnSO4•H2O | 0.1 g |
| CuCl2•2H2O | 0.05 g |
| CoCl2•6H2O | 0.1 g |
| Na2MoO4•2H2O | 0.1 g |

The volume was reached with milliQ water.
Sterilization was through 0.2 um PES filter.
Protection from light was by wrapping in foil.
Storing was at 4 C.

Determining the Hydrolysis Activity of the Enzyme Preparations

Enzymatic activity of *Ruminococcus hansenii* (SEQ ID NO:1), *Ruminococcus lactaris* (SEQ ID NO:2) and *Bifidobacterium bifidum* BIF3d3 (truncated) (as described by Jørgensen et al. (2001), Appl. Microbiol. Biotechnol., 57: 647-652 and EP patent 1,283,876) were measured using the commercially available substrate 2-Nitrophenyl-β-D-Galactopyranoside (ONPG) (Sigma N1127).

1×ONPG buffer composition:

| | |
|---|---|
| 50 mM | Na-Citrate |
| 100 mM | NaPO4 |
| 2 mM | CaCL2 |
| 1 mM | MgCL2 |
| 20 mM | ONPG |

Dilution series of above enzymes and Lactozym® (from Novozymes) as a standard control were made in 96 well microtiter plates. 75 μl of the dilutions were transferred to a new microtiter plate and mixed with 75 μl of 2× concentrated ONPG-buffer. Absorbance measurements were recorded at 450 nm on a Molecular Device SpectraMax controlled by the Softmax software package. The chamber was equilibrated to 37° C. and recordings were made every 15 seconds for 10 min in total. The ONP generation was measured and the Vmax of the reaction was determined. The Vmax for each enzyme preparation was compared to known concentrations of (3000 LAU/ml) Lactozym® and the activity in LAU/ml were calculated from the Lactozym® standard (see Table 1 below).

TABLE 1

| Enzyme | LAU/ml |
|---|---|
| Lactozym ® | 3000 |
| *Bifidobacterium bifidum* BIF3d3 (truncated)* | 105 |
| *Ruminococcus lactaris* (SEQ ID NO: 2) | 45 |
| *Ruminococcus hansenii* (SEQ ID NO: 1) | 42 |

Example 2

Definition of GOS Producing Enzyme Unit

In the present application the relative transgalactosylation activity is defined as the difference between the amount of liberated glucose subtracted by the amount of liberated galactose divided by the amount of galactose generated in T-buffer at 37° C.

$$\text{Relative transgalactosylation activity} = \frac{[\text{Glucose}] - [\text{Galactose}]}{[\text{Glucose}]} \quad \text{Equation 1}$$

T-buffer was prepared as follows:

| | |
|---|---|
| 50 mM | Na-citrate |
| 100 mM | Na—PO4 |
| 2 mM | CaCl2 |
| 1 mM | MgCl2 |
| 5 w/w % | Lactose |
| pH 6.0 | |

Measuring Galactose and Glucose by HPLC Chromatography

Galactose and glucose were analysed using a Dionex ICS3000 system consisting of ICS-3000 AS Autosampler, ICS-3000 ED Detector, ICS-3000 DC Chromatography Module and a DP Gradient pump (Dionex Corp, Sunnyvale, Calif., USA).

Galactose and glucose were separated using a CarboPac PA1 column 4 mm. with a CarboPac PA1 4 mm guard column (Dionex Corp, Sunnyvale, Calif., USA). The flow was 1 mL/min. The gradient was performed according to table 2, and the quantification was made with the use of external standards.

TABLE 2

Gradient program (w/w %) used for analysis of monosaccharides in samples

| Time (min) | Milli Q water | 150 mM NaOH |
|---|---|---|
| 0-12 | 90%-85% | 10%-15% |
| 12-25 | 85%-0% | 15%-100% |
| 25-30 | 0% | 100% |
| 30-32 | 0%-90% | 100%-10% |
| 32-34 | 90% | 10% |

The used eluents were water and 150 nM NaOH. 150 mM NaOH (eluent) was prepared by degassing 2 L Milli Q water for 10 min and adding 16 mL 50% w/w NaOH and degassing for another 5 min.

Calculation of Trangalactosylation Activity

The relative transgalactosylation activity was calculated according to equation 1 and the concentrations of glucose and galactose were measured by HPLC.

TABLE 3

Galactose concentration in %:

| Time/min | 0 | 15 | 30 | 60 | 120 | 180 |
|---|---|---|---|---|---|---|
| Lactozym ® | 0 | 1.5 | 1.9 | 2.1 | 2.3 | 2.1 |
| Bifidobacterium bifidum BIF3d3 (truncated) | 0 | 0.5 | 1 | 1 | 1 | 0.9 |
| Ruminococcus hansenii (SEQ ID NO: 1) | 0 | 0.1 | 0.1 | 0.2 | 0.2 | 0.2 |
| Ruminococcus lactaris (SEQ ID NO: 2) | 0 | 0.1 | 0.1 | 0.1 | 0.2 | 0.3 |

TABLE 4

Glucose concentration in %:

| Time/min | 0 | 15 | 30 | 60 | 120 | 180 |
|---|---|---|---|---|---|---|
| Lactozym ® | 0 | 1.9 | 2.3 | 2.3 | 2.4 | 2.2 |
| Bifidobacterium bifidum BIF3d3 (truncated) | 0 | 1.5 | 1.8 | 1.8 | 1.6 | 1.8 |
| Ruminococcus hansenii (SEQ ID NO: 1) | 0 | 0.7 | 1.3 | 1.2 | 1.3 | 1.3 |
| Ruminococcus lactaris (SEQ ID NO: 2) | 0 | 0.4 | 0.5 | 0.8 | 0.7 | 0.8 |

TABLE 5

Ratio of transgalactosylating activity: β-galactosidase activity:

| Time/min | 0 | 15 | 30 | 60 | 120 | 180 |
|---|---|---|---|---|---|---|
| Lactozym ® | nd | 0.27 | 0.21 | 0.10 | 0.04 | 0.05 |
| Bifidobacterium bifidum BIF3d3 (truncated) | nd | 2.00 | 0.80 | 0.80 | 0.60 | 1.00 |
| Ruminococcus hansenii (SEQ ID NO: 1) | nd | 6.00 | 12.00 | 5.00 | 5.50 | 5.50 |
| Ruminococcus lactaris (SEQ ID NO: 2) | nd | 3.00 | 4.00 | 7.00 | 2.50 | 1.67 | nd: Not determined for this timepoint.

TABLE 6

Relative transgalactosylation activity in %:

| Time/min | 0 | 15 | 30 | 60 | 120 | 180 |
|---|---|---|---|---|---|---|
| Lactozym ® | nd | 21.05 | 17.39 | 8.70 | 4.17 | 4.55 |
| Bifidobacterium bifidum BIF3d3 (truncated) | nd | 66.67 | 44.44 | 44.44 | 37.50 | 50.00 |
| Ruminococcus hansenii (SEQ ID NO: 1) | nd | 85.71 | 92.31 | 83.33 | 84.62 | 84.62 |
| Ruminococcus lactaris (SEQ ID NO: 2) | nd | 75.00 | 80.00 | 87.50 | 71.43 | 62.50 | nd: Not determined for this timepoint.

Figure 2:
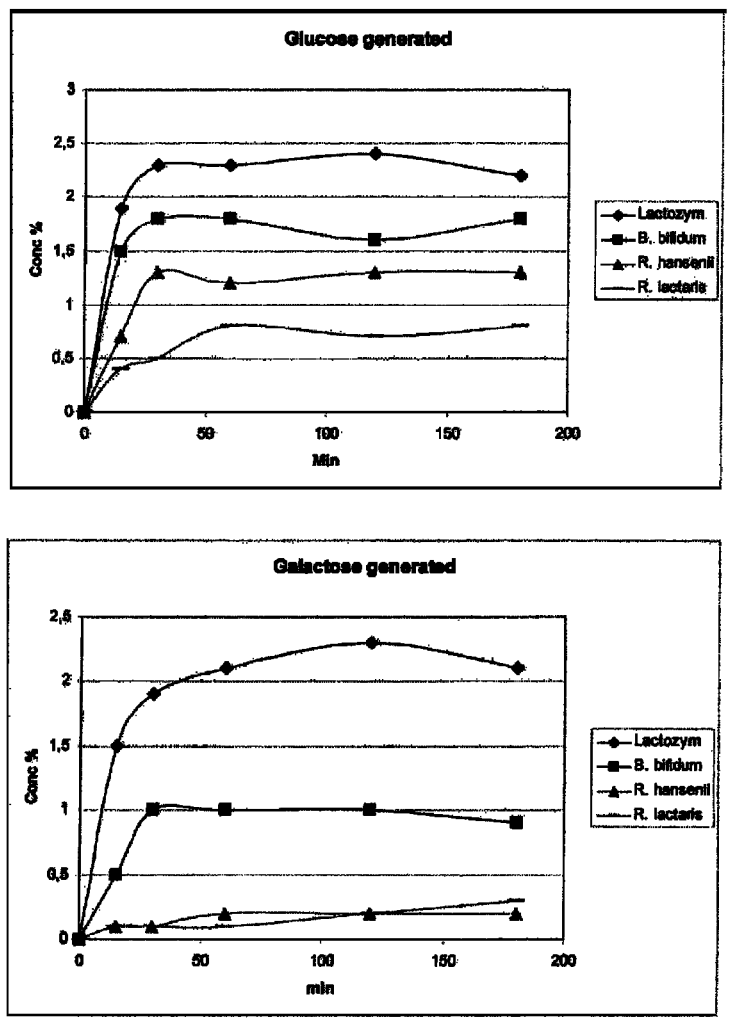

FIG. 2 displays the accumulation of glucose and galactose over time. As is clearly evident from FIG. 2 and the tables above, the *Ruminococcus hansenii* (SEQ ID NO:1) and *Ruminococcus lactaris* (SEQ ID NO:2) enzymes generate only between 10-20% of galactose relative to the *Bifidobacterium bifidum* BIF3d3 (truncated) enzyme. These finding suggest that both the *Ruminococcus hansenii* (SEQ ID NO:1) and *Ruminococcus lactaris* (SEQ ID NO:2) enzymes are able to exclude water from the active site more efficiently than Lactozym® and the *Bifidobacterium bifidum* BIF3d3 (truncated) enzyme.

Example 3

Assay in Milk

Samples were prepared in 9 w/w % reconstituted milk from skimmed milk powder (Humana Milk Union, DE NW508 EG) giving a final concentration of lactose of 5 w/w %. The enzymes were dosed based upon the LAU activity determined as described above at a final concentration of 6 LAU/ml. A sample was taken prior to addition of enzyme and additional samples were taken at indicated time points and the enzymes immediately inactivated by incubating at 95° C. for 10 minutes. Samples were diluted 1:10 and 2 µL were applied onto activated (161° C. for 10 min) HPTLC silica gel 60 (Merck Cat#1.05641.0001) plates with a CAMAG Automatic TLC Sampler 4. The TLC plates were eluted with an eluent containing (80) Acetonitril: (20) Ethylacetat: (50) 1-Propanol: (40) Water. Samples were visualised by heating (161° C. for 10 min) and allowed to cool down before soaking in 5 w/w % H2SO4 in 99.9% ethanol. Plates were developed with heating 161° C. for 3 min.

TABLE 7

Composition of standards:

| | Std A conc (w/w %) | Std B conc (w/w %) | Std C conc (w/w %) |
|---|---|---|---|
| Glucose | 0.5 | 0.4 | 0.1 |
| Lactose | 0.3 | 0.2 | 0.5 |
| Galactose | 0.1 | 0.05 | 0.3 |

Figure 3:
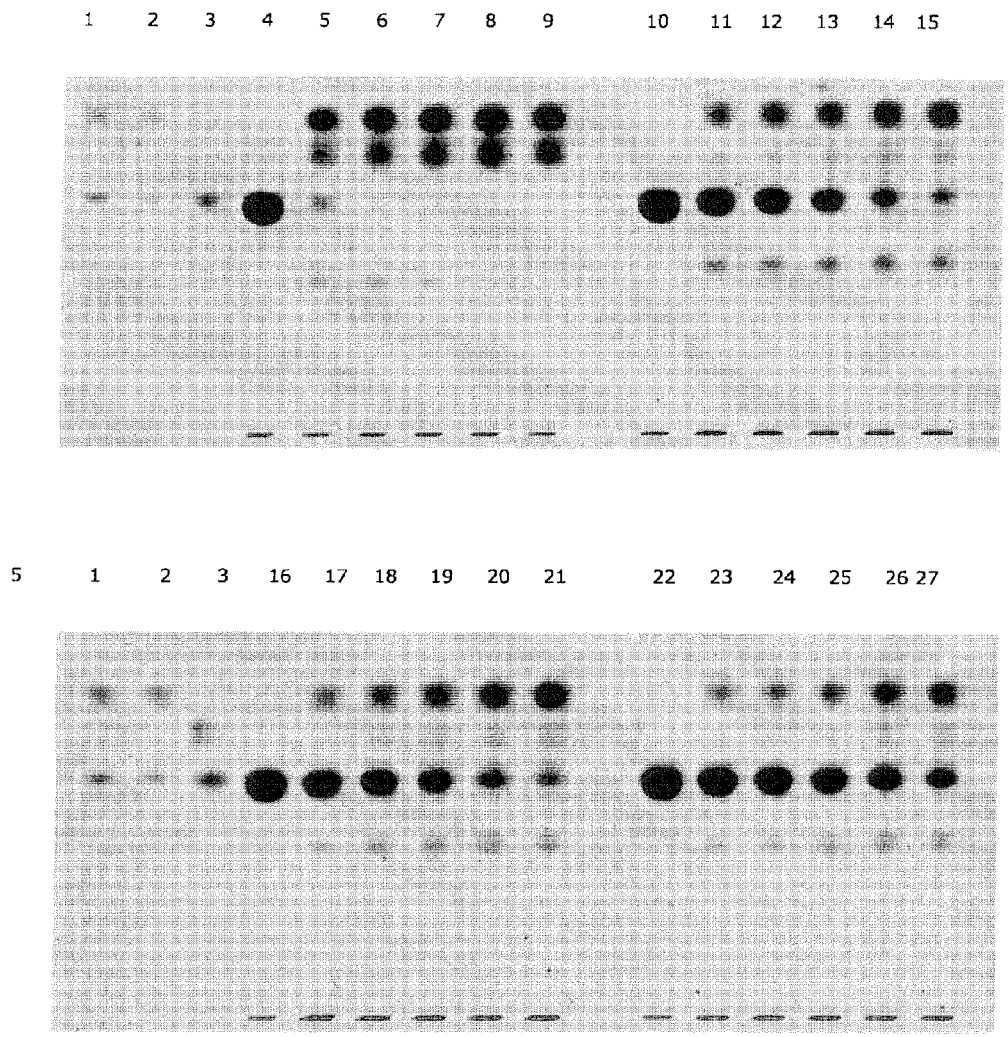
FIG. 3 shows the result of Thin Layer Chromatography of the polypeptides in 9 w/w % reconstituted milk giving a final concentration of lactose of 5% w/w. The polypeptides were dosed based upon the LAU activity determined as described in example 1 at a final concentration of 6 LAU/ml.

The sample number in FIG. 3 is as shown in below table. Sample Number:

| | | | | | |
|---|---|---|---|---|---|
| 1 | Std A | 8 | Lactozym ® 120 | 15 | *B. bifidum* 180 |
| 2 | Std B | 9 | Lactozym ® 180 | 16 | *R. hansenii* 0 min |
| 3 | Std C | 10 | *B. bifidum* 0 min | 17 | *R. hansenii* 15 min |
| 4 | Lactozym ® 0 min | 11 | *B. bifidum* 15 min | 18 | *R. hansenii* 30 min |
| 5 | Lactozym ® 15 min | 12 | *B. bifidum* 30 min | 19 | *R. hansenii* 60 min |
| 6 | Lactozym ® 30 min | 13 | *B. bifidum* 60 min | 20 | *R. hansenii* 120 min |
| 7 | Lactozym ® 60 min | 14 | *B. bifidum* 120 | 21 | *R. hansenii* 180 min |

| | | | |
|---|---|---|---|
| 22 | *R. lactaris* 0 min | | |
| 23 | *R. lactaris* 15 min | | |
| 24 | *R. lactaris* 30 min | | |
| 25 | *R. lactaris* 60 min | | |
| 26 | *R. lactaris* 120 min | | |
| 27 | *R. lactaris* 180 min | | |

FIG. 3 shows the sugar composition of the milk at various time points during incubation. Whereas Lactozym® generates approximately equal amounts of glucose and galactose, the *Bifidobacterium bifidum* BIF3d3 (truncated), *Ruminococcus hansenii* (SEQ ID NO:1) and *Ruminococcus lactaris* (SEQ ID NO:2) enzymes all generate more glucose than galactose. These results are indicative of all these enzymes being able to perform transgalactosylation in reconstituted milk with an initial lactose concentration of 5 w/w %.

Example 4

Activity of Catalytic Core Mutants of *Ruminococcus hansenii*

Purification of the Enzyme from Crude Samples

Crude enzymes samples were obtained as described in example 1.

Purification Method

Ion Exchange chromatography, Q HiTrap HP FF 5 ml

The column was prepared as described by the manufacturer and equilibrated in 20 mM Tris/HCl buffer, pH 8.0 (Buffer A).

The sample (5 ml) was desalted in Buffer A and applied to the column at a flow rate of 4 ml/min. The column was washed with buffer A and the bound proteins were eluted with a linear gradient of 0-0.6 M NaCl in buffer A. During the entire run fractions of 4 ml were collected.

Activity Assay

90 μL reaction buffer was mixed with 30 μL of the indicated diluted sample (table 8) of enzyme in a 96-well Eppendorf twin tech PCR plate (Cat. 951020401) and incubated for 30 minutes at 42° C. in an Eppendorf Mastercycler Gradient PCR machine. The reaction was stopped by transferring the mixture to a Costar 9017 96-well plate containing 120 μL 10% Na-carbonate (Stop solution). The reactions were measured at 420 nm in a Molecular Devices Spectra Max 190 plate reader.

TABLE 8

| | Protein, μg/ml | Diluted | OD420 | Time/min | Activity/min, % |
|---|---|---|---|---|---|
| E592Q Frac. 13 | 62 | 10X | 0.011 | 25 | 3 |
| D625N Frac. 14 | 11 | 2X | 0.168 | 25 | 50 |
| D588N Frac. 14 | 6 | 1X | 0.019 | 25 | 6 |
| D576N Frac. 17 | 29 | 5X | 0.270 | 5 | 81 |

TABLE 8-continued

| | Protein, μg/ml | Diluted | OD420 | Time/min | Activity/min, % |
|---|---|---|---|---|---|
| WT Frac. 17 | 33 | 5.5x | 0.335 | 5 | 100 |

Protein concentrations were adjusted to that of sample D588N by diluting With 50 mM Na-P buffer (ph 7.0) and activity was measured as described above.

Table 8 shows the protein concentration in the indicated fractions, fold of dilution to reach the concentration of D588N, the OD420 measurement, reaction time in minutes and relative activity per min to the *Ruminococcus hansenii* wild type enzyme (WT).

Figure 4:
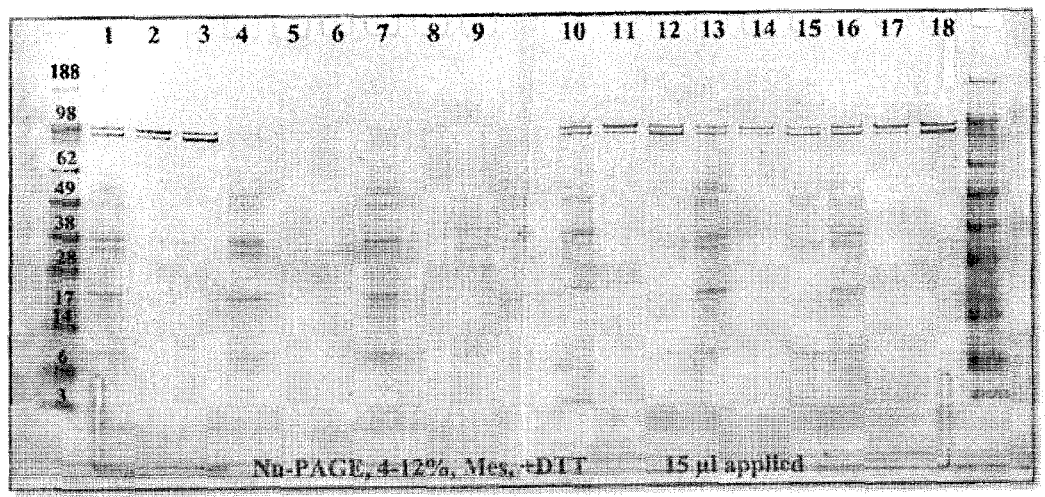
FIG. 4 shows the results of the anion exchange chromatography of variants of the Ruminococcus hansenii (SEQ ID NO:1). The gel is a Nu-PAGE 4-12% acrylamide gel stained with coomassie brilliant blue staining.

FIG. 4 shows the results of the anion exchange chromatography of the above variants of the *Ruminococcus hansenii* (SEQ ID NO:1). The gel is a Nu-PAGE 4-12% acrylamide gel stained with coomassie brilliant blue staining.

| Lane | Sample |
|---|---|
| 1 | E592Q Crude |
| 2 | Frac. 13 Eluate |
| 3 | Frac. 14 Eluate |
| 4 | D625N Crude |
| 5 | Frac. 14 Eluate |
| 6 | Frac. 15 Eluate |
| 7 | D588N Crude |
| 8 | Frac. 14 Eluate |
| 9 | Frac. 17 Eluate |
| 13 | D576N Crude |
| 14 | Frac. 17 Eluate |
| 15 | Frac. 18 Eluate |
| 16 | WT Crude |
| 17 | Frac. 17 Eluate |
| 18 | Frac. 18 Eluate |

```
LIST OF SEQUENCES
SEQ ID NO: 1 is a 1125 amino add truncated
fragment of SEQ ID NO: 12:
KADSQTQMSS EPEQVAVKDY GSNSARTQNF DSDWKPNLGD VSNAQTPTFD DSKWRTLSLP      60

HDYSTEQEYS QSLEAESGYL PGGVGWYRKN PTLGEEAKGK RIRIDPDGVY MNATVYVNGK     120

EVGTRPYGYT PFSFDITDYI SYDKENTIAV KVDHQTPSSR WYSGSGIYPS VNLTTTNDVR     180

VDLNGIKVES NNLEKEAGKT VNTDVKTTVV NGSKEAKNIT ITRTVPKKGE KPDKAIGTFT     240

TEAQEIGAGK KTEISATVPV KNPELWSVEN PALYTIRTEV KAGDKLLDSY DTEYGFRYLN     300

FDTETGPQLN GKNVKLKGVC MRHDQGALGA VANRRAIERQ VEILQEMGCN SIRVTHNPAS     360

KDLIEVCNEK GILVIEEVRD GWHRAKNGNS NDYSVWPEKA IEEDNAILGK EADMTWAEYD     420

LKAIMKRDQN APSIIEWSLG NEIQEGAGGS GYAERADKLI KWAKEADATK TLTIGSNAVK     480

PGDWEQVSIG DKLTKAGGTS GTNYSDGASY DKIHKSHPDW KLYGSETASS VNSRGIYSVT     540

GNQEATSDQQ LTAYDNSRVN WGALASQAWY DVIQPDPVAG KYVWTGFDYI GEPTPWNGTD     600

PGAKGTWPSP KNSYPGIIDT AGPPKDSYYF YQSQWNEEVN TLRVLPAWNE DVVKKNSDGT     660

VPVVVYSDAK EVELPRTPAN GGEKKSLGKK TFKTETTKAG YSYQVLENGK KKHKDLYMEW     720

QVPYEAGTLE AVAKDADGNV IKDTWGESVV KTTGEEAKLS AKTDRNSIQA DGKDLSYITV     780

DVTDKDGNIV PDAANRVTHD VQGAGKLVGV DNGSSPDRDS YKADNRKAFS GKVLAIVQST     840

EKAGEITVTA KADGLESSTV KITTTPVKEE PSERYVESYK YSKSYYVKTG TKPQLPKKIE     900

AQYSDRTKED VAVKWDEISD EQISKTGSFT VEGTVGKRDI TVRINMIDDV AALLNYSGAT     960

QKGVKPQLPD VRPAVLPDGT VLAASFPVQW DEKDADTFQK PDEIVTVNGS ADIFGKTIPV    1020

TASIRVQKED IKIGSSVTNV AKLSQNIQGS DTLEAIKDGK TEMSLNNDGG PNESAWSNWD    1080

ASQKGTKEAE LTFTFDTQQR IGEIVIHPAK DNNSIRHPDA GTTEI                    1125

SEQ ID NO: 2 is 1150 amino acid truncated
fragment of SEQ ID NO: 13:
AGVSVPALAQ QAVRTESQTQ MSSDPELVYV NNYSSTAQRS QNPNSNWKPY FGDAGNAQGA      60

TFDDSKWEQV SLPHDYSISQ EYSKSMEAES GYLGGGTGWY RKNFTLSSDT QGKPVRIDFD     120

GVYMNATVWV NGHEVGTHPY GYTSPSFDIT DYVKYDGENT IAVKVVNNTP SSRWYSGSGI     180

YPDVDLTITD DVHVDLNGTK TVVPNLETEK GSTVNTDVTA TVANDSDAAK SVAVRHTVFP     240

KDGSADQSIG TVTTNAQSIA AGATAEIQAT VPVSNPELWS VENPSLYTVR TEVLVDGQVT     300

DTYDTEYGFR YFNFDSNTGF SLNGENMKLK GVCMHHDQGS LGAAAYDSAI DRQVKILKEM     360

GCNSIRVTHN PAAQDLIDAC NEQGILVVEE APDTWTRPKN GNSNDYSVWF NQTVASDNEI     420

LGATNGETWA QFDLESMISR DYNAPSVIMW SLGNEVMEGI SGGTDAEYEA YATLKINWAY     480

DADNTRPMTI GDNKLKANWQ ISKTFARLLT EKGGTVGFNY ADGRVLDSYH SSNSNWLLYG     540

SETASAINSR GIYYRTTGGG QTSDKQLTSY DNSNVGWGAT ASNAWYTVLT RDFAAGEYVW     600

TGFDYLGEPT PWNGTGSGAV GSWPSPKNSY FGIIDTAGFA KDSYYFYQSQ WNDDVTTLHV     660

LPAWNNNVVS PDSSGNVPVV VYSDAASVEL FPQAKGSDTK TSLGKKTHTQ KTTDAGYTYQ     720

IYEGSDKNST TDKNLYLTWN VPYADGTVSA VAYNSNGQKI TDTVGQSSVT TTGKASKLKA     780

SADHKKIAAD GESLSYITVD VTDANGNIVP DAENPVKFTV EGDGELVGVD NGSSPDHDSY     840

QADNPKAFSG KVLAIVKSTK EAGTITVTAS ADGLDSASVK ITTTAVDNGS TEKQIDSFKM     900

SPTYYVKVGS TPELPEKIVT RYTDGTSEEL PVTWDAITED QIAAAGSFQV KGTVKGGYSV     960

AVNVNMIDEV GGLLNYSTNT AVGVAPVLPT SPPAVLQDGT VMDVTFPVTW EDKAASAYDK    1020

AGTVTVNGTA NVLGKEIAVT ASVRVQEETI TIGDSVSADA LNLTQSVPAD KQSDTLNAIK    1080

DGSTTISSNT SGGANPTVWS NYDYSQDGNT TADIIPEYAT EQRLGQTVTH EARDSWSMRY    1140
```

PDAGATEIYV                                                                   1150

SEQ ID NO: 3 is amino acid residues 559-649
of SEQ ID No: 1:
VNWGALASQA WYDVIQRDFV AGEYVWTGFD YIGEPTPWNG TDPGAKGTWP SPKNSYFGII    60

DTAGPPKDSY YFYQSQWNEE VNTLAVLPAW N                                   91

SEQ ID NO: 4 is amino acid residues 579-649
of SEQ ID No: 1:
AGEYVWTGFD YIGEPTPWNG TDPGAKGTWP SPKNSYFGII DTAGFPKDSY YFYQSQWNEE    60

VNTLHVLPAW N                                                         71

SEQ ID NO: 5 is amino acid residues 579-636
of SEQ ID No: 1:
AGEYVWTGFD YIGEPTPWNG TDPGAKGTWP SPKNSYFGII DTAGFPKDSY YFYQSQWN      58

SEQ ID NO: 6 is amino acid residues 575-665
of SEQ ID No: 2:
VGWGATASNA WYTVLTPDFA AGEYVWTGFD YLGEPTPWNG TGSGAVGSWP SPKNSYFGII    60

DTAGPAKDSY YPYQSQWNDD VTTLHVLPAW N                                   91

SEQ ID NO: 7 is amino acid residues 594-665
of SEQ ID No: 2:
AGEYVWTGFD YLGEPTPWNG TGSGAVGSWP SPKNSYFGYI DTAGFAKDSY YFYQSQWNDD    60

VTTLHVLPAW N                                                         71

SEQ ID NO: 8 is amino acid residues 594-652
of SEQ ID No: 2:
AGEYVWTGFD YLGEPTPWNG TGSGAVGSWP SPKNSYFGII DTAGPAKDSY YFYQSQWN      58

SEQ ID NO: 9 is a signal peptide from the pBN
Bacillus subtilis expression vector:
VRSKKLWISLLFALALIFTMAFGSTSSAQA SEQ ID NO: 10 is the nucleotide sequence encoding
SEQ ID NO: 1 including sequence encoding the signal
peptide:
gtgagaagcaaaaaattgtggatcagtttgctgtttgctttagcgttaatctttacgatggcgttcggcagcacatccagcgcg caggcggcagggaaaaaagcagatagccaaacacaaatgtcatcagaaccggaacaagttgcggttaaagattatggctcaaat agcgcacgcacacagaattttgatagcgattggaaatttaacctgggagatgttagcaatgcacagacaccgacatttgatgat tcaaaatggcgcacactgtcactgccgcatgattatagcatcgaacaggaatattcacaatcactggaagcagaatcaggctat cttccgggaggcgttggctggtatcgcaaaaattttacactgggcgaagaagcgaaaggcaaacgcattcgcattgattttgat ggcgtctatatgaatgcaacagtctatgtgaatggcaaagaagttggcacacatccgtatggctatacaccgtttagctttgat atcacagattatatcagctatgataaagaaaacacaattgcggtcaaagtcgatcatcaaacaccgtcatcaagatggtattca ggcagcggcatttatagatcagtcaacctgacaacaacaaatgatgtccatgtcgatctgaatggcattaaagtcgaaagcaac aacctggaaaaagaagcaggcaaaacagtcaacacagatgtgaaaacaacagttgtgaacggctcaaaagaagcgaaaaacatc acaattacacatacagtctcttaaaaaaggcgaaaaaccggataaagcgatcggcacatttacaacagaagcgcaagaaattggc gcaggcaaaaaaacagaaatcagcgcaacagtcacggttaaaaatccggaactgtggtcagttgaaaatccggcactgtataca attcgcacagaagttaaagcaggcgataaactgctggatagctatgatacagaatatggctttcattatctgaactttgataca gaaacaggctttcagctgaatggcaaaaacgttaaactgaaaggcgtttgcatgcatcatgatcaaggcgcacttggcgcagtt gcaaatagaagagcaattgaacgccaagtcgaaattctgcaagaaatgggctgcaatagcattagagtcacacataatccggca agcaaagatctgattgaagtctgcaacgaaaaaggcattctggtcattgaagaagtttttgacggctggcatagagcaaaaat ggcaacagcaacgattatagcgtctggtttgaaaaagcgatcgaagaagataacgcgattctgggaaaagaagcggatatgact tgggcagaatatgatctgaaagcgattatgaaacgcgatcaaatgcaccgagcattattgaatggtcactgggcaatgaaatt caagaaggcgcaggcggatcaggctatgcagaaagagcggataaactgatcaaatgggcgaaagaagcagacgcaacaaaaaca ctgacaattggcagcaatgtagttaaaagaggcgattgggaacaagttagcatcggcgataaacttacaaaagcaggcggaaca tcaggcacaaattattcagatggcgcatcatatgataaaattcataaagaacatccggattggaaactgtatggctcagaaaca -continued gcatcatcagttaatagccgtggcatttattcagttacaggcaatcaagaagcaacaagcgatcaacaactgacagcgtatgat
aatagcagagttaattggggagcactggcatcacaagcatggtatgatgttatccagagagattttgtcgcaggcgaatatgtt
tggacaggctttgattatatcggcgaaccgacaccgtggaatggcacagatccgggagcaaaaggcacatggccgtcaccgaaa
aacagctactttggcattatcgatacagcaggctttccgaaagattcatattatttttatcagagccagtggaatgaagaagtc
aatacactgcacgttcttccggcatggaatgaagatgtcgtcaaaaaaaactcagatggcacagttccggttgttgtttattca
gatgcgaaagaagtcgaactgttttttacaccggcaaatggcgqagaaaaaaaagcctgggaaaaaaaacatttaaaacagaa
acaacaaaagctggctatagctatcaagttctggaaaacggcaaaaaaaaacataaagatctgtatatggaatggcaagttccg
tatgaagcaggcacacttgaagcagttgcgaaagatgcaaaaggcaacgtcattaaagatacagaaggcagaagcgtcgttaaa
acaacaggcgaagaagcaaaactgtcagcaaaaacggatcgcaatagcattcaagcagatggcaaagatctgtcatatattaca
gtcgatgtcacagataaagatggcaatattgttccggatgcagcaaatagagtcacatttgatgtccaaggcgcaggaaaactg
gttggcgttgataatggctcatcaccggatcatgatagctataaagcggataaccgcaaagcattttcaggcaaagttctggca
attgttcagtcaacagaaaaagcaggcgaaattacagttacagcaaaagcagatggcctggaatcaagcacagtcaaaatcaca
acaacaccggttaaagaagaaccgagcgaaagatatgtcgaaagctataaatacagcaaaagctattatgtgaaaacaggcaca
aaaccgcaactgccgaaaaaaattgaagcgcagtatagcgatcgcacaaaagaggatgttgcggtcaaatgggatgaaatctca
gatgaacaaattagcaaaacaggcagctttacagttgaaggcacagttggcaaaagagatatcacagtcaacattaacatgatc
gatgatgttgcagcactgctgaattattcaggcgcaacacaaaaaggcgttaaaccgcaacttccggatgttagaccggcagtt
ctgcctgatggcacagtcctggcagcatcatttccggttcagtgggatgaaaaagatgcggatacatttcagaaaccggatgaa
attgttacagttaacggcagcgcagatatctttggcaaaacaattccggttacagcaagcattagagtgcagaaagaagatatc
aaaattggcagcagcgttacaaatgttgcaaaactgagccaaaatattcaaggcagcgatacactggaagcaatcaaagatggc
aaaacagaaatgagcctgaataatgatggcggaccgaatgaatcagcatggtcaaattgggatgcatcacagaaaggcacaaaa
gaagccgaactgacatttacatttgatacacagcaacgcattggcgaaattgtcattcattttgcgaaagataacaactcaatc
agatttccggatgctggcacaacagaaatctaa SEQ ID NO: 11 is the nucleotide sequence encoding SEQ ID NO: 2 including sequence encoding the signal peptide:
gtggatcagtttgctgtttgctttagcgttaatcttacgatggcgttcggcagcacatccagcgcgcaggcggcagggaagca
ggcgtttcagttccggcactggcacaacaagcagttagaacagaaagccaaacacaaatgtcatcagatccggaactggtctat
gtgaataactatagcagcacagcacaaagaagccagaactttaacagcaactggaaattctacttcggagatgcgggaaatgca
caaggcgcaacatttgatgatagcaaatgggaacaagtttcactgccgcatgattattcaatcagccaagaatatagcaaatca
atggaagcagaatcaggctatcttggcggaggcacaggctggtatcgcaaaaattttacactgagcagcgatacacaaggcaaa
agagtccgcattgattttgatggcgtctatatgaatgcaacagtttgggttaatggccatgaagttggcacacatccgtatggc
tatacaagctttagctttgatatcacagattatgtgaaatatgatggcgaaaacacaattgcagtcaaagtcgtcaataataca
ccgtcaagcagatggtattcaggctcaggcatttatagagatgtcgatgacaatcacagatgatgttcatgttgatctgaacgg
cacaaaagttacaacaccgaacctggaaacagaaaaaaggcagcacagtcaatacagatgttacagcaacagttgcgaatgattc
agatacagcaaaatcagttgcagttcgccatacagttttccgaaagatggcagcgcagatcaatcaattggcacagtcacaac
aaatgcacaatcaattgcagcaggcgcaacagcagaaattcaagcaacggttccggtttcaaatcctgaactgtggtcagttga
aaatccgtcactgtatacagtcagaacagaagttctggtcgacggccaagtcacagatacatatgatacagaatatggctttcg
ctattttaactttgatagcaacacaggcttttcactgaatggcgaaaatatgaaactgaaaggcgtctgcatgcatcatgatca
aggctcacttggcgcagcagcatacgactcagcaattgatcgccaggtcaaaatcctgaaagaaatgggctgcaatagcattag
agtcacacataatccggcagcacaagatctgattgatgcgtgcaatgaacaaggcattctggttgttgaagaagcgtttgatac
ttggacaagaccgaaaaatggcaacagcaacgattatagcgtctggtttaatcagacagttgcgagcgataatgaaattctggg
agcgacaaatggcgaaacatgggcacaatttgatctggaaagcatgatctcacgcgattataatgcaccgtcagtcattatgtg
gtcactgggcaatgaagttatggaaggcattagcggaggcacagatgcagaatatgaagcgacagcgacgaaactgattaactg -continued

```
ggcgtatgatgcggataatacacgtccgatgacaattggcgataacaaactgaaagcgaactggcagatctcaaaaacatttgc gagactgctgacagaaaaaggcggaacagtgggctttaattatgcagatggcagagttctggattcatatcatagcagcaatag caattggctgctgtatggctcagaaacagcatcagcgattaatagccgtggcatctattatagaacaacaggcggaggccaaac atcagataaacagctgacaagctatgataattcaaatgttggctggggagcaacagcatcaaatgcatggtatacagttctgac aagagattttgcggcaggcgaatatgtttggacaggctttgattatctgggcgaaccgacaccgtggaatggcacaggctcagg cgcagttggctcatggccgtcaccgaaaaattcttatttggcattatcgatacagcaggcttcgcaaaagatagctattattt ttatcagagccagtggaatgatgatgttacaacactgcatgttcttccggcatggaataataatgtcgtcagcaaagattcatc aggcaatgttccggttgttgtttattcagatgcggcatcagtcgaactgttttttcaagcaaaaggcagcgatacaaaaacaag cctgggcaaaaaacatttacacagaaaacaacagacgcaggctatacatatcagatctatgaaggctcagataaaaacagcac aacagacaaaaacctgtatctgacatggaatgttccgtatgcagatggaacagtttcagcagttgcgtataatagcaacggcca gaaaattacagatacagttggccagtcctcagttacaacaacaggcaaagcgtcaaaactgaaagcatcagcggatcataaaaa aattgcagcggatggcgaatcactgtcatatatcacagtcgatgtcacagatgcgaatggcaatattgttccggatgcagaaaa tcgcgtcaaatttacagttgaaggcgatggcgaactggttggcgttgataatggctcatcaccggatcatgattcatatcaagc ggataaccgcaaagcattttcaggcaaagttctggcaattgtgaaaagcacaaaagaagctggcacaattacagttacagcatc agcagatggcctggattcagcatcagtcaaaatcacaacaacagcagtcgataatggcagcacagaaaaacaaatcgatagctt aaaatgagccgcacatattatgttaaagttggcagcacaccggaactgccggaaaaaattgtcacacgctatacagatggcaca tcagaagaactgcctgttacttgggatgcaattacagaagatcaaattgcagcagcaggctcatttcaagttaaaggcacagtc aaaggcggatattcagttacagtcaacgtcaacatgattgatgaagttggcggactgctgaattattcaacaaatacagcagtt ggcgttgcaccggttctgccgacatcaagaccggcagttctgcaagatggcacagttatggatgttacatttccggtcacatgg gaagataaagcagcaagcgcatatgataaagcaggcacagtgacagtcaatggcacagcaaatgttctgggcaaagaaattgca gttacagcgagcgttagagttcaggaagaaacaatcacaattggagattcagtttcagcggatgcactgaatctgacacaaagc gttccggcagataaacaaagcgatacactgaacgcaattaaagatggctcaacaacaattagctcaaatacaagcggaggcgca aatccgacagtttggagcaactatgactatagccaggatggcaatacgacagcggatatcatttttgaatatgcgacagaacaa agactgggccaaatcgttacacattttgcgagagatagctggtcaatgagatatcctgatgcaggcgctacagaaatttatgtc taa
```

SEQ ID NO: 12 is a beta-galactosidase from *Ruminococcus/Bleutia hansenil* DSM 20583:

```
myffgrsaimmltvktrkelfmrkqrlarigaatlaavltvqgrngfsstvyakeepvrvkadsqtqmssepeqvavkdygsns artqnfdsdwkfnlgdvsnaqtptfddskwrtlslphdysieqeysqsleaesgylpggvgwyrknftlgeeakgkrirridfdg vymnatvyvngkevgthpygytpfsfditdyisydkentiavkvdhqtpssrwysgsgiyrsvnitttndvhvdlngikvesnn lekeagktvntdvkttvvngskeeknititthtvfkkgekpdkaigtftteaqeigagkkteisetvpvknpelwsvenpalyti rtevkagdklldsydteygfhylnfdtetgfqlngknvklkgvcmhhdqgalgavanrraierqveilqemgcnsirvthnpas kdlievcnekgilvieevfdgwhrakngnsndysvwfekaieednailgkeadmtwaeydikaimkrdqnapsiiewslgneiq egaggsgyaeradklikwakeadatktltigsnavkrgdweqvsigdkltkaggtsatnysdgasydkihkehpdwklygseta ssvnsrgiysvtgnqeatsdqqltaydnsrvnwgalasqawydviqrdfvageyvwtgfdyigeptpwngtdpgakgtwpspkn syfgiidtagfpkdsyyfyqsqwneevntlhvlpawnedvvkknsdgtvpvvvysdakevelfftpanggekkslgkktfktet tkagysyqviengkkhkdlymewqvpyeagtleavakdakqnvikdtegrsvvkttgeeeklsaktdrnsiqadgkdlsyitv dvtdkdgnivpdaanrvtfdvqgagklvgvdngsspdhdsykadnrkafsgkvlaivqstekageitvtakadgiesstvkitt tpvkeepseryvesykysksyyvktgtkpqlpkkeaqysdrtkedvavkwdeisdeqisktgsftvegtvgkrdityninmidd vaailnysgatqkgvkpqlpdvrpavlpdgtvlaasfpvqwdekdadtfqkpdeivtvngsadifgktipvtasirvqkedikl gssvtnvakisqniqgsdtleaikdgktemslnndggpnesawsnwdasqkgtkeaeltftfdtqqrigeivihfakdnnsirf
```

-continued pdagtteifvsetgkdgtwekvevkehlgeekdrvkayryeiapvtatyvkvkvvnanatdtgnrkpctaitevelkkaegsfk vnetaeleevkvgervlpnaayaldsysvpetdaavtaktkdnasltiipkhenvvrmilesedhkatknfavrmgeeetvlpd ddsrdypvekitatagseykpgtanegpvkyvldgkaethwhtnwsvsgegskpehrtvtlqlgndeeeapmidairymprsng angryteyeiqysidgdkwqtaatgeidkkqtgwmilgfeepvqakyvrfigthttsdqgndkhmavselrarvateapapsek ytitanvndktmgavtldsetgeyekgtkatitavpkegfafvnwtidgqevskenpyihtvetdatitanferievenegwvq tengweyyengqkvvgwkevsgkwyyfeenglmqtgwvfvnnhwyymdqwgamcigwvavdghwyymdqwgamctgwvsvnghw yhmdqwgemqtgwalvdsnwyylntdgsmaigwvavnghwyymdqwgamqtgwalvdsnwyylntdgsmaigwvavnghwyymd qwgamqtgwvlvgsdwyyintdgsmassqwidgyyvdasgkmk SEQ ID NO: 13 is a glycosidase from *Ruminococcus lactaris* ATCC 29176:
mkkkkrctrvgagalaavlavtaagvsvpalaqqavrtesqtqmssdpelvyvnnyssttaqrsqnfnsnwkfyfgdagnaqgat fddskweqvslphdysisqeysksmeaesgylgggtgwyrknftlssdtqgkrvridfdgvymnatvwvnghevgthpygytsf sfditdyvkydgentiavkvvnntpssrwysgsgiyrdvdltitddvhvdlngtkvttpnletekgstvntdvtatvandsdaa ksvavrhtvfpkdgsadqsigtvttnaqsiaagateelqatvpvsnpelwsvenpslytvrtevlvdgqvtdtydteygfryfn fdsntgfslngenmklkgvcmhhdqgslgaaaydsaldrqvkllkemgcnslrvthnpaaqdlldacneqgilvveeafdtwtr pkngnsndysvwfnqtvasdneilgatngetwaqfdlesmisrdynapsvlmwslgnevmegisggtdaeyeatatklinwayd adntrpmtigdnklkanwqisktfarlltekggtvgfnyadgrvldsyhssnsnwllygsetasalnsrglyyrttgggqtsdk qltsydnsnvgwgatasnawytvltrdfaageyvwtgfdylgeptpwngtgsgavgswpspknsyfglldtagfakdsyyfyqs qwnddvttlhvlpawnnnvvskdssgnvpvvvysdaasvelffqakgsdtktslgkktftqkttdagytyqlyegsdknsttdk nlyltwnvpyadgtvsavaynsngqkitdtvgqssvtttgkasklkasadhkkiaadgeslsyitvdvtdangnivpdaenrvk ftvegdgelvgvdngsspdhdsyqednrkafsgkvlaivkstkeagtitvtasadgldsasvkitttavdngstekqidsfkms rtyyvkvgstpelpekivtrytdgtseelpvtwdaitedqiaaagsfqvkgtvkggysvavnvnmldevggllnystntavgva pvlptsrpavlqdgtvmdvtfpvtwedkaasaydkagtvtvngtanvlgkelavtasvrvqeetitigdsysadalnltqsvpa dkqsdtlnaikdgsttissntsgganptvwsnydysqdgnttadiifeyateqrlgqivthfardswsmrypdagateiyvspd gtnwakldttetigtesgnvkpytydfapvgatfvkfhltnstqatgttakactgiteielkvatgsrttnttaelqtitvngk evpqtaldskvyttpailaeieatakdnesvtvlpayndviriivesedhqtrntyevrlneaeqttpdsdsrdypvskltase gseqsttgvegpasnakdgdestlwhtrwsapaatsdqlwftyeleeetvldalryiprqgtadgqnngrvneyrvevstdgst wttvstgnwedsqdwklaeftepvaakyvrltgvhtygssaanvdkymsaaeirlrmaesktdiadaangvtvtapdsievaka daenpvmfdlsdivvkagdttirygvdyvisyenntdfgtaklvikgiykgasliyditvnpkkvdptdpdqpdkpdtpdngnd ngndnngngnnngtddgkkdpgqsgvtdknqgnnsnngtaagnkanaaaktgdtanmllpmiaamlagtavvgtisirrrrr SEQ ID NO: 14 is the nucleotide sequence encoding SEQ ID NO: 12
without the signal sequence:
aaagcagatagccaaacacaaatgtcatcagaaccggaacaagttgcggttaaagattatggctcaaatagcgcacgcacacag aattttgatagcgattggaaatttaacctgggagatgttagcaatgcacagacaccgacatttgatgattcaaaatggcgcaca ctgtcactgccgcatgattatagcatcgaacaggaatattcacaatcactggaagcagaatcaggctatcttccgggaggcgtt ggctggtatcgcaaaaattttacactgggcgaagaagcgaaaggcaaacgcattcgcattgattttgatggcgtctatatgaat gcaacagtctatgtgaatggcaaagaagttggcacacatccgtatggctatacaccgtttagctttgatatcacagattatatc agctatgataaagaaaacacaattgcggtcaaagtcgatcatcaaacaccgtcatcaagatggtattcaggcagcggcatttat agatcagtcaacctgacaacaacaaatgatgtccatgtcgatctgaatggcattaaagtcgaaagcaacaacctggaaaagaa gcaggcaaaacagtcaacacagatgtgaaaacaacagttgtgaacggctcaaaagaagcgaaaaacatcacaattacacataca gtctctttaaaaaaggcgaaaaaccggataaagcgatcggcacatttacaacagaagcgcaagaaattggcgcaggcaaaaaaaca gaaatcagcgcaacagtcccggttaaaaatccggaactgtggtcagttgaaaatccggcactgtatacaattcgcacagaagtt aaagcaggcgataaactgctggatagctatgatacagaatatggcttrcattatctgaactttgatacagaaacaggctttcag -continued

```
ctgaatggcaaaaacgttaaactgaaaggcgtttgcatgcatcatgatcaaggcgcacttggcgcagttgcaaatagaagagca
attgaacgccaagtcgaaattctgcaagaaatgggctgcaatagcattagagtcacacataatccggcaagcaaagatctgatt
gaagtctgcaacgaaaaaggcattctggtcattgaagaagttttttgacggctggcatagagcaaaaaatggcaacagcaacgat
tatagcgtctggtttgaaaaagcgatcgaagaagataacgcgattctgggaaaagaagcggatatgacttgggcagaatatgat
ctgaaagcgactatgaaacgcgatcaaaatgcaccgagcattattgaatggtcactgggcaatgaaattcaagaaggcgcaggc
ggatcaggctatgcagaaagagcggataaactgatcaaatgggcgaaagaagcagacgcaacaaaaacactgacaattggcagc
aatgcagttaaaagaggcgattgggaacaagttagcatcggcgataaacttacaaaagcaggcggaacatcaggcacaaattat
tcagatggcgcatcatatgataaaattcataaagaacatccggattggaaactgtatggctcagaaacagcatcatcagttaat
agccgtggcatttattcagttacaggcaatcaagaagcaacaagcgatcaacaactgacagcgtatgataatagcagagttaat
tggggagcactggcatcacaagcatggtatgatgttatccagagagattttgtcgcaggcgaatatgtttggacaggctttgat
tatatcggcgaaccgacaccgtggaatggcacagatccgggagcaaaaggcacatggccgtcaccgaaaaacagctactttggc
attatcgatacagcaggctttccgaaagattcatattattttttatcagagccagtggaatgaagaagtcaatacactgcacgtt
cttccggcatggaatgaagatgtcgtcaaaaaaaactcagatggcacagttccggttgttgtttattcagatgcgaaagaagtc
gaactgttttttacaccggcaaatggcggagaaaaaaaagcctgggaaaaaaaacatttaaaacagaaacaacaaaagctggc
tatagctatcaagttctggaaaacggcaaaaaaaaacataaagatctgtatatggaatggcaagttccgtatgaagcaggcaca
cttgaagcagttgcgaaagatgcaaaaggcaacgtcattaaagatacagaaggcagaagcgtcgttaaaacaacaggcgaagaa
gcaaaactgtcagcaaaaacggatcgcaatagcattcaagcagatggcaaagatctgtcatatattacagtcgatgtcacagat
aaagatggcaatattgttccggatgcagcaaatagagtcacatttgatgtccaaggcgcaggaaaactggttggcgttgataat
ggctcatcaccggatcatgatagctataaagcggataaccgcaaagcattttcaggcaaagtctggcaattgttcagtcaaca
gaaaaagcaggcgaaattacagttacagcaaaagcagatggcctggaatcaagcacagtcaaaatcacaacaacaccggttaaa
gaagaaccgagcgaaagatatgtcgaaagctataaatacagcaaaagctattatgtgaaaacaggcacaaaaccgcaactgccg
aaaaaaattgaagcgcagtatagcgatcgcacaaaagaggatgttgcggtcaaatgggatgaaatctcagatgaacaaattagc
aaaacaggcagcttacagttgaaggcacagttggcaaaagagatatcacagtcaacattaacatgatcgatgatgttgcagca
ctgctgaattattcaggcgcaacacaaaaaggcgttaaaccgcaacttccggatgttagaccggcagttctgcctgatggcaca
gtcctggcagcatcatttccggttcagtgggatgaaaaagatgcggatacatttcagaaaccggatgaaattgttacagttaac
ggcagcgcagatatctttggcaaaacaattccggttacagcaagcattagagtgcagaaagaagatatcaaaattggcagcagc
gttacaaatgttgcaaaactgagccaaaatattcaaggcagcgatacactggaagcaatcaaagatggcaaaacagaaatgagc
ctgaataatgatggcggaccgaatgaatcagcatggtcaaattgggatgcatcacagaaaggcacaaaagaagccgaactgaca
tttacattgatacacagcaacgcattggcgaaattgtcattcattttgcgaaagataacaactcaatcagatttccggatgct
ggcacaacagaaatctttgtttcagaaacaggcaaagatggcacatgggaaaaagttgaagtcaaagagcatattggcgaagaa
aaagatcgcgtcaaagcatatcgctatgaaattgcaccggttacagcgacatatgttaaagttaaagtcgtcaatgcgaacgcg
acagatacaggcaatagaaaaccgtgcacagcaattacagaagtcgaactgaaaaaagcagaaggcagctttaaagtcaacgaa
acagcagaactggaagaagttaaagttggcgaacgtgttctgccgaatgcagcatatgcactggattcatattcagttccggaa
acggatgcagcagttacagcaaaaacaaagataatgcgagcctgacaatcctgccgaaacatgaaaatgtcgtcagaatgatt
ctggaaagcgaagaccataaagcgacgaaaaactttgcagttagaatgggcgaagaagaaacagttctgccggatgatgattca
agagattatccggtcgaaaaaatcacagcaacaccaggctcagaatataaaccgggaacagcaaatgaaggaccggttaaatat
gttctggatggcaaagcagaaacacattggcatacaaattggtcagtttcaggcgaaggctcaaaaccggaacatagaacagtt
acactgcaactgggcaatgatgaagaagaagcaccgatgattgacgcactgagatatatgccgagatcaaatggcgcaaatggc
agagttacggaatatgaaattcagtatagcctggatggcgataaatggcaaacagcagcaacaggcgaaatcgataaaaaacaa
acaggctagatgatcctgggctttgaagaaccggttcaagcaaaatatgtccgctttattggcacacatacaacatcagatcag
ggcaatgataaacatatggcagtttcagaactgaqagcaagagttgcaacagaagcaccggcaccgtcagagaagtatacaatt
```

-continued acagcgaacgtcaacgataaaacaatgggagcagttacacttgatagcgaaacaggcgaatatgaaaaaggcacgaaagcaaca ctgacagcagttccgaaagaaggctttgcatttgtcaactggacaattgatggccaagaagtctcaaaagaaaacccgtatatc catacagttgaaacggatgcgacaatcacagcgaattttgaacgcattgaagtcgaaaatgaaggctgggttcaaacagaaaat ggctgggaatattatgagaatggccaaaaagttgtcggctggaagaagtttcaggcaaatggtactactttgaagaaaatggc ctgatgcaaacaggatgggtctttgttaacaaccattggtattatatggatcaggtgggggcaatgtgcattggctgggttgc agttgatggccattggtactacatggaccaatggggtgctatgtgtacaggctgggttagcgtcaatggacattggtatcatat ggaccaatggggagccatgcaaacaggctgggcactggttgattcaaattggtattacctgaatacggatggctcaatggcaat tggatgggtcgcagtgaacggccactggtattacatggatcaatggggagctatgcagacgggatgggctcttgttgatagcaa ctggtattatcttaacacagatggcagcatggcaatcggctgggtggcggttaatggacactggtactatatggatcaatgggg tgcaatgcagacaggctgggttctggtcggcagcgattggtactatttaaacacggatggatctatggcatcaagccaatggat tgatggctattatgttgatgcaagcggcaagatgaag SEQ ID NO: 15 is the nucleotide sequence encoding SEQ ID NO: 13 without
the signal sequence:
gcaggcgtttcagttccggcactggcacaacaagcagttagaacagaaagccaaacacaaatgtcatcagatccggaactggtc tatgtgaataactatagcagcacagcacaaagaagccagaactttaacagcaactggaaattctacttcggagatgcgggaaat gcacaaggcgcaacatttgatgatagcaaatgggaacaagtttcactgccgcatgattattcaatcagccaagaatatagcaaa tcaatggaagcagaatcaggctatcttggcggaggcacaggctggtatcgcaaaaattttacactgagcagcgatacacaaggc aaaagagtccgcattgattttgatggcgtctatatgaatgcaacagtttgggttaatggccatgaagttggcacacatccgtat ggctatacaagctttagctttgatatcacagattatgtgaaatatgatggcgaaaacacaattgcagtcaaagtcgtcaataat acaccgtcaagcagatggtattcaggctcaggcatttatagagatgtcgatctgacaatcacagatgatgttcatgttgatctg aacggcacaaaagttacaacaccgaacctggaaacagaaaaaggcagcacagtcaatacagatgttacagcaacagttgcgaat gattcagatgcagcaaaatcagttgcagttcgccatacagttttccgaaagatggcagcgcagatcaatcaattggcacagtc acaacaaatgcacaatcaattgcagcaggcgcaacagcagaaattcaagcaacggttccggtttcaaatcctgaactgtggtca gttgaaaatccgtcactgtatacagtcagaacagaagttctggtcgacggccaagtcacagatacatatgatacagaatatggc tttcgctatttttaactttgatagcaacacaggcttttcactgaatggcgaaaatatgaaactgaaaggcgtctgcatgcatcat gatcaaggctcacttggcgcagcagcatacgactcagcaattgatcgccaggtcaaaatcctgaaagaaatgggctgcaatagc attagagtcacacataatccggcagcacaagatctgattgatgcgtgcaatgaacaaggcattctggttgttgaagaagcgttt gatacttggacaagaccgaaaaatggcaacagcaacgattatagcgtctggtttaatcagacagttgcgagcgataatgaaatt ctggggagcgacaaatggcgaaacatgggcacaatttgatctggaaagcatgatctcacargattataatgcaccgtcagtcatt atgtggtcactgggcaatgaagttatggaaggcattagcggaggcacagatgcagaatatgaagcgacagcgacgaaactgatt aactgggcgtatgatgcggataatacacgtccgatgacaattggcgataacaaactgaaagcgaactggcagatctcaaaaaca tttgcgagactgctgacagaaaaaggcggaacagtgggctttaattatgcagatggcagagttctggattcatatcatagcagc aatagcaattggctgctgtatggctcagaaacagcatcagcgattaatagccgtggcatctattatagaacaacaggcggaggc caaacatcagataaacagctgacaagctatgataattcaaatgttggctggggagcaacagcatcaaatgcatggtatacagtt ctgacaagagattttgcggcaggcgaatatgtttggacaggctttgattatctgggcgaaccgacaccgtggaatggcacaggc ccaggcgcagttggctcatggccgtcaccgaaaaattcttattttggcattatcgatacagcaggcttcgcaaaagatagctat tattttatcagagccagtggaatgatgatgttacaacactgcatgttcttccggcatggaataataatgtcgtcagcaaagat tcatcaggcaatgttccggttgttgtttattcagatgcggcatcagtcgaactgttttttcaagcaaaaggcagcgatacaaaa acaagcctgggcaaaaaaacatttacacagaaaacaacagacgcaggctatacatatcagatctatgaaggctcagataaaaac agcacaacagacaaaaacctgtatctgacatggaatgttccgtatgcagatggaacagtttcagcagttgcgtataatagcaac ggccagaaaattacagatacagttggccagtcctcagttacaacaacaggcaaagcgtcaaaactgaaagcatcagcggatcat -continued aaaaaaattgcagcggatggcgaatcactgtcatatatcacagtcgatgtcacagatgcgaatggcaatattgttccggatgca
gaaaatcgcgtcaaatttacagttgaaggcgatggcgaactggttggcgttgataatggctcatcaccggatcatgattcatat
caagcggataaccgcaaagcattttcaggcaaagttctggcaattgtgaaaagcacaaaagaagctggcacaattacagttaca
gcatcagcagatggcctggattcagcatcagtcaaaatcacaacaacagcagtcgataatggcagcacagaaaaacaaatcgat
agctttaaaatgagccgcacatattatgttaaagttggcagcacaccggaactgccggaaaaaattgtcacacgctatacagat
ggcacatcagaagaactgcctgttacttgggatgcaattacagaagatcaaattgcagcagcaggctcatttcaagttaaaggc
acagtcaaaggcggatattcagttgcagtcaacgtcaacatgattgatgaagttggcggactgctgaattattcaacaaataca
gcagttggcgttgcaccggttctgccgacatcaagaccggcagttctgcaagatggcacagttatggatgttacatttccggtc
acatgggaagataaagcagcaagcgcatatgataaagcaggcacagtgacagtcaatggcacagcaaatgttctgggcaaagaa
attgcagttacagcgagcgttagagttcaggaagaaacaatcacaattggagattcagtttcagcggatgcactgaatctgaca
caaagcgttccggcagataaacaaagcgatacactgaacgcaattaaagatggctcaacaacaattagctcaaatacaagcgga
ggcgcaaatccgacagtttggagcaactatgactatagccaggatggcaatacgacagcggatatcatttttgaatatgcgaca
gaacaaagactgggccaaatcgttacacattttgcgagagatagctggtcaatgagatatcctgatgcaggcgctacagaaatt
tatgtctcaccggatggcacaaattgggcaaaactggatacaacagaaacaattggcacagaaagcggcaatgttaaaccgtat
acatatgattttgcaccggttggcgcaacatttgttaaatttcatctgacaaacagcacacaagcaacaggcacaacagcaaaa
gcatgcacaggcattacagaaattgaactgaaagttgcaacaggctcacgcacaacaaatacaacagcagaactgcaaacactg
acagttaatggcaaagaagttccgcaaacagcactggatagcaaagtttatacaacaccggcaattctggcagaaattgaagca
acagcgaaagataatgcaagcgttacagttcttccggcatataatgatgtcattcgcattattgtcgaaagcgaagatcatcaa
acacgcaatacatgaagtcagactgaatgaagcggaacaaacaacaccggattcagattcaagagattatccggttagcaaa
ctgacagcatcagcaggctcagaacaatcaacaacaggcgttgaaggaccggcatcaaatgcaaaagacggtgatgaatcaaca
ctgtggcatacaagatggtcagcaccggcagcaacatcagatcaactgtggtttacatatgaactggaagaagaaacggtactg
gacgcactgagatatctgccgagacaaggcacagcagatggccaaaataatggcagagttaatgaatatcgcgtcgaagttagc
acagatggcagcacatggacaacagttttcaacaggcaatgggaagatagccaagattggaaactggcagaatttacagaaccg
gttgcagcaaaatatgtcagactgacaggcgttcatacatatggctcatcagcagcaaacgtcgataaatacatgagcgcagca
gaaattagactgagaatggcagaaagcaaaacggatattgcagatgcagcaaatggcgttacagctacagcaccggattcaatt
gaagttgcaaaagcagatgcagaaaacccggttatgtttgatctgagcgatattgttgtcaaagcaggcgatacaacactgaga
tatggcgttgattatgtcattagctatgaaaacaacacagatttttggcacagcgaaactggtcattaaaggcattgatggctat
acaggcacactggaacatgaattcacaatcacgcagaaagccaaagtcatgacaggcatcacatggaatacaaaaccggaaaaa
gtcatttatacggaaggtgaaacgctggatgttacaggcctggttattaatgtcgtctatgatgatgatagcacagaagcagtt
gcatatagcgaagcaaatgcggatgaatttacattttcaccggcactggatacaaaactggcagcgacagataaaacagtcaca
gttacatataaaggcgcaagcctgatttatgatattacagtcaacccgaaaaaagtcgatccgacagatccggatcagcctgat
aaaccggatacaccggataatggcaatgataacggcaacgataataatggcaacggcaataacaacggcacagatgatggcaaa
aaagatccgggacaatcaggcgttacagataacaaaaatcagggcaataacagcaataatggaacagcagcaggcaataaagca
aatgcagcagcaaaaacaggcgatacagcaaatatgctgttgccgatgattgcagcaatgctggcaggcacagcagttgttggc
acaattcaattcgcagacgcagacgc SEQ ID NO: 16 is the nucleotide sequence encoding SEQ ID NO: 1:
aaagcagatagccaaacacaaatgtcatcagaaccggaacaagttgcggttaaagattatggctcaaatagcgcacgcacacag
aattttgatagcgattggaaatttaacctgggagatgttagcaatgcacagacaccgacatttgatgattcaaaatggcgcaca
ctgtcactgccgcatgattatagcatcgaacaggaatattcacaatcactggaagcagaatcaggctatcttccgggaggcgtt
ggctggtatcgcaaaaattttacactgggcgaagaagcgaaaggcaaacgcattcgcattgattttgatggcgtctatatgaat
gcaacagtctatgtgaatggcaaagaagttggcacacatccgtatggctatacaccgtttagctttgatatcacagattatatc -continued

```
agctatgataaagaaaacacaattgcggtcaaagtcgatcatcaaacaccgtcatcaagatggtattcaggcagcggcatttat
agatcagtcaacctgacaacaacaaatgatgtccatgtcgatctgaatggcattaaagtcgaaagcaacaacctggaaaagaa
gcaggcaaaacagtcaacacagatgtgaaaacaacagttgtgaacggctcaaaagaagcgaaaaacatcacaattacacataca
gtctttaaaaaaggcgaaaaaccggataaagcgatcggcacatttacaacagaagcgcaagaaattggcgcaggcaaaaaaaca
gaaatcagcgcaacagtcccggttaaaaatccggaactgtggtcagttgaaaatccggcactgtatacaattcgcacagaagtt
aaagcaggcgataaactgctggatagctatgatacagaatatggctttcattatctgaactttgatacagaaacaggctttcag
ctgaatggcaaaaacgttaaactgaaaggcgtttgcatgcatcatgatcaaggcgcacttggcgcagttgcaaatagaagagca
attgaacgccaagtcgaaattctgcaagaaatgggctgcaatagcattagagtcacacataatccggcaagcaaagatctgatt
gaagtctgcaacgaaaaaggcattctggtcattgaagaagttttttgacggctggcatagagcaaaaaatggcaacagcaacgat
tatagcgtctggtttgaaaaagcgatcgaagaagataacgcgattctgggaaaagaagcggatatgacttgggcagaatatgat
ctgaaagcgattatgaaacgcgatcaaaatgcaccgagcattattgaatggtcactgggcaatgaaattcaagaaggcgcaggc
ggatcaggctatgcagaaagagcggataaactgatcaaatgggcgaaagaagcagacgcaacaaaaacactgacaattggcagc
aatgcagttaaaagaggcgattgggaacaagttagcatcggcgataaacttacaaaagcaggcggaacatcaggcacaaattat
tcagatggcgcatcatatgataaaattcataaagaacatccggattggaaactgtatggctcagaaacagcatcatcagttaat
agccgtggcatttattcagttacaggcaatcaagaagcaacaagcgatcaacaactgacagcgtatgataatagcagagttaat
tggggagcactggcatcacaagcatggtatgatgttatccagagagattttgtcgcaggcgaatatgtttggacaggctttgat
tatatcggcgaaccgacaccgtggaatggcacagatccgggagcaaaaggcacatggccgtcaccgaaaaacagctactttggc
attatcgatacagcaggctttccgaaagattcatattattttttatcagagccagtggaatgaagaagtcaatacactgcacgtt
cttccggcatggaatgaagatgtcgtcaaaaaaaactcagatggcacagttccggttgttgtttattcagatgcgaaagaagtc
gaactgttttttacaccggcaaatggcggagaaaaaaaaagcctgggaaaaaaaacatttaaaacagaaacaacaaaagctggc
tatagctatcaagttctggaaaacggcaaaaaaaaacataaagatctgtatatggaatggcaagttccgtatgaagcaggcaca
cttgaagcagttgcgaaagatgcaaaaggcaacgtcattaaagatacagaaggcagaagcgtcgttaaaacaacaggcgaagaa
gcaaaactgtcagcaaaaacggatcgcaatagcattcaagcagatggcaaagatctgtcatatattacagtcgatgtcacagat
aaagatggcaatattgttccggatgcagcaaatagagtcacatttgatgtccaaggcgcaggaaaactggttggcgttgataat
ggctcatcaccggatcatgatagctataaagcggataaccgcaaagcattttcaggcaaagtctctggcaattgttcagtcaaca
gaaaaagcaggcgaaattacagttacagcaaaagcagatggcctggaatcaagcacagtcaaaatcacaacaacaccggttaaa
gaagaaccgagcgaaagatatgtcgaaagctataaatacagcaaaagctattatgtgaaaacaggcacaaaaccgcaactgccg
aaaaaaattgaagcgcagtatagcgatcgcacaaaagaggatgttgcggtcaaatgggatgaaatctcagatgaacaaattagc
aaaacaggcagctttacagttgaaggcacagttggcaaaagagatatcacagtcaacattaacatgatcgatgatgttgcagca
ctgctgaattattcaggcgcaacacaaaaaggcgttaaaccgcaacttccggatgttagaccggcagttctgcctgatggcaca
gtcctggcagcatcatttccggttcagtgggatgaaaaagatgcggatacatttcagaaaccggatgaaattgttacagttaac
ggcagcgcagatatctttggcaaaacaattccggttacagcaagcattagagtgcagaaagaagatatcaaaattggcagcagc
gttacaaatgttgcaaaactgagccaaaatattcaaggcagcgatacactggaagcaatcaaagatggcaaaacagaaatgagc
ctgaataatgatggcggaccgaatgaatcagcatggtcaaattgggatgcatcacagaaaggcacaaaagaagccgaactgaca
tttacatttgatacacagcaacgcattggcgaaattgtcattcattttgcgaaagataacaactcaatcagatttccggatgct
ggcacaacagaaatc
```

SEQ ID NO: 17 is the nucleotide sequence encoding SEQ ID NO: 2:
```
gcaggcgtttcagttccggcactggcacaacaagcagttagaacagaaagccaaacacaaatgtcatcagatccggaactggtc
tatgtgaataactatagcagcacagcacaaagaagccagaactttaacagcaactggaaattctacttcggagatgcgggaaat
gcacaaggcgcaacatttgatgatagcaaatgggaacaagtttcactgccgcatgattattcaatcagccaagaatatagcaaa
tcaatggaagcagaatcaggctatcttggcggaggcacaggctggtatcgcaaaaattttacactgagcagcgatacacaaggc
```

-continued

```
aaaagagtccgcattgattttgatggcgtctatatgaatgcaacagtttgggttaatggccatgaagttggcacacatccgtat
ggctatacaagctttagctttgatatcacagattatgtgaaatatgatggcgaaaacacaattgcagtcaaagtcgtcaataat
acaccgtcaagcagatggtattcaggctcaggcatttatagagatgtcgatctgacaatcacagatgatgttcatgttgatctg
aacggcacaaaagttacaacaccgaacctggaaacagaaaaaggcagcacagtcaatacagatgttacagcaacagttgcgaat
gattcagatgcagcaaaatcagttgcagttcgccatacagttttccgaaagatggcagcgcagatcaatcaattggcacagtc
acaacaaatgcacaatcaattgcagcaggcgcaacagcagaaattcaagcaacggttccggtttcaaatcctgaactgtggtca
gttgaaaatccgtcactgtatacagtcagaacagaagttctggtcgacggccaagtcacagatacatatgatacagaatatggc
tttcgctattttaactttgatagcaacacaggcttttcactgaatggcgaaaatatgaaactgaaaggcgtctgcatgcatcat
gatcaaggctcacttggcgcagcagcatacgactcagcaattgatcgccaggtcaaaatcctgaaagaaatgggctgcaatagc
attagagtcacacataatccggcagcacaagatctgattgatgcgtgcaatgaacaaggcattctggttgttgaagaagcgttt
gatacttggacaagaccgaaaaatggcaacagcaacgattatagcgtctggtttaatcagacagttgcgagcgataatgaaatt
ctgggagcgacaaatggcgaaacatgggcacaatttgatctggaaagcatgatctcacgcgattataatgcaccgtcagtcatt
atgtggtcactgggcaatgaagttatggaaggcattagcggaggcacagatgcagaatatgaagcgacagcgacgaaactgatt
aactgggcgtatgatgcggataatacacgtccgatgacaattggcgataacaaactgaaagcgaactggcagatctcaaaaaca
tttgcgagactgctgacagaaaaaggcggaacagtgggctttaattatgcagatggcagagttctggattcatatcatagcagc
aatagcaattggctgctgtatggctcagaaacagcatcagcgattaatagccgtggcatctattatagaacaacaggcggaggc
caaacatcagataaacagctgacaagctatgataattcaaatgttggctggggagcaacagcatcaaatgcatggtatacagtt
ctgacaagagattttgcggcaggcgaatatgtttggacaggctttgattatctgggcgaaccgacaccgtggaatggcacaggc
tcaggcgcagttggctcatggccgtcaccgaaaaattcttattttggcattatcgatacagcaggcttcgcaaaagatagctat
tattttatcagagccagtggaatgatgatgttacaacactgcatgttcttccggcatggaataataatgtcgtcagcaaagat
tcatcaggcaatgttccggttgttgtttattcagatgcggcatcagtcgaactgtttttcaagcaaaaggcagcgatacaaaa
acaagcctgggcaaaaaaacatttacacagaaaacaacagacgcaggctatacatatcagatctatgaaggctcagataaaaac
agcacaacagacaaaaacctgtatctgacatggaatgttccgtatgcagatggaacagtttcagcagttgcgtataatagcaac
ggccagaaaattacagatacagttggccagtcctcagttacaacaacaggcaaagcgtcaaaactgaaagcatcagcggatcat
aaaaaaattgcagcggatggcgaatcactgtcatatatcacagtcgatgtcacagatgcgaatggcaatattgttccggatgca
gaaaatcgcgtcaaatttacagttgaaggcgatggcgaactggttggcgttgataatggctcatcaccggatcatgattcatat
caagcggataaccgcaaagcattttcaggcaaagttctggcaattgtgaaaagcacaaaagaagctggcacaattacagttaca
gcatcagcagatggcctggattcagcatcagtcaaaatcacaacaacagcagtcgataatggcagcacagaaaaacaaatcgat
agctttaaaatgagccgcacatattatgttaaagttggcagcacaccggaactgccggaaaaaattgtcacacgctatacagat
ggcacatcagaagaactgcctgttacttgggatgcaattacagaagatcaaattgcagcagcaggctcatttcaagttaaaggc
acagtcaaaggcggatattcagttgcagtcaacgtcaacatgattgatgaagttggcggactgctgaattattcaacaaataca
gcagttggcgttgcaccggttctgccgacatcaagaccggcagttctgcaagatggcacagttatggatgttacatttccggtc
acatgggaagataaagcagcaagcgcatatgataaagcaggcacagtgacagtcaatggcacagcaaatgttctgggcaaagaa
attgcagttacagcgagcgttagagttcaggaagaaacaatcacaattggagattcagtttcagcggatgcactgaatctgaca
caaagcgttccggcagataaacaaagcgatacactgaacgcaattaaagatggctcaacaacaattagctcaaatacaagcgga
ggcgcaaatccgacagtttggagcaactatgactatagccaggatggcaatacgacagcggatatcattttgaatatgcgaca
gaacaaagactgggccaaatcgttacacattttgcgagagatagctggtcaatgagatatcctgatgcaggcgctacagaaatt
tatgtc
```

The invention claimed is:

1. A method for producing a food product, the method comprising:
   providing a substrate comprising lactose at a concentration of 5% w/w or greater;
   adding a polypeptide to the substrate comprising lactose, the polypeptide having transgalactosylating activity, and the polypeptide selected from the group consisting of:
   a. a polypeptide comprising an amino acid sequence having at least 90% sequence identity to the amino acid sequence of SEQ ID NO: 1,
   b. a polypeptide comprising an amino acid sequence having at least 90% sequence identity to the amino acid sequence of SEQ ID NO: 2,
   c. a polypeptide encoded by a polynucleotide that hybridizes under high stringency conditions of 0.1 SSC (0.15 M NaCl, pH 7.0) at 65° C. with,
      i) the nucleic acid sequence comprised in SEQ ID NO: 10 encoding SEQ ID NO: 1,
      ii) the cDNA sequence of i), or
      iii) the complementary strand of i) or ii),
   d. a polypeptide encoded by a polynucleotide that hybridizes under high stringency conditions of 0.1 SSC (0.15 M NaCl, pH 7.0) at 65° C. with,
      i) the nucleic acid sequence comprised in SEQ ID NO: 11 encoding SEQ ID NO: 2,
      ii) the cDNA sequence of i), or
      iii) the complementary strand of i) or ii),
   e. a polypeptide comprising a conservative substitution, deletion or insertion of in a sequence resulting in a sequence having at least 90% identity to SEQ ID NO: 1, or
   f. a polypeptide comprising a conservative substitution, deletion or insertion of amino acids in a sequence resulting in a sequence having at least 90% identity to SEQ ID NO: 2,
   provided that the polypeptide of above items a, c, and e, at the most has a length of 1806 amino acids and provided that the polypeptide of above items b, d, and f at the most has a length of 1767 amino acids; and
   producing the food product that contains galacto-oligosacharides.

2. A method of producing a dairy product, the method comprising:
   providing a milk-based substrate comprising lactose at a concentration of 5% w/w or greater;
   adding a polypeptide to the substrate comprising lactose, the polypeptide having transgalactosylating activity, and the polypeptide selected from the group consisting of:
   a. a polypeptide comprising an amino acid sequence having at least 90% sequence identity to the amino acid sequence of SEQ ID NO: 1,
   b. a polypeptide comprising an amino acid sequence having at least 90% sequence identity to the amino acid sequence of SEQ ID NO: 2,
   c. a polypeptide encoded by a polynucleotide that hybridizes under high stringency conditions of 0.1 SSC (0.15 M NaCl, pH 7.0) at 65° C. with, i) the nucleic acid sequence comprised in SEQ ID NO: 10 encoding SEQ ID NO: 1,
ii) the cDNA sequence of i), or
iii) the complementary strand of i) or ii),
d. a polypeptide encoded by a polynucleotide that hybridizes under high stringency conditions of 0.1 SSC (0.15 M NaCl, pH 7.0) at 65° C. with,
i) the nucleic acid sequence comprised in SEQ ID NO: 11 encoding SEQ ID NO: 2,
ii) the cDNA sequence of i), or
iii) the complementary strand of i) or ii),
e. a polypeptide comprising a conservative substitution, deletion or insertion of in a sequence resulting in a sequence having at least 90% identity to SEQ ID NO:1, or
f. a polypeptide comprising a conservative substitution, deletion or insertion of amino acids in a sequence resulting in a sequence having at least 90% identity to SEQ ID NO: 2,
provided that the polypeptide of above items a, c, and e, at the most has a length of 1806 amino acids and provided that the polypeptide of above items b, d, and f at the most has a length of 1767 amino acids; and
producing the dairy product that contains galacto-oligossacharides.

3. The method of claim 1, further comprising treating the substrate with a hydrolysing beta-galactosidase.

\* \* \* \* \*

SEQUENCE LISTING

<160> NUMBER OF SEQ ID NOS: 17

<210> SEQ ID NO 1
<211> LENGTH: 1125
<212> TYPE: PRT
<213> ORGANISM: Ruminococcus hansenii

<400> SEQUENCE: 1

```
Lys Ala Asp Ser Gln Thr Gln Met Ser Ser Glu Pro Glu Gln Val Ala
 1               5                  10                  15

Val Lys Asp Tyr Gly Ser Asn Ser Ala Arg Thr Gln Asn Phe Asp Ser
            20                  25                  30

Asp Trp Lys Phe Asn Leu Gly Asp Val Ser Asn Ala Gln Thr Pro Thr
        35                  40                  45

Phe Asp Asp Ser Lys Trp Arg Thr Leu Ser Leu Pro His Asp Tyr Ser
    50                  55                  60

Ile Glu Gln Glu Tyr Ser Gln Ser Leu Glu Ala Glu Ser Gly Tyr Leu
 65                  70                  75                  80

Pro Gly Gly Val Gly Trp Tyr Arg Lys Asn Phe Thr Leu Gly Glu Glu
                85                  90                  95

Ala Lys Gly Lys Arg Ile Arg Ile Asp Phe Asp Gly Val Tyr Met Asn
            100                 105                 110

Ala Thr Val Tyr Val Asn Gly Lys Glu Val Gly Thr His Pro Tyr Gly
        115                 120                 125

Tyr Thr Pro Phe Ser Phe Asp Ile Thr Asp Tyr Ile Ser Tyr Asp Lys
    130                 135                 140

Glu Asn Thr Ile Ala Val Lys Val Asp His Gln Thr Pro Ser Ser Arg
145                 150                 155                 160

Trp Tyr Ser Gly Ser Gly Ile Tyr Arg Ser Val Asn Leu Thr Thr Thr
                165                 170                 175

Asn Asp Val His Val Asp Leu Asn Gly Ile Lys Val Glu Ser Asn Asn
            180                 185                 190

Leu Glu Lys Glu Ala Gly Lys Thr Val Asn Thr Asp Val Lys Thr Thr
        195                 200                 205

Val Val Asn Gly Ser Lys Glu Ala Lys Asn Ile Thr Ile Thr His Thr
    210                 215                 220

Val Phe Lys Lys Gly Glu Lys Pro Asp Lys Ala Ile Gly Thr Phe Thr
225                 230                 235                 240

Thr Glu Ala Gln Glu Ile Gly Ala Gly Lys Lys Thr Glu Ile Ser Ala
                245                 250                 255

Thr Val Pro Val Lys Asn Pro Glu Leu Trp Ser Val Glu Asn Pro Ala
            260                 265                 270

Leu Tyr Thr Ile Arg Thr Glu Val Lys Ala Gly Asp Lys Leu Leu Asp
        275                 280                 285

Ser Tyr Asp Thr Glu Tyr Gly Phe His Tyr Leu Asn Phe Asp Thr Glu
    290                 295                 300

Thr Gly Phe Gln Leu Asn Gly Lys Asn Val Lys Leu Lys Gly Val Cys
305                 310                 315                 320

Met His His Asp Gln Gly Ala Leu Gly Ala Val Ala Asn Arg Arg Ala
                325                 330                 335

Ile Glu Arg Gln Val Glu Ile Leu Gln Glu Met Gly Cys Asn Ser Ile
            340                 345                 350

Arg Val Thr His Asn Pro Ala Ser Lys Asp Leu Ile Glu Val Cys Asn
        355                 360                 365
```

-continued

```
Glu Lys Gly Ile Leu Val Ile Glu Glu Val Phe Asp Gly Trp His Arg
    370             375             380
Ala Lys Asn Gly Asn Ser Asn Asp Tyr Ser Val Trp Phe Glu Lys Ala
385                 390             395                 400
Ile Glu Glu Asp Asn Ala Ile Leu Gly Lys Glu Ala Asp Met Thr Trp
                405             410                 415
Ala Glu Tyr Asp Leu Lys Ala Ile Met Lys Arg Asp Gln Asn Ala Pro
            420             425             430
Ser Ile Ile Glu Trp Ser Leu Gly Asn Glu Ile Gln Glu Gly Ala Gly
        435             440             445
Gly Ser Gly Tyr Ala Glu Arg Ala Asp Lys Leu Ile Lys Trp Ala Lys
    450             455             460
Glu Ala Asp Ala Thr Lys Thr Leu Thr Ile Gly Ser Asn Ala Val Lys
465             470             475                 480
Arg Gly Asp Trp Glu Gln Val Ser Ile Gly Asp Lys Leu Thr Lys Ala
                485             490             495
Gly Gly Thr Ser Gly Thr Asn Tyr Ser Asp Gly Ala Ser Tyr Asp Lys
            500             505             510
Ile His Lys Glu His Pro Asp Trp Lys Leu Tyr Gly Ser Glu Thr Ala
        515             520             525
Ser Ser Val Asn Ser Arg Gly Ile Tyr Ser Val Thr Gly Asn Gln Glu
    530             535             540
Ala Thr Ser Asp Gln Gln Leu Thr Ala Tyr Asp Asn Ser Arg Val Asn
545             550             555                 560
Trp Gly Ala Leu Ala Ser Gln Ala Trp Tyr Asp Val Ile Gln Arg Asp
                565             570             575
Phe Val Ala Gly Glu Tyr Val Trp Thr Gly Phe Asp Tyr Ile Gly Glu
            580             585             590
Pro Thr Pro Trp Asn Gly Thr Asp Pro Gly Ala Lys Gly Thr Trp Pro
        595             600             605
Ser Pro Lys Asn Ser Tyr Phe Gly Ile Ile Asp Thr Ala Gly Phe Pro
    610             615             620
Lys Asp Ser Tyr Tyr Phe Tyr Gln Ser Gln Trp Asn Glu Glu Val Asn
625             630             635                 640
Thr Leu His Val Leu Pro Ala Trp Asn Glu Asp Val Val Lys Lys Asn
                645             650             655
Ser Asp Gly Thr Val Pro Val Val Tyr Ser Asp Ala Lys Glu Val
            660             665             670
Glu Leu Phe Phe Thr Pro Ala Asn Gly Gly Glu Lys Lys Ser Leu Gly
        675             680             685
Lys Lys Thr Phe Lys Thr Glu Thr Thr Lys Ala Gly Tyr Ser Tyr Gln
    690             695             700
Val Leu Glu Asn Gly Lys Lys His Lys Asp Leu Tyr Met Glu Trp
705             710             715                 720
Gln Val Pro Tyr Glu Ala Gly Thr Leu Glu Ala Val Ala Lys Asp Ala
                725             730             735
Lys Gly Asn Val Ile Lys Asp Thr Glu Gly Arg Ser Val Val Lys Thr
            740             745             750
Thr Gly Glu Glu Ala Lys Leu Ser Ala Lys Thr Asp Arg Asn Ser Ile
        755             760             765
Gln Ala Asp Gly Lys Asp Leu Ser Tyr Ile Thr Val Asp Val Thr Asp
    770             775             780
Lys Asp Gly Asn Ile Val Pro Asp Ala Ala Asn Arg Val Thr Phe Asp
```

```
                        785                 790                 795                 800
Val Gln Gly Ala Gly Lys Leu Val Gly Val Asp Asn Gly Ser Ser Pro
                    805                 810                 815

Asp His Asp Ser Tyr Lys Ala Asp Asn Arg Lys Ala Phe Ser Gly Lys
                    820                 825                 830

Val Leu Ala Ile Val Gln Ser Thr Glu Lys Ala Gly Glu Ile Thr Val
                    835                 840                 845

Thr Ala Lys Ala Asp Gly Leu Glu Ser Ser Thr Val Lys Ile Thr Thr
            850                 855                 860

Thr Pro Val Lys Glu Glu Pro Ser Glu Arg Tyr Val Glu Ser Tyr Lys
865                 870                 875                 880

Tyr Ser Lys Ser Tyr Tyr Val Lys Thr Gly Thr Lys Pro Gln Leu Pro
                    885                 890                 895

Lys Lys Ile Glu Ala Gln Tyr Ser Asp Arg Thr Lys Glu Asp Val Ala
                    900                 905                 910

Val Lys Trp Asp Glu Ile Ser Asp Glu Gln Ile Ser Lys Thr Gly Ser
                    915                 920                 925

Phe Thr Val Glu Gly Thr Val Gly Lys Arg Asp Ile Thr Val Asn Ile
            930                 935                 940

Asn Met Ile Asp Asp Val Ala Ala Leu Leu Asn Tyr Ser Gly Ala Thr
945                 950                 955                 960

Gln Lys Gly Val Lys Pro Gln Leu Pro Asp Val Arg Pro Ala Val Leu
                    965                 970                 975

Pro Asp Gly Thr Val Leu Ala Ala Ser Phe Pro Val Gln Trp Asp Glu
                    980                 985                 990

Lys Asp Ala Asp Thr Phe Gln Lys Pro Asp Glu Ile Val Thr Val Asn
                    995                1000                1005

Gly Ser Ala Asp Ile Phe Gly Lys Thr Ile Pro Val Thr Ala Ser
            1010                1015                1020

Ile Arg Val Gln Lys Glu Asp Ile Lys Ile Gly Ser Ser Val Thr
            1025                1030                1035

Asn Val Ala Lys Leu Ser Gln Asn Ile Gln Gly Ser Asp Thr Leu
            1040                1045                1050

Glu Ala Ile Lys Asp Gly Lys Thr Glu Met Ser Leu Asn Asn Asp
            1055                1060                1065

Gly Gly Pro Asn Glu Ser Ala Trp Ser Asn Trp Asp Ala Ser Gln
            1070                1075                1080

Lys Gly Thr Lys Glu Ala Glu Leu Thr Phe Thr Phe Asp Thr Gln
            1085                1090                1095

Gln Arg Ile Gly Glu Ile Val Ile His Phe Ala Lys Asp Asn Asn
            1100                1105                1110

Ser Ile Arg Phe Pro Asp Ala Gly Thr Thr Glu Ile
            1115                1120                1125

<210> SEQ ID NO 2
<211> LENGTH: 1150
<212> TYPE: PRT
<213> ORGANISM: Ruminococcus lactaris

<400> SEQUENCE: 2

Ala Gly Val Ser Val Pro Ala Leu Ala Gln Gln Ala Val Arg Thr Glu
1               5                   10                  15

Ser Gln Thr Gln Met Ser Ser Asp Pro Glu Leu Val Tyr Val Asn Asn
            20                  25                  30
```

-continued

```
Tyr Ser Ser Thr Ala Gln Arg Ser Gln Asn Phe Asn Ser Asn Trp Lys
             35                  40                  45

Phe Tyr Phe Gly Asp Ala Gly Asn Ala Gln Gly Ala Thr Phe Asp Asp
 50                  55                  60

Ser Lys Trp Glu Gln Val Ser Leu Pro His Asp Tyr Ser Ile Ser Gln
 65                  70                  75                  80

Glu Tyr Ser Lys Ser Met Glu Ala Glu Ser Gly Tyr Leu Gly Gly Gly
                 85                  90                  95

Thr Gly Trp Tyr Arg Lys Asn Phe Thr Leu Ser Ser Asp Thr Gln Gly
                100                 105                 110

Lys Arg Val Arg Ile Asp Phe Asp Gly Val Tyr Met Asn Ala Thr Val
                115                 120                 125

Trp Val Asn Gly His Glu Val Gly Thr His Pro Tyr Gly Tyr Thr Ser
130                 135                 140

Phe Ser Phe Asp Ile Thr Asp Tyr Val Lys Tyr Asp Gly Glu Asn Thr
145                 150                 155                 160

Ile Ala Val Lys Val Asn Asn Thr Pro Ser Ser Arg Trp Tyr Ser
                165                 170                 175

Gly Ser Gly Ile Tyr Arg Asp Val Asp Leu Thr Ile Thr Asp Asp Val
                180                 185                 190

His Val Asp Leu Asn Gly Thr Lys Val Thr Thr Pro Asn Leu Glu Thr
                195                 200                 205

Glu Lys Gly Ser Thr Val Asn Thr Asp Val Thr Ala Thr Val Ala Asn
                210                 215                 220

Asp Ser Asp Ala Ala Lys Ser Val Ala Val Arg His Thr Val Phe Pro
225                 230                 235                 240

Lys Asp Gly Ser Ala Asp Gln Ser Ile Gly Thr Val Thr Thr Asn Ala
                245                 250                 255

Gln Ser Ile Ala Ala Gly Ala Thr Ala Glu Ile Gln Ala Thr Val Pro
                260                 265                 270

Val Ser Asn Pro Glu Leu Trp Ser Val Glu Asn Pro Ser Leu Tyr Thr
                275                 280                 285

Val Arg Thr Glu Val Leu Val Asp Gly Gln Val Thr Asp Thr Tyr Asp
290                 295                 300

Thr Glu Tyr Gly Phe Arg Tyr Phe Asn Phe Asp Ser Asn Thr Gly Phe
305                 310                 315                 320

Ser Leu Asn Gly Glu Asn Met Lys Leu Lys Gly Val Cys Met His His
                325                 330                 335

Asp Gln Gly Ser Leu Gly Ala Ala Ala Tyr Asp Ser Ala Ile Asp Arg
                340                 345                 350

Gln Val Lys Ile Leu Lys Glu Met Gly Cys Asn Ser Ile Arg Val Thr
                355                 360                 365

His Asn Pro Ala Ala Gln Asp Leu Ile Asp Ala Cys Asn Glu Gln Gly
                370                 375                 380

Ile Leu Val Val Glu Glu Ala Phe Asp Thr Trp Thr Arg Pro Lys Asn
385                 390                 395                 400

Gly Asn Ser Asn Asp Tyr Ser Val Trp Phe Asn Gln Thr Val Ala Ser
                405                 410                 415

Asp Asn Glu Ile Leu Gly Ala Thr Asn Gly Thr Trp Ala Gln Phe
                420                 425                 430

Asp Leu Glu Ser Met Ile Ser Arg Asp Tyr Asn Ala Pro Ser Val Ile
                435                 440                 445

Met Trp Ser Leu Gly Asn Glu Val Met Glu Gly Ile Ser Gly Gly Thr
```

-continued

```
            450                 455                 460
Asp Ala Glu Tyr Glu Ala Thr Ala Thr Lys Leu Ile Asn Trp Ala Tyr
465                 470                 475                 480

Asp Ala Asp Asn Thr Arg Pro Met Thr Ile Gly Asp Asn Lys Leu Lys
                485                 490                 495

Ala Asn Trp Gln Ile Ser Lys Thr Phe Ala Arg Leu Leu Thr Glu Lys
            500                 505                 510

Gly Gly Thr Val Gly Phe Asn Tyr Ala Asp Gly Arg Val Leu Asp Ser
        515                 520                 525

Tyr His Ser Ser Asn Ser Asn Trp Leu Leu Tyr Gly Ser Glu Thr Ala
    530                 535                 540

Ser Ala Ile Asn Ser Arg Gly Ile Tyr Tyr Arg Thr Thr Gly Gly Gly
545                 550                 555                 560

Gln Thr Ser Asp Lys Gln Leu Thr Ser Tyr Asp Asn Ser Asn Val Gly
                565                 570                 575

Trp Gly Ala Thr Ala Ser Asn Ala Trp Tyr Thr Val Leu Thr Arg Asp
            580                 585                 590

Phe Ala Ala Gly Glu Tyr Val Trp Thr Gly Phe Asp Tyr Leu Gly Glu
        595                 600                 605

Pro Thr Pro Trp Asn Gly Thr Gly Ser Gly Ala Val Gly Ser Trp Pro
    610                 615                 620

Ser Pro Lys Asn Ser Tyr Phe Gly Ile Ile Asp Thr Ala Gly Phe Ala
625                 630                 635                 640

Lys Asp Ser Tyr Tyr Phe Tyr Gln Ser Gln Trp Asn Asp Asp Val Thr
                645                 650                 655

Thr Leu His Val Leu Pro Ala Trp Asn Asn Asn Val Val Ser Lys Asp
            660                 665                 670

Ser Ser Gly Asn Val Pro Val Val Val Tyr Ser Asp Ala Ala Ser Val
        675                 680                 685

Glu Leu Phe Phe Gln Ala Lys Gly Ser Asp Thr Lys Thr Ser Leu Gly
    690                 695                 700

Lys Lys Thr Phe Thr Gln Lys Thr Thr Asp Ala Gly Tyr Thr Tyr Gln
705                 710                 715                 720

Ile Tyr Glu Gly Ser Asp Lys Asn Ser Thr Thr Asp Lys Asn Leu Tyr
                725                 730                 735

Leu Thr Trp Asn Val Pro Tyr Ala Asp Gly Thr Val Ser Ala Val Ala
            740                 745                 750

Tyr Asn Ser Asn Gly Gln Lys Ile Thr Asp Thr Val Gly Gln Ser Ser
        755                 760                 765

Val Thr Thr Thr Gly Lys Ala Ser Lys Leu Lys Ala Ser Ala Asp His
    770                 775                 780

Lys Lys Ile Ala Ala Asp Gly Glu Ser Leu Ser Tyr Ile Thr Val Asp
785                 790                 795                 800

Val Thr Asp Ala Asn Gly Asn Ile Val Pro Asp Ala Glu Asn Arg Val
                805                 810                 815

Lys Phe Thr Val Glu Gly Asp Gly Glu Leu Val Gly Val Asp Asn Gly
            820                 825                 830

Ser Ser Pro Asp His Asp Ser Tyr Gln Ala Asp Asn Arg Lys Ala Phe
        835                 840                 845

Ser Gly Lys Val Leu Ala Ile Val Lys Ser Thr Lys Glu Ala Gly Thr
    850                 855                 860

Ile Thr Val Thr Ala Ser Ala Asp Gly Leu Asp Ser Ala Ser Val Lys
865                 870                 875                 880
```

```
Ile Thr Thr Thr Ala Val Asp Asn Gly Ser Thr Glu Lys Gln Ile Asp
            885                 890                 895

Ser Phe Lys Met Ser Arg Thr Tyr Tyr Val Lys Val Gly Ser Thr Pro
            900                 905                 910

Glu Leu Pro Glu Lys Ile Val Thr Arg Tyr Thr Asp Gly Thr Ser Glu
            915                 920                 925

Glu Leu Pro Val Thr Trp Asp Ala Ile Thr Glu Asp Gln Ile Ala Ala
            930                 935                 940

Ala Gly Ser Phe Gln Val Lys Gly Thr Val Lys Gly Tyr Ser Val
945                 950                 955                 960

Ala Val Asn Val Asn Met Ile Asp Glu Val Gly Gly Leu Leu Asn Tyr
            965                 970                 975

Ser Thr Asn Thr Ala Val Gly Val Ala Pro Val Leu Pro Thr Ser Arg
            980                 985                 990

Pro Ala Val Leu Gln Asp Gly Thr Val Met Asp Val Thr Phe Pro Val
            995                 1000                1005

Thr Trp Glu Asp Lys Ala Ala Ser Ala Tyr Asp Lys Ala Gly Thr
            1010                1015                1020

Val Thr Val Asn Gly Thr Ala Asn Val Leu Gly Lys Glu Ile Ala
            1025                1030                1035

Val Thr Ala Ser Val Arg Val Gln Glu Glu Thr Ile Thr Ile Gly
            1040                1045                1050

Asp Ser Val Ser Ala Asp Ala Leu Asn Leu Thr Gln Ser Val Pro
            1055                1060                1065

Ala Asp Lys Gln Ser Asp Thr Leu Asn Ala Ile Lys Asp Gly Ser
            1070                1075                1080

Thr Thr Ile Ser Ser Asn Thr Ser Gly Gly Ala Asn Pro Thr Val
            1085                1090                1095

Trp Ser Asn Tyr Asp Tyr Ser Gln Asp Gly Asn Thr Thr Ala Asp
            1100                1105                1110

Ile Ile Phe Glu Tyr Ala Thr Glu Gln Arg Leu Gly Gln Ile Val
            1115                1120                1125

Thr His Phe Ala Arg Asp Ser Trp Ser Met Arg Tyr Pro Asp Ala
            1130                1135                1140

Gly Ala Thr Glu Ile Tyr Val
            1145                1150

<210> SEQ ID NO 3
<211> LENGTH: 91
<212> TYPE: PRT
<213> ORGANISM: Ruminococcus hansenii

<400> SEQUENCE: 3

Val Asn Trp Gly Ala Leu Ala Ser Gln Ala Trp Tyr Asp Val Ile Gln
1               5                   10                  15

Arg Asp Phe Val Ala Gly Glu Tyr Val Trp Thr Gly Phe Asp Tyr Ile
            20                  25                  30

Gly Glu Pro Thr Pro Trp Asn Gly Thr Asp Pro Gly Ala Lys Gly Thr
        35                  40                  45

Trp Pro Ser Pro Lys Asn Ser Tyr Phe Gly Ile Ile Asp Thr Ala Gly
    50                  55                  60

Phe Pro Lys Asp Ser Tyr Tyr Phe Tyr Gln Ser Gln Trp Asn Glu Glu
65                  70                  75                  80

Val Asn Thr Leu His Val Leu Pro Ala Trp Asn
                85                  90
```

<210> SEQ ID NO 4
<211> LENGTH: 71
<212> TYPE: PRT
<213> ORGANISM: Ruminococcus hansenii

<400> SEQUENCE: 4

Ala Gly Glu Tyr Val Trp Thr Gly Phe Asp Tyr Ile Gly Glu Pro Thr
1               5                   10                  15

Pro Trp Asn Gly Thr Asp Pro Gly Ala Lys Gly Thr Trp Pro Ser Pro
            20                  25                  30

Lys Asn Ser Tyr Phe Gly Ile Ile Asp Thr Ala Gly Phe Pro Lys Asp
        35                  40                  45

Ser Tyr Tyr Phe Tyr Gln Ser Gln Trp Asn Glu Glu Val Asn Thr Leu
    50                  55                  60

His Val Leu Pro Ala Trp Asn
65                  70

<210> SEQ ID NO 5
<211> LENGTH: 58
<212> TYPE: PRT
<213> ORGANISM: Ruminococcus hansenii

<400> SEQUENCE: 5

Ala Gly Glu Tyr Val Trp Thr Gly Phe Asp Tyr Ile Gly Glu Pro Thr
1               5                   10                  15

Pro Trp Asn Gly Thr Asp Pro Gly Ala Lys Gly Thr Trp Pro Ser Pro
            20                  25                  30

Lys Asn Ser Tyr Phe Gly Ile Ile Asp Thr Ala Gly Phe Pro Lys Asp
        35                  40                  45

Ser Tyr Tyr Phe Tyr Gln Ser Gln Trp Asn
    50                  55

<210> SEQ ID NO 6
<211> LENGTH: 91
<212> TYPE: PRT
<213> ORGANISM: Ruminococcus lactaris

<400> SEQUENCE: 6

Val Gly Trp Gly Ala Thr Ala Ser Asn Ala Trp Tyr Thr Val Leu Thr
1               5                   10                  15

Arg Asp Phe Ala Ala Gly Glu Tyr Val Trp Thr Gly Phe Asp Tyr Leu
            20                  25                  30

Gly Glu Pro Thr Pro Trp Asn Gly Thr Gly Ser Gly Ala Val Gly Ser
        35                  40                  45

Trp Pro Ser Pro Lys Asn Ser Tyr Phe Gly Ile Ile Asp Thr Ala Gly
    50                  55                  60

Phe Ala Lys Asp Ser Tyr Tyr Phe Tyr Gln Ser Gln Trp Asn Asp Asp
65                  70                  75                  80

Val Thr Thr Leu His Val Leu Pro Ala Trp Asn
                85                  90

<210> SEQ ID NO 7
<211> LENGTH: 71
<212> TYPE: PRT
<213> ORGANISM: Ruminococcus lactaris

<400> SEQUENCE: 7

```
Ala Gly Glu Tyr Val Trp Thr Gly Phe Asp Tyr Leu Gly Glu Pro Thr
1               5                   10                  15

Pro Trp Asn Gly Thr Gly Ser Gly Ala Val Gly Ser Trp Pro Ser Pro
            20                  25                  30

Lys Asn Ser Tyr Phe Gly Ile Ile Asp Thr Ala Gly Phe Ala Lys Asp
                35                  40                  45

Ser Tyr Tyr Phe Tyr Gln Ser Gln Trp Asn Asp Val Thr Thr Leu
    50                  55                  60

His Val Leu Pro Ala Trp Asn
65                  70

<210> SEQ ID NO 8
<211> LENGTH: 58
<212> TYPE: PRT
<213> ORGANISM: Ruminococcus lactaris

<400> SEQUENCE: 8

Ala Gly Glu Tyr Val Trp Thr Gly Phe Asp Tyr Leu Gly Glu Pro Thr
1               5                   10                  15

Pro Trp Asn Gly Thr Gly Ser Gly Ala Val Gly Ser Trp Pro Ser Pro
            20                  25                  30

Lys Asn Ser Tyr Phe Gly Ile Ile Asp Thr Ala Gly Phe Ala Lys Asp
                35                  40                  45

Ser Tyr Tyr Phe Tyr Gln Ser Gln Trp Asn
    50                  55

<210> SEQ ID NO 9
<211> LENGTH: 30
<212> TYPE: PRT
<213> ORGANISM: Bacillus subtilis

<400> SEQUENCE: 9

Val Arg Ser Lys Lys Leu Trp Ile Ser Leu Leu Phe Ala Leu Ala Leu
1               5                   10                  15

Ile Phe Thr Met Ala Phe Gly Ser Thr Ser Ser Ala Gln Ala
            20                  25                  30

<210> SEQ ID NO 10
<211> LENGTH: 3477
<212> TYPE: DNA
<213> ORGANISM: Ruminococcus hansenii

<400> SEQUENCE: 10
gtgagaagca aaaaattgtg gatcagtttg ctgtttgctt tagcgttaat ctttacgatg      60
gcgttcggca gcacatccag cgcgcaggcg gcagggaaaa aagcagatag ccaaacacaa     120
atgtcatcag aaccggaaca agttgcggtt aaagattatg gctcaaatag cgcacgcaca     180
cagaattttg atagcgattg gaaatttaac ctgggagatg ttagcaatgc acagacaccg     240
acatttgatg attcaaaatg gcgcacactg tcactgccgc atgattatag catcgaacag     300
gaatattcac atcactgga agcagaatca ggctatcttc cgggaggcgt tggctggtat     360
cgcaaaaatt ttacactggg cgaagaagcg aaaggcaaac gcattcgcat tgattttgat     420
ggcgtctata tgaatgcaac agtctatgtg aatggcaaag aagttggcac acatccgtat     480
ggctatacac cgtttagctt tgatatcaca gattatatca gctatgataa agaaaacaca     540
attgcggtca aagtcgatca tcaaacaccg tcatcaagat ggtattcagg cagcggcatt     600
tatagatcag tcaacctgac aacaacaaat gatgtccatg tcgatctgaa tggcattaaa     660
```

```
gtcgaaagca acaacctgga aaaagaagca ggcaaaacag tcaacacaga tgtgaaaaca    720
acagttgtga acggctcaaa agaagcgaaa aacatcacaa ttacacatac agtctttaaa    780
aaaggcgaaa aaccggataa agcgatcggc acatttacaa cagaagcgca agaaattggc    840
gcaggcaaaa aaacagaaat cagcgcaaca gtcccggtta aaaatccgga actgtggtca    900
gttgaaaatc cggcactgta tacaattcgc acagaagtta aagcaggcga taaactgctg    960
gatagctatg atacagaata tggctttcat tatctgaact ttgatacaga aacaggcttt    1020
cagctgaatg gcaaaaacgt taaactgaaa ggcgtttgca tgcatcatga tcaaggcgca    1080
cttggcgcag ttgcaaatag aagagcaatt gaacgccaag tcgaaattct gcaagaaatg    1140
ggctgcaata gcattagagt cacacataat ccggcaagca aagatctgat tgaagtctgc    1200
aacgaaaaag gcattctggt cattgaagaa gttttttgacg gctggcatag agcaaaaaat    1260
ggcaacagca acgattatag cgtctggttt gaaaaagcga tcgaagaaga taacgcgatt    1320 ctggggaaaag aagcggatat gacttgggca gaatatgatc tgaaagcgat tatgaaacgc    1380
gatcaaaatg caccgagcat tatttgaatgg tcactgggca atgaaattca agaaggcgca    1440
ggcggatcag gctatgcaga aagagcggat aaactgatca aatgggcgaa agaagcagac    1500
gcaacaaaaa cactgacaat tggcagcaat gcagttaaaa gaggcgattg gaacaagtt    1560 agcatcggcg ataaacttac aaaagcaggc ggaacatcag gcacaaatta ttcagatggc    1620
gcatcatatg ataaaattca taagaacat ccggattgga actgtatgg ctcagaaaca    1680 gcatcatcag ttaatagccg tggcatttat tcagttacag gcaatcaaga agcaacaagc    1740
gatcaacaac tgacagcgta tgataatagc agagttaatt ggggagcact ggcatcacaa    1800
gcatggtatg atgttatcca gagagatttt gtcgcaggcg aatatgtttg gacaggctttt    1860 gattatatcg gcgaaccgac accgtggaat ggcacagatc cggagcaaa aggcacatgg    1920 ccgtcaccga aaacagctac ctttggcatt atcgatacag caggctttcc gaaagattca    1980
tattattttt atcagagcca gtggaatgaa gaagtcaata cactgcacgt tcttccggca    2040
tggaatgaag atgtcgtcaa aaaaaactca gatggcacag ttccggttgt tgtttattca    2100
gatgcgaaag aagtcgaact gttttttaca ccggcaaatg gcggagaaaa aaaaagcctg    2160
ggaaaaaaaa catttaaaac agaaacaaca aaagctggct atagctatca agttctggaa    2220
aacggcaaaa aaaacataaa agatctgtat atggaatggc aagttccgta tgaagcaggc    2280
acacttgaag cagttgcgaa agatgcaaaa ggcaacgtca ttaaagatac agaaggcaga    2340
agcgtcgtta aaacaacagg cgaagaagca aaactgtcag caaaaacgga tcgcaatagc    2400
attcaagcag atggcaaaga tctgtcatat attacagtcg atgtcacaga taaagatggc    2460
aatattgttc cggatgcagc aaatagagtc acatttgatg tccaaggcgc aggaaaactg    2520
gttggcgttg ataatggctc atcaccggat catgatagct ataaagcgga taaccgcaaa    2580 gcatttttcag gcaaagttct ggcaattgtt cagtcaacag aaaaagcagg cgaaattaca    2640
gttacagcaa aagcagatgg cctggaatca agcacagtca aaatcacaac aacaccggtt    2700
aaagaagaac cgagcgaaag atatgtcgaa agctataaat acagcaaaag ctattatgtg    2760
aaaacaggca caaaaccgca actgccgaaa aaaattgaag cgcagtatag cgatcgcaca    2820
aaagaggatg ttgcggtcaa atgggatgaa atctcagatg aacaaattag caaaacaggc    2880
agctttacag ttgaaggcac agttggcaaa agagatatca cagtcaacat taacatgatc    2940
gatgatgttg cagcactgct gaattattca ggcgcaacac aaaaaggcgt taaaccgcaa    3000
cttccggatg ttagaccggc agttctgcct gatggcacag tcctggcagc atcatttccg    3060
```

```
gttcagtggg atgaaaaaga tgcggataca tttcagaaac cggatgaaat tgttacagtt   3120
aacggcagcg cagatatctt tggcaaaaca attccggtta cagcaagcat tagagtgcag   3180
aaagaagata tcaaaattgg cagcagcgtt acaaatgttg caaaactgag ccaaaatatt   3240
caaggcagcg atacactgga agcaatcaaa gatggcaaaa cagaaatgag cctgaataat   3300
gatggcggac cgaatgaatc agcatggtca aattgggatg catcacagaa aggcacaaaa   3360
gaagccgaac tgacatttac atttgataca cagcaacgca ttggcgaaat tgtcattcat   3420
tttgcgaaag ataacaactc aatcagattt ccggatgctg cacaacagaa atctaa       3477
```

<210> SEQ ID NO 11
<211> LENGTH: 3534
<212> TYPE: DNA
<213> ORGANISM: Ruminococcus lactaris

<400> SEQUENCE: 11

```
gtggatcagt tgctgtttg ctttagcgtt aatctttacg atggcgttcg gcagcacatc     60
cagcgcgcag gcggcaggga agcaggcgtt tcagttccgg cactggcaca caagcagtt    120 agaacagaaa gccaaacaca aatgtcatca gatccggaac tggtctatgt gaataactat   180
agcagcacag cacaaagaag ccagaacttt aacagcaact ggaaattcta cttcggagat   240
gcgggaaatg cacaaggcgc aacatttgat gatagcaaat gggaacaagt ttcactgccg   300
catgattatt caatcagcca agaatatagc aaatcaatgg aagcagaatc aggctatctt   360
ggcggaggca caggctggta tcgcaaaaat tttacactga gcagcgatac acaaggcaaa   420
agagtccgca ttgattttga tggcgtctat atgaatgcaa cagtttgggt taatggccat   480
gaagttggca cacatccgta tggctataca agctttagct tgatatcac agattatgtg    540 aaatatgatg gcgaaaacac aattgcagtc aaagtcgtca ataatacacc gtcaagcaga   600
tggtattcag gctcaggcat ttatagagat gtcgatctga caatcacaga tgatgttcat   660
gttgatctga acggcacaaa agttacaaca ccgaacctgg aaacagaaaa aggcagcaca   720
gtcaatacag atgttacagc aacagttgcg aatgattcag atgcagcaaa atcagttgca   780
gttcgccata cagttttttcc gaaagatggc agcgcagatc aatcaattgg cacagtcaca   840
acaaatgcac aatcaattgc agcaggcgca acagcagaaa ttcaagcaac ggttccggtt   900
tcaaatcctg aactgtggtc agttgaaaat ccgtcactgt atacagtcag aacagaagtt   960
ctggtcgacg gccaagtcac agatacatat gatacagaat atggctttcg ctattttaac  1020
tttgatagca acacaggctt ttcactgaat ggcgaaaata tgaaactgaa aggcgtctgc  1080
atgcatcatg atcaaggctc acttggcgca gcagcatacg actcagcaat tgatcgccag  1140
gtcaaaatcc tgaaagaaat gggctgcaat agcattagag tcacacataa tccggcagca  1200
caagatctga ttgatgcgtg caatgaacaa ggcattctgg ttgttgaaga agcgtttgat  1260
acttggacaa gaccgaaaaa tggcaacagc aacgattata cgtctggtt taatcagaca   1320 gttgcgagcg ataatgaaat tctgggagcg acaaatggcg aaacatgggc acaatttgat  1380
ctggaaagca tgatctcacg cgattataat gcaccgtcag tcattatgtg gtcactgggc  1440
aatgaagtta tggaaggcat tagcggaggc acagatgcag aatatgaagc gacagcgacg  1500
aaactgatta actgggcgta tgatgcggat aatacacgtc cgatgacaat tggcgataac  1560
aaactgaaag cgaactggca gatctcaaaa acatttgcga gactgctgac agaaaaaggc  1620
ggaacagtgg gctttaatta tgcagatggc agagttctgg attcatatca tagcagcaat  1680
```

| | |
|---|---|
| agcaattggc tgctgtatgg ctcagaaaca gcatcagcga ttaatagccg tggcatctat | 1740 |
| tatagaacaa caggcggagg ccaaacatca gataaacagc tgacaagcta tgataattca | 1800 |
| aatgttggct ggggagcaac agcatcaaat gcatggtata cagttctgac aagagatttt | 1860 |
| gcggcaggcg aatatgtttg gacaggcttt gattatctgg gcgaaccgac accgtggaat | 1920 |
| ggcacaggct caggcgcagt tggctcatgg ccgtcaccga aaaattctta ttttggcatt | 1980 |
| atcgatacag caggcttcgc aaaagatagc tattattttt atcagagcca gtggaatgat | 2040 |
| gatgttacaa cactgcatgt tcttccggca tggaataata atgtcgtcag caaagattca | 2100 |
| tcaggcaatg ttccggttgt tgtttattca gatgcggcat cagtcgaact gttttttcaa | 2160 |
| gcaaaaggca gcgatacaaa acaagcctg gcaaaaaaa catttacaca gaaaacaaca | 2220 |
| gacgcaggct atacatatca gatctatgaa ggctcagata aaaacagcac aacagacaaa | 2280 |
| aacctgtatc tgacatggaa tgttccgtat gcagatggaa cagtttcagc agttgcgtat | 2340 |
| aatagcaacg gccagaaaat tacagataca gttggccagt cctcagttac aacaacaggc | 2400 |
| aaagcgtcaa aactgaaagc atcagcggat cataaaaaaa ttgcagcgga tggcgaatca | 2460 |
| ctgtcatata tcacagtcga tgtcacagat gcgaatggca atattgttcc ggatgcagaa | 2520 |
| aatcgcgtca aatttacagt tgaaggcgat ggcgaactgg ttggcgttga taatggctca | 2580 |
| tcaccggatc atgattcata tcaagcggat aaccgcaaag cattttcagg caaagttctg | 2640 |
| gcaattgtga aaagcacaaa agaagctggc acaattacag ttacagcatc agcagatggc | 2700 |
| ctggattcag catcagtcaa aatcacaaca acagcagtcg ataatggcag cacagaaaaa | 2760 |
| caaatcgata gctttaaaat gagccgcaca tattatgtta agttggcag cacaccggaa | 2820 |
| ctgccggaaa aaattgtcac acgctataca gatggcacat cagaagaact gcctgttact | 2880 |
| tgggatgcaa ttacagaaga tcaaattgca gcagcaggct catttcaagt aaaggcaca | 2940 |
| gtcaaaggcg atattcagt tgcagtcaac gtcaacatga ttgatgaagt tggcggactg | 3000 |
| ctgaattatt caacaaatac agcagttggc gttgcaccgg ttctgccgac atcaagaccg | 3060 |
| gcagttctgc aagatggcac agttatggat gttacatttc cggtcacatg gaagataaa | 3120 |
| gcagcaagcg catatgataa agcaggcaca gtgacagtca tggcacagc aaatgttctg | 3180 |
| ggcaaagaaa ttgcagttac agcgagcgtt agagttcagg aagaaacaat cacaattgga | 3240 |
| gattcagttt cagcggatgc actgaatctg cacaaaagcg ttccggcaga taaacaaagc | 3300 |
| gatacactga acgcaattaa agatggctca caacaattag gctcaaatac aagcggaggc | 3360 |
| gcaaatccga cagtttggag caactatgac tatagccagg atggcaatac gacagcggat | 3420 |
| atcatttttg aatatgcgac agaacaaaga ctgggccaaa tcgttacaca ttttgcgaga | 3480 |
| gatagctggt caatgagata tcctgatgca ggcgctacag aaatttatgt ctaa | 3534 |

<210> SEQ ID NO 12
<211> LENGTH: 1807
<212> TYPE: PRT
<213> ORGANISM: Ruminococcus hansenii

<400> SEQUENCE: 12

Met Tyr Phe Phe Gly Arg Ser Ala Ile Met Met Leu Thr Val Lys Thr
1               5                   10                  15

Arg Lys Glu Ile Phe Met Arg Lys Gln Arg Leu Ala Arg Ile Gly Ala
            20                  25                  30

Ala Thr Leu Ala Ala Val Leu Thr Val Gln Gly Met Gly Phe Ser Ser
        35                  40                  45

```
Thr Val Tyr Ala Lys Glu Glu Pro Val Arg Val Lys Ala Asp Ser Gln
    50              55                  60

Thr Gln Met Ser Ser Glu Pro Glu Gln Val Ala Val Lys Asp Tyr Gly
65          70                  75                  80

Ser Asn Ser Ala Arg Thr Gln Asn Phe Asp Ser Asp Trp Lys Phe Asn
                85              90                  95

Leu Gly Asp Val Ser Asn Ala Gln Thr Pro Thr Phe Asp Asp Ser Lys
            100             105                 110

Trp Arg Thr Leu Ser Leu Pro His Asp Tyr Ser Ile Glu Gln Glu Tyr
            115             120                 125

Ser Gln Ser Leu Glu Ala Glu Ser Gly Tyr Leu Pro Gly Val Gly
    130             135                 140

Trp Tyr Arg Lys Asn Phe Thr Leu Gly Glu Glu Ala Lys Gly Lys Arg
145             150              155                 160

Ile Arg Ile Asp Phe Asp Gly Val Tyr Met Asn Ala Thr Val Tyr Val
                165             170                 175

Asn Gly Lys Glu Val Gly Thr His Pro Tyr Gly Tyr Thr Pro Phe Ser
            180             185                 190

Phe Asp Ile Thr Asp Tyr Ile Ser Tyr Asp Lys Glu Asn Thr Ile Ala
            195             200                 205

Val Lys Val Asp His Gln Thr Pro Ser Ser Arg Trp Tyr Ser Gly Ser
    210             215                 220

Gly Ile Tyr Arg Ser Val Asn Leu Thr Thr Thr Asn Asp Val His Val
225             230             235                 240

Asp Leu Asn Gly Ile Lys Val Glu Ser Asn Asn Leu Glu Lys Glu Ala
                245             250                 255

Gly Lys Thr Val Asn Thr Asp Val Lys Thr Thr Val Val Asn Gly Ser
            260             265                 270

Lys Glu Ala Lys Asn Ile Thr Ile Thr His Thr Val Phe Lys Lys Gly
    275             280                 285

Glu Lys Pro Asp Lys Ala Ile Gly Thr Phe Thr Thr Glu Ala Gln Glu
    290             295                 300

Ile Gly Ala Gly Lys Lys Thr Glu Ile Ser Ala Thr Val Pro Val Lys
305             310             315                 320

Asn Pro Glu Leu Trp Ser Val Glu Asn Pro Ala Leu Tyr Thr Ile Arg
            325             330                 335

Thr Glu Val Lys Ala Gly Asp Lys Leu Leu Asp Ser Tyr Asp Thr Glu
            340             345                 350

Tyr Gly Phe His Tyr Leu Asn Phe Asp Thr Glu Thr Gly Phe Gln Leu
            355             360                 365

Asn Gly Lys Asn Val Lys Leu Lys Gly Val Cys Met His His Asp Gln
    370             375                 380

Gly Ala Leu Gly Ala Val Ala Asn Arg Arg Ala Ile Glu Arg Gln Val
385             390             395                 400

Glu Ile Leu Gln Glu Met Gly Cys Asn Ser Ile Arg Val Thr His Asn
                405             410                 415

Pro Ala Ser Lys Asp Leu Ile Glu Val Cys Asn Glu Lys Gly Ile Leu
            420             425                 430

Val Ile Glu Glu Val Phe Asp Gly Trp His Arg Ala Lys Asn Gly Asn
            435             440                 445

Ser Asn Asp Tyr Ser Val Trp Phe Glu Lys Ala Ile Glu Glu Asp Asn
    450             455                 460

Ala Ile Leu Gly Lys Glu Ala Asp Met Thr Trp Ala Glu Tyr Asp Leu
```

```
              465                 470                 475                 480
Lys Ala Ile Met Lys Arg Asp Gln Asn Ala Pro Ser Ile Ile Glu Trp
                    485                 490                 495

Ser Leu Gly Asn Glu Ile Gln Glu Gly Ala Gly Ser Gly Tyr Ala
                500                 505                 510

Glu Arg Ala Asp Lys Leu Ile Lys Trp Ala Lys Glu Ala Asp Ala Thr
                515                 520                 525

Lys Thr Leu Thr Ile Gly Ser Asn Ala Val Lys Arg Gly Asp Trp Glu
530                 535                 540

Gln Val Ser Ile Gly Asp Lys Leu Thr Lys Ala Gly Gly Thr Ser Gly
545                 550                 555                 560

Thr Asn Tyr Ser Asp Gly Ala Ser Tyr Asp Lys Ile His Lys Glu His
                565                 570                 575

Pro Asp Trp Lys Leu Tyr Gly Ser Glu Thr Ala Ser Ser Val Asn Ser
                580                 585                 590

Arg Gly Ile Tyr Ser Val Thr Gly Asn Gln Glu Ala Thr Ser Asp Gln
                595                 600                 605

Gln Leu Thr Ala Tyr Asp Asn Ser Arg Val Asn Trp Gly Ala Leu Ala
                610                 615                 620

Ser Gln Ala Trp Tyr Asp Val Ile Gln Arg Asp Phe Val Ala Gly Glu
625                 630                 635                 640

Tyr Val Trp Thr Gly Phe Asp Tyr Ile Gly Glu Pro Thr Pro Trp Asn
                645                 650                 655

Gly Thr Asp Pro Gly Ala Lys Gly Thr Trp Pro Ser Pro Lys Asn Ser
                660                 665                 670

Tyr Phe Gly Ile Ile Asp Thr Ala Gly Phe Pro Lys Asp Ser Tyr Tyr
                675                 680                 685

Phe Tyr Gln Ser Gln Trp Asn Glu Glu Val Asn Thr Leu His Val Leu
                690                 695                 700

Pro Ala Trp Asn Glu Asp Val Val Lys Lys Asn Ser Asp Gly Thr Val
705                 710                 715                 720

Pro Val Val Val Tyr Ser Asp Ala Lys Glu Val Glu Leu Phe Phe Thr
                725                 730                 735

Pro Ala Asn Gly Gly Glu Lys Lys Ser Leu Gly Lys Lys Thr Phe Lys
                740                 745                 750

Thr Glu Thr Thr Lys Ala Gly Tyr Ser Tyr Gln Val Leu Glu Asn Gly
                755                 760                 765

Lys Lys Lys His Lys Asp Leu Tyr Met Glu Trp Gln Val Pro Tyr Glu
770                 775                 780

Ala Gly Thr Leu Glu Ala Val Ala Lys Asp Ala Lys Gly Asn Val Ile
785                 790                 795                 800

Lys Asp Thr Glu Gly Arg Ser Val Val Lys Thr Thr Gly Glu Glu Ala
                805                 810                 815

Lys Leu Ser Ala Lys Thr Asp Arg Asn Ser Ile Gln Ala Asp Gly Lys
                820                 825                 830

Asp Leu Ser Tyr Ile Thr Val Asp Val Thr Asp Lys Asp Gly Asn Ile
                835                 840                 845

Val Pro Asp Ala Ala Asn Arg Val Thr Phe Asp Val Gln Gly Ala Gly
                850                 855                 860

Lys Leu Val Gly Val Asp Asn Gly Ser Ser Pro Asp His Asp Ser Tyr
865                 870                 875                 880

Lys Ala Asp Asn Arg Lys Ala Phe Ser Gly Lys Val Leu Ala Ile Val
                885                 890                 895
```

-continued

Gln Ser Thr Glu Lys Ala Gly Glu Ile Thr Val Thr Ala Lys Ala Asp
        900                 905                 910

Gly Leu Glu Ser Ser Thr Val Lys Ile Thr Thr Thr Pro Val Lys Glu
        915                 920                 925

Glu Pro Ser Glu Arg Tyr Val Glu Ser Tyr Lys Tyr Ser Lys Ser Tyr
        930                 935                 940

Tyr Val Lys Thr Gly Thr Lys Pro Gln Leu Pro Lys Lys Ile Glu Ala
945                 950                 955                 960

Gln Tyr Ser Asp Arg Thr Lys Glu Asp Val Ala Val Lys Trp Asp Glu
                965                 970                 975

Ile Ser Asp Glu Gln Ile Ser Lys Thr Gly Ser Phe Thr Val Glu Gly
        980                 985                 990

Thr Val Gly Lys Arg Asp Ile Thr Val Asn Ile Asn Met Ile Asp Asp
        995                 1000                1005

Val Ala Ala Leu Leu Asn Tyr Ser Gly Ala Thr Gln Lys Gly Val
        1010                1015                1020

Lys Pro Gln Leu Pro Asp Val Arg Pro Ala Val Leu Pro Asp Gly
        1025                1030                1035

Thr Val Leu Ala Ala Ser Phe Pro Val Gln Trp Asp Glu Lys Asp
        1040                1045                1050

Ala Asp Thr Phe Gln Lys Pro Asp Glu Ile Val Thr Val Asn Gly
        1055                1060                1065

Ser Ala Asp Ile Phe Gly Lys Thr Ile Pro Val Thr Ala Ser Ile
        1070                1075                1080

Arg Val Gln Lys Glu Asp Ile Lys Ile Gly Ser Ser Val Thr Asn
        1085                1090                1095

Val Ala Lys Leu Ser Gln Asn Ile Gln Gly Ser Asp Thr Leu Glu
        1100                1105                1110

Ala Ile Lys Asp Gly Lys Thr Glu Met Ser Leu Asn Asn Asp Gly
        1115                1120                1125

Gly Pro Asn Glu Ser Ala Trp Ser Asn Trp Asp Ala Ser Gln Lys
        1130                1135                1140

Gly Thr Lys Glu Ala Glu Leu Thr Phe Thr Phe Asp Thr Gln Gln
        1145                1150                1155

Arg Ile Gly Glu Ile Val Ile His Phe Ala Lys Asp Asn Asn Ser
        1160                1165                1170

Ile Arg Phe Pro Asp Ala Gly Thr Thr Glu Ile Phe Val Ser Glu
        1175                1180                1185

Thr Gly Lys Asp Gly Thr Trp Glu Lys Val Glu Val Lys Glu His
        1190                1195                1200

Ile Gly Glu Glu Lys Asp Arg Val Lys Ala Tyr Arg Tyr Glu Ile
        1205                1210                1215

Ala Pro Val Thr Ala Thr Tyr Val Lys Val Lys Val Val Asn Ala
        1220                1225                1230

Asn Ala Thr Asp Thr Gly Asn Arg Lys Pro Cys Thr Ala Ile Thr
        1235                1240                1245

Glu Val Glu Leu Lys Lys Ala Glu Gly Ser Phe Lys Val Asn Glu
        1250                1255                1260

Thr Ala Glu Leu Glu Glu Val Lys Val Gly Glu Arg Val Leu Pro
        1265                1270                1275

Asn Ala Ala Tyr Ala Leu Asp Ser Tyr Ser Val Pro Glu Thr Asp
        1280                1285                1290

```
Ala Ala Val Thr Ala Lys Thr Lys Asp Asn Ala Ser Leu Thr Ile
1295                1300                1305

Leu Pro Lys His Glu Asn Val Val Arg Met Ile Leu Glu Ser Glu
1310                1315                1320

Asp His Lys Ala Thr Lys Asn Phe Ala Val Arg Met Gly Glu Glu
1325                1330                1335

Glu Thr Val Leu Pro Asp Asp Ser Arg Asp Tyr Pro Val Glu
1340                1345                1350

Lys Ile Thr Ala Thr Ala Gly Ser Glu Tyr Lys Pro Gly Thr Ala
1355                1360                1365

Asn Glu Gly Pro Val Lys Tyr Val Leu Asp Gly Lys Ala Glu Thr
1370                1375                1380

His Trp His Thr Asn Trp Ser Val Ser Gly Glu Gly Ser Lys Pro
1385                1390                1395

Glu His Arg Thr Val Thr Leu Gln Leu Gly Asn Asp Glu Glu Glu
1400                1405                1410

Ala Pro Met Ile Asp Ala Leu Arg Tyr Met Pro Arg Ser Asn Gly
1415                1420                1425

Ala Asn Gly Arg Val Thr Glu Tyr Glu Ile Gln Tyr Ser Leu Asp
1430                1435                1440

Gly Asp Lys Trp Gln Thr Ala Ala Thr Gly Glu Ile Asp Lys Lys
1445                1450                1455

Gln Thr Gly Trp Met Ile Leu Gly Phe Glu Glu Pro Val Gln Ala
1460                1465                1470

Lys Tyr Val Arg Phe Ile Gly Thr His Thr Thr Ser Asp Gln Gly
1475                1480                1485

Asn Asp Lys His Met Ala Val Ser Glu Leu Arg Ala Arg Val Ala
1490                1495                1500

Thr Glu Ala Pro Ala Pro Ser Glu Lys Tyr Thr Ile Thr Ala Asn
1505                1510                1515

Val Asn Asp Lys Thr Met Gly Ala Val Thr Leu Asp Ser Glu Thr
1520                1525                1530

Gly Glu Tyr Glu Lys Gly Thr Lys Ala Thr Leu Thr Ala Val Pro
1535                1540                1545

Lys Glu Gly Phe Ala Phe Val Asn Trp Thr Ile Asp Gly Gln Glu
1550                1555                1560

Val Ser Lys Glu Asn Pro Tyr Ile His Thr Val Glu Thr Asp Ala
1565                1570                1575

Thr Ile Thr Ala Asn Phe Glu Arg Ile Glu Val Glu Asn Glu Gly
1580                1585                1590

Trp Val Gln Thr Glu Asn Gly Trp Glu Tyr Tyr Glu Asn Gly Gln
1595                1600                1605

Lys Val Val Gly Trp Lys Glu Val Ser Gly Lys Trp Tyr Tyr Phe
1610                1615                1620

Glu Glu Asn Gly Leu Met Gln Thr Gly Trp Val Phe Val Asn Asn
1625                1630                1635

His Trp Tyr Tyr Met Asp Gln Trp Gly Ala Met Cys Ile Gly Trp
1640                1645                1650

Val Ala Val Asp Gly His Trp Tyr Tyr Met Asp Gln Trp Gly Ala
1655                1660                1665

Met Cys Thr Gly Trp Val Ser Val Asn Gly His Trp Tyr His Met
1670                1675                1680

Asp Gln Trp Gly Ala Met Gln Thr Gly Trp Ala Leu Val Asp Ser
```

-continued

```
            1685                1690                1695

Asn Trp Tyr Tyr Leu Asn Thr Asp Gly Ser Met Ala Ile Gly Trp
            1700                1705                1710

Val Ala Val Asn Gly His Trp Tyr Tyr Met Asp Gln Trp Gly Ala
            1715                1720                1725

Met Gln Thr Gly Trp Ala Leu Val Asp Ser Asn Trp Tyr Tyr Leu
            1730                1735                1740

Asn Thr Asp Gly Ser Met Ala Ile Gly Trp Val Ala Val Asn Gly
            1745                1750                1755

His Trp Tyr Tyr Met Asp Gln Trp Gly Ala Met Gln Thr Gly Trp
            1760                1765                1770

Val Leu Val Gly Ser Asp Trp Tyr Tyr Leu Asn Thr Asp Gly Ser
            1775                1780                1785

Met Ala Ser Ser Gln Trp Ile Asp Gly Tyr Tyr Val Asp Ala Ser
            1790                1795                1800

Gly Lys Met Lys
            1805

<210> SEQ ID NO 13
<211> LENGTH: 1768
<212> TYPE: PRT
<213> ORGANISM: Ruminococcus lactaris

<400> SEQUENCE: 13

Met Lys Lys Lys Lys Arg Cys Thr Arg Val Gly Ala Gly Ala Leu Ala
1               5                   10                  15

Ala Val Leu Ala Val Thr Ala Ala Gly Val Ser Val Pro Ala Leu Ala
                20                  25                  30

Gln Gln Ala Val Arg Thr Glu Ser Gln Thr Gln Met Ser Ser Asp Pro
            35                  40                  45

Glu Leu Val Tyr Val Asn Asn Tyr Ser Ser Thr Ala Gln Arg Ser Gln
        50                  55                  60

Asn Phe Asn Ser Asn Trp Lys Phe Tyr Phe Gly Asp Ala Gly Asn Ala
65                  70                  75                  80

Gln Gly Ala Thr Phe Asp Asp Ser Lys Trp Glu Gln Val Ser Leu Pro
                85                  90                  95

His Asp Tyr Ser Ile Ser Gln Glu Tyr Ser Lys Ser Met Glu Ala Glu
            100                 105                 110

Ser Gly Tyr Leu Gly Gly Gly Thr Gly Trp Tyr Arg Lys Asn Phe Thr
        115                 120                 125

Leu Ser Ser Asp Thr Gln Gly Lys Arg Val Arg Ile Asp Phe Asp Gly
130                 135                 140

Val Tyr Met Asn Ala Thr Val Trp Val Asn Gly His Glu Val Gly Thr
145                 150                 155                 160

His Pro Tyr Gly Tyr Thr Ser Phe Ser Phe Asp Ile Thr Asp Tyr Val
                165                 170                 175

Lys Tyr Asp Gly Glu Asn Thr Ile Ala Val Lys Val Asn Asn Thr
            180                 185                 190

Pro Ser Ser Arg Trp Tyr Ser Gly Ser Ile Tyr Arg Asp Val Asp
        195                 200                 205

Leu Thr Ile Thr Asp Asp Val His Val Asp Leu Asn Gly Thr Lys Val
210                 215                 220

Thr Thr Pro Asn Leu Glu Thr Glu Lys Gly Ser Thr Val Asn Thr Asp
225                 230                 235                 240
```

Val Thr Ala Thr Val Ala Asn Asp Ser Asp Ala Ala Lys Ser Val Ala
                245                 250                 255

Val Arg His Thr Val Phe Pro Lys Asp Gly Ala Asp Gln Ser Ile
        260                 265                 270

Gly Thr Val Thr Thr Asn Ala Gln Ser Ile Ala Ala Gly Ala Thr Ala
            275                 280                 285

Glu Ile Gln Ala Thr Val Pro Val Ser Asn Pro Glu Leu Trp Ser Val
290                 295                 300

Glu Asn Pro Ser Leu Tyr Thr Val Arg Thr Glu Val Leu Val Asp Gly
305                 310                 315                 320

Gln Val Thr Asp Thr Tyr Asp Thr Glu Tyr Gly Phe Arg Tyr Phe Asn
                325                 330                 335

Phe Asp Ser Asn Thr Gly Phe Ser Leu Asn Gly Glu Asn Met Lys Leu
            340                 345                 350

Lys Gly Val Cys Met His His Asp Gln Gly Ser Leu Gly Ala Ala Ala
        355                 360                 365

Tyr Asp Ser Ala Ile Asp Arg Gln Val Lys Ile Leu Lys Glu Met Gly
    370                 375                 380

Cys Asn Ser Ile Arg Val Thr His Asn Pro Ala Ala Gln Asp Leu Ile
385                 390                 395                 400

Asp Ala Cys Asn Glu Gln Gly Ile Leu Val Val Glu Glu Ala Phe Asp
                405                 410                 415

Thr Trp Thr Arg Pro Lys Asn Gly Asn Ser Asn Asp Tyr Ser Val Trp
            420                 425                 430

Phe Asn Gln Thr Val Ala Ser Asp Asn Glu Ile Leu Gly Ala Thr Asn
        435                 440                 445

Gly Glu Thr Trp Ala Gln Phe Asp Leu Glu Ser Met Ile Ser Arg Asp
    450                 455                 460

Tyr Asn Ala Pro Ser Val Ile Met Trp Ser Leu Gly Asn Glu Val Met
465                 470                 475                 480

Glu Gly Ile Ser Gly Gly Thr Asp Ala Glu Tyr Glu Ala Thr Ala Thr
                485                 490                 495

Lys Leu Ile Asn Trp Ala Tyr Asp Ala Asp Asn Thr Arg Pro Met Thr
            500                 505                 510

Ile Gly Asp Asn Lys Leu Lys Ala Asn Trp Gln Ile Ser Lys Thr Phe
        515                 520                 525

Ala Arg Leu Leu Thr Glu Lys Gly Gly Thr Val Gly Phe Asn Tyr Ala
    530                 535                 540

Asp Gly Arg Val Leu Asp Ser Tyr His Ser Ser Asn Ser Asn Trp Leu
545                 550                 555                 560

Leu Tyr Gly Ser Glu Thr Ala Ser Ala Ile Asn Ser Arg Gly Ile Tyr
                565                 570                 575

Tyr Arg Thr Thr Gly Gly Gln Thr Ser Asp Lys Gln Leu Thr Ser
            580                 585                 590

Tyr Asp Asn Ser Asn Val Gly Trp Gly Ala Thr Ala Ser Asn Ala Trp
        595                 600                 605

Tyr Thr Val Leu Thr Arg Asp Phe Ala Ala Gly Glu Tyr Val Trp Thr
    610                 615                 620

Gly Phe Asp Tyr Leu Gly Glu Pro Thr Pro Trp Asn Gly Thr Gly Ser
625                 630                 635                 640

Gly Ala Val Gly Ser Trp Pro Ser Pro Lys Asn Ser Tyr Phe Gly Ile
                645                 650                 655

Ile Asp Thr Ala Gly Phe Ala Lys Asp Ser Tyr Tyr Phe Tyr Gln Ser

```
                660             665             670
Gln Trp Asn Asp Asp Val Thr Thr Leu His Val Leu Pro Ala Trp Asn
            675             680             685
Asn Asn Val Val Ser Lys Asp Ser Ser Gly Asn Val Pro Val Val
        690             695             700
Tyr Ser Asp Ala Ala Ser Val Glu Leu Phe Phe Gln Ala Lys Gly Ser
705             710             715             720
Asp Thr Lys Thr Ser Leu Gly Lys Lys Thr Phe Thr Gln Lys Thr Thr
                725             730             735
Asp Ala Gly Tyr Thr Tyr Gln Ile Tyr Glu Gly Ser Asp Lys Asn Ser
            740             745             750
Thr Thr Asp Lys Asn Leu Tyr Leu Thr Trp Asn Val Pro Tyr Ala Asp
        755             760             765
Gly Thr Val Ser Ala Val Ala Tyr Asn Ser Asn Gly Lys Ile Thr
        770             775             780
Asp Thr Val Gly Gln Ser Ser Val Thr Thr Gly Lys Ala Ser Lys
785             790             795             800
Leu Lys Ala Ser Ala Asp His Lys Lys Ile Ala Ala Asp Gly Glu Ser
            805             810             815
Leu Ser Tyr Ile Thr Val Asp Val Thr Asp Ala Asn Gly Asn Ile Val
            820             825             830
Pro Asp Ala Glu Asn Arg Val Lys Phe Thr Val Glu Gly Asp Gly Glu
            835             840             845
Leu Val Gly Val Asp Asn Gly Ser Ser Pro Asp His Asp Ser Tyr Gln
850             855             860
Ala Asp Asn Arg Lys Ala Phe Ser Gly Lys Val Leu Ala Ile Val Lys
865             870             875             880
Ser Thr Lys Glu Ala Gly Thr Ile Thr Val Thr Ala Ser Ala Asp Gly
                885             890             895
Leu Asp Ser Ala Ser Val Lys Ile Thr Thr Thr Ala Val Asp Asn Gly
            900             905             910
Ser Thr Glu Lys Gln Ile Asp Ser Phe Lys Met Ser Arg Thr Tyr Tyr
            915             920             925
Val Lys Val Gly Ser Thr Pro Glu Leu Pro Glu Lys Ile Val Thr Arg
            930             935             940
Tyr Thr Asp Gly Thr Ser Glu Glu Leu Pro Val Thr Trp Asp Ala Ile
945             950             955             960
Thr Glu Asp Gln Ile Ala Ala Ala Gly Ser Phe Gln Val Lys Gly Thr
            965             970             975
Val Lys Gly Gly Tyr Ser Val Ala Val Asn Val Asn Met Ile Asp Glu
        980             985             990
Val Gly Gly Leu Leu Asn Tyr Ser  Thr Asn Thr Ala Val  Gly Val Ala
            995            1000            1005
Pro Val  Leu Pro Thr Ser Arg  Pro Ala Val Leu Gln  Asp Gly Thr
        1010            1015            1020
Val Met  Asp Val Thr Phe Pro  Val Thr Trp Glu Asp   Lys Ala Ala
        1025            1030            1035
Ser Ala  Tyr Asp Lys Ala Gly  Thr Val Thr Val Asn  Gly Thr Ala
        1040            1045            1050
Asn Val  Leu Gly Lys Glu Ile  Ala Val Thr Ala Ser  Val Arg Val
        1055            1060            1065
Gln Glu  Glu Thr Ile Thr Ile  Gly Asp Ser Val Ser  Ala Asp Ala
        1070            1075            1080
```

-continued

```
Leu Asn Leu Thr Gln Ser Val Pro Ala Asp Lys Gln Ser Asp Thr
    1085            1090                1095

Leu Asn Ala Ile Lys Asp Gly Ser Thr Thr Ile Ser Ser Asn Thr
    1100            1105                1110

Ser Gly Gly Ala Asn Pro Thr Val Trp Ser Asn Tyr Asp Tyr Ser
    1115            1120                1125

Gln Asp Gly Asn Thr Thr Ala Asp Ile Ile Phe Glu Tyr Ala Thr
    1130            1135                1140

Glu Gln Arg Leu Gly Gln Ile Val Thr His Phe Ala Arg Asp Ser
    1145            1150                1155

Trp Ser Met Arg Tyr Pro Asp Ala Gly Ala Thr Glu Ile Tyr Val
    1160            1165                1170

Ser Pro Asp Gly Thr Asn Trp Ala Lys Leu Asp Thr Thr Glu Thr
    1175            1180                1185

Ile Gly Thr Glu Ser Gly Asn Val Lys Pro Tyr Thr Tyr Asp Phe
    1190            1195                1200

Ala Pro Val Gly Ala Thr Phe Val Lys Phe His Leu Thr Asn Ser
    1205            1210                1215

Thr Gln Ala Thr Gly Thr Thr Ala Lys Ala Cys Thr Gly Ile Thr
    1220            1225                1230

Glu Ile Glu Leu Lys Val Ala Thr Gly Ser Arg Thr Thr Asn Thr
    1235            1240                1245

Thr Ala Glu Leu Gln Thr Leu Thr Val Asn Gly Lys Glu Val Pro
    1250            1255                1260

Gln Thr Ala Leu Asp Ser Lys Val Tyr Thr Thr Pro Ala Ile Leu
    1265            1270                1275

Ala Glu Ile Glu Ala Thr Ala Lys Asp Asn Ala Ser Val Thr Val
    1280            1285                1290

Leu Pro Ala Tyr Asn Asp Val Ile Arg Ile Ile Val Glu Ser Glu
    1295            1300                1305

Asp His Gln Thr Arg Asn Thr Tyr Glu Val Arg Leu Asn Glu Ala
    1310            1315                1320

Glu Gln Thr Thr Pro Asp Ser Asp Ser Arg Asp Tyr Pro Val Ser
    1325            1330                1335

Lys Leu Thr Ala Ser Ala Gly Ser Glu Gln Ser Thr Thr Gly Val
    1340            1345                1350

Glu Gly Pro Ala Ser Asn Ala Lys Asp Gly Asp Glu Ser Thr Leu
    1355            1360                1365

Trp His Thr Arg Trp Ser Ala Pro Ala Ala Thr Ser Asp Gln Leu
    1370            1375                1380

Trp Phe Thr Tyr Glu Leu Glu Glu Thr Val Leu Asp Ala Leu
    1385            1390                1395

Arg Tyr Leu Pro Arg Gln Gly Thr Ala Asp Gly Gln Asn Asn Gly
    1400            1405                1410

Arg Val Asn Glu Tyr Arg Val Glu Val Ser Thr Asp Gly Ser Thr
    1415            1420                1425

Trp Thr Thr Val Ser Thr Gly Asn Trp Glu Asp Ser Gln Asp Trp
    1430            1435                1440

Lys Leu Ala Glu Phe Thr Glu Pro Val Ala Ala Lys Tyr Val Arg
    1445            1450                1455

Leu Thr Gly Val His Thr Tyr Gly Ser Ser Ala Ala Asn Val Asp
    1460            1465                1470
```

| | | | | | | | | | |
|---|---|---|---|---|---|---|---|---|---|
| Lys | Tyr | Met | Ser | Ala | Ala | Glu | Ile | Arg | Leu | Arg | Met | Ala | Glu | Ser |
| 1475 | | | | | 1480 | | | | | 1485 | | | | |

Lys Tyr Met Ser Ala Ala Glu Ile Arg Leu Arg Met Ala Glu Ser
    1475                1480                1485

Lys Thr Asp Ile Ala Asp Ala Ala Asn Gly Val Thr Val Thr Ala
    1490                1495                1500

Pro Asp Ser Ile Glu Val Ala Lys Ala Asp Ala Glu Asn Pro Val
    1505                1510                1515

Met Phe Asp Leu Ser Asp Ile Val Val Lys Ala Gly Asp Thr Thr
    1520                1525                1530

Leu Arg Tyr Gly Val Asp Tyr Val Ile Ser Tyr Glu Asn Asn Thr
    1535                1540                1545

Asp Phe Gly Thr Ala Lys Leu Val Ile Lys Gly Ile Asp Gly Tyr
    1550                1555                1560

Thr Gly Thr Leu Glu His Glu Phe Thr Ile Thr Gln Lys Ala Lys
    1565                1570                1575

Val Met Thr Gly Ile Thr Trp Asn Thr Lys Pro Glu Lys Val Ile
    1580                1585                1590

Tyr Thr Glu Gly Glu Thr Leu Asp Val Thr Gly Leu Val Ile Asn
    1595                1600                1605

Val Val Tyr Asp Asp Asp Ser Thr Glu Ala Val Ala Tyr Ser Glu
    1610                1615                1620

Ala Asn Ala Asp Glu Phe Thr Phe Ser Pro Ala Leu Asp Thr Lys
    1625                1630                1635

Leu Ala Ala Thr Asp Lys Thr Val Thr Val Thr Tyr Lys Gly Ala
    1640                1645                1650

Ser Leu Ile Tyr Asp Ile Thr Val Asn Pro Lys Lys Val Asp Pro
    1655                1660                1665

Thr Asp Pro Asp Gln Pro Asp Lys Pro Asp Thr Pro Asp Asn Gly
    1670                1675                1680

Asn Asp Asn Gly Asn Asp Asn Asn Gly Asn Gly Asn Asn Asn Gly
    1685                1690                1695

Thr Asp Asp Gly Lys Lys Asp Pro Gly Gln Ser Gly Val Thr Asp
    1700                1705                1710

Asn Lys Asn Gln Gly Asn Asn Ser Asn Asn Gly Thr Ala Ala Gly
    1715                1720                1725

Asn Lys Ala Asn Ala Ala Lys Thr Gly Asp Thr Ala Asn Met
    1730                1735                1740

Leu Leu Pro Met Ile Ala Ala Met Leu Ala Gly Thr Ala Val Val
    1745                1750                1755

Gly Thr Ile Ser Ile Arg Arg Arg Arg Arg
    1760                1765

<210> SEQ ID NO 14
<211> LENGTH: 5244
<212> TYPE: DNA
<213> ORGANISM: Ruminococcus hansenii

<400> SEQUENCE: 14
aaagcagata gccaaacaca aatgtcatca gaaccggaac aagttgcggt taaagattat      60
ggctcaaata gcgcacgcac acagaatttt gatagcgatt ggaaatttaa cctgggagat     120
gttagcaatg cacagacacc gacatttgat gattcaaaat ggcgcacact gtcactgccg     180
catgattata gcatcgaaca ggaatattca caatcactgg aagcagaatc aggctatctt     240
ccgggaggcg ttggctggta tcgcaaaaat tttacactgg gcgaagaagc gaaaggcaaa     300
cgcattcgca ttgattttga tggcgtctat atgaatgcaa cagtctatgt gaatggcaaa     360

```
gaagttggca cacatccgta tggctataca ccgtttagct ttgatatcac agattatatc    420
agctatgata aagaaaacac aattgcggtc aaagtcgatc atcaaacacc gtcatcaaga    480
tggtattcag gcagcggcat ttatagatca gtcaacctga caacaacaaa tgatgtccat    540
gtcgatctga atggcattaa agtcgaaagc aacaacctgg aaaaagaagc aggcaaaaca    600
gtcaacacag atgtgaaaac aacagttgtg aacggctcaa agaagcgaaa aacatcaca    660 attacacata cagtctttaa aaaaggcgaa aaaccggata aagcgatcgg cacatttaca    720
acagaagcgc aagaaattgg cgcaggcaaa aaaacagaaa tcagcgcaac agtcccggtt    780
aaaaatccgg aactgtggtc agttgaaaat ccggcactgt atacaattcg cacagaagtt    840
aaagcaggcg ataaactgct ggatagctat gatacagaat atggctttca ttatctgaac    900
tttgatacag aaacaggctt tcagctgaat ggcaaaaacg ttaaactgaa aggcgtttgc    960
atgcatcatg atcaaggcgc acttggcgca gttgcaaata aagagcaat tgaacgccaa    1020 gtcgaaattc tgcaagaaat gggctgcaat agcattagag tcacacataa tccggcaagc    1080
aaagatctga ttgaagtctg caacgaaaaa ggcattctgg tcattgaaga agttttttgac    1140 ggctggcata gagcaaaaaa tggcaacagc aacgattata cgtctggtt tgaaaaagcg    1200 atcgaagaag ataacgcgat tctgggaaaa gaagcggata tgacttgggc agaatatgat    1260
ctgaaagcga ttatgaaacg cgatcaaaat gcaccgagca ttattgaatg gtcactgggc    1320
aatgaaattc aagaaggcgc aggcggatca ggctatgcag aaagagcgga taaactgatc    1380
aaatgggcga agaagcaga cgcaacaaaa acactgacaa ttggcagcaa tgcagttaaa    1440
agaggcgatt gggaacaagt tagcatcggc gataaactta caaaagcagg cggaacatca    1500
ggcacaaatt attcagatgg cgcatcatat gataaaattc ataaagaaca tccggattgg    1560
aaactgtatg gctcagaaac agcatcatca gttaatagcc gtggcattta ttcagttaca    1620
ggcaatcaag aagcaacaag cgatcaacaa ctgacagcgt atgataatag cagagttaat    1680
tggggagcac tggcatcaca agcatggtat gatgttatcc agagagattt tgtcgcaggc    1740
gaatatgttt ggacaggctt tgattatatc ggcgaaccga caccgtggaa tggcacagat    1800
ccgggagcaa aaggcacatg gccgtcaccg aaaaacagct actttggcat tatcgataca    1860
gcaggctttc cgaaagattc atattatttt tatcagagcc agtggaatga agaagtcaat    1920
acactgcacg ttcttccggc atggaatgaa gatgtcgtca aaaaaaactc agatggcaca    1980
gttccggttg ttgtttattc agatgcgaaa gaagtcgaac tgttttttac accggcaaat    2040
ggcggagaaa aaaaagcct gggaaaaaaa acatttaaaa cagaaacaac aaaagctggc    2100
tatagctatc aagttctgga aaacggcaaa aaaaaacata agatctgta tatggaatgg    2160 caagttccgt atgaagcagg cacacttgaa gcagttgcga agatgcaaa aggcaacgtc    2220 attaaagata cagaaggcag aagcgtcgtt aaaacaacag gcgaagaagc aaaactgtca    2280
gcaaaaacgg atcgcaatag cattcaagca gatggcaaag atctgtcata tattacagtc    2340
gatgtcacag ataaagatgg caatattgtt ccggatgcag caaatagagt cacatttgat    2400
gtccaaggcg caggaaaact ggttggcgtt gataatggct catcaccgga tcatgatagc    2460
tataaagcgg ataaccgcaa agcattttca ggcaaagttc tggcaattgt tcagtcaaca    2520
gaaaaagcag gcgaaattac agttacagca aaagcagatg gcctggaatc aagcacagtc    2580
aaaatcacaa caacaccggt taagaagaa ccgagcgaaa gatatgtcga aagctataaa    2640
tacagcaaaa gctattatgt gaaaacaggc acaaaaccgc aactgccgaa aaaaattgaa    2700
```

```
gcgcagtata gcgatcgcac aaaagaggat gttgcggtca aatgggatga aatctcagat    2760
gaacaaatta gcaaaacagg cagctttaca gttgaaggca cagttggcaa aagagatatc    2820
acagtcaaca ttaacatgat cgatgatgtt gcagcactgc tgaattattc aggcgcaaca    2880
caaaaaggcg ttaaaccgca acttccggat gttagaccgg cagttctgcc tgatggcaca    2940
gtcctggcag catcatttcc ggttcagtgg gatgaaaaag atgcggatac atttcagaaa    3000
ccggatgaaa ttgttacagt taacggcagc gcagatatct ttggcaaaac aattccggtt    3060
acagcaagca ttagagtgca gaaagaagat atcaaaattg cagcagcgt tacaaatgtt     3120 gcaaaactga gccaaaatat tcaaggcagc gatacactgg aagcaatcaa agatggcaaa    3180
acagaaatga gcctgaataa tgatggcgga ccgaatgaat cagcatggtc aaattgggat    3240
gcatcacaga aaggcacaaa agaagccgaa ctgacattta catttgatac acagcaacgc    3300
attggcgaaa ttgtcattca ttttgcgaaa gataacaact caatcagatt tccggatgct    3360
ggcacaacag aaatctttgt ttcagaaaca ggcaaagatg gcacatggga aaaagttgaa    3420
gtcaaagagc atattggcga gaaaaagat cgcgtcaaag catatcgcta tgaaattgca     3480
ccggttacag cgacatatgt taaagttaaa gtcgtcaatg cgaacgcgac agatacaggc    3540
aatagaaaac cgtgcacagc aattacgaaa gtcgaactga aaaagcaga aggcagcttt     3600 aaagtcaacg aaacagcaga actggaagaa gttaaagttg cgaacgtgt tctgccgaat     3660 gcagcatatg cactggattc atattcagtt ccggaaacgg atgcagcagt tacagcaaaa    3720
acaaaagata tgcgagcct gacaatcctg ccgaaacatg aaaatgtcgt cagaatgatt     3780
ctggaaagcg aagaccataa agcgacgaaa aactttgcag ttagaatggg cgaagaagaa    3840
acagttctgc cggatgatga ttcaagagat tatccggtcg aaaaaatcac agcaacagca    3900
ggctcagaat ataaaccggg aacagcaaat gaaggaccgg ttaaatatgt tctggatggc    3960
aaagcagaaa cacattggca tacaaattgg tcagtttcag gcgaaggctc aaaaccggaa    4020
catagaacag ttacactgca actgggcaat gatgaagaag aagcaccgat gattgacgca    4080
ctgagatata tgccgagatc aaatggcgca atggcagag ttacggaata tgaaattcag     4140
tatagcctgg atggcgataa atggcaaaca gcagcaacag gcgaaatcga taaaaaacaa    4200
acaggctgga tgatcctggg cttttgaagaa ccggttcaag caaaatatgt ccgctttatt    4260
ggcacacata caacatcaga tcagggcaat gataaacata tggcagtttc agaactgaga    4320
gcaagagttg caacagaagc accggcaccg tcagagaagt atacaattac agcgaacgtc    4380
aacgataaaa caatgggagc agttacactt gatagcgaaa caggcgaata tgaaaaaggc    4440
acgaaagcaa cactgacagc agttccgaaa gaaggctttg catttgtcaa ctggacaatt    4500
gatggccaag aagtctcaaa agaaaacccg tatatccata cagttgaaac ggatgcgaca    4560
atcacagcga attttgaacg cattgaagtc gaaaatgaag gctggttca acagaaaat      4620 ggctgggaat attatgagaa tggccaaaaa gttgtcggct ggaaagaagt ttcaggcaaa    4680
tggtactact ttgaagaaaa tggcctgatg caaacaggat gggtctttgt taacaaccat    4740
tggtattata tggatcagtg gggggcaatg tgcattggct gggttgcagt tgatggccat    4800
tggtactaca tggaccaatg gggtgctatg tgtacaggct gggttagcgt caatggacat    4860
tggtatcata tggaccaatg gggagccatg caaacaggct gggcactggt tgattcaaat    4920
tggtattacc tgaatacgga tggctcaatg gcaattggat gggtcgcagt gaacggccac    4980
tggtattaca tggatcaatg gggagctatg cagacgggat gggctcttgt tgatagcaac    5040
tggtattatc ttaacacaga tggcagcatg gcaatcggct gggtggcggt taatggacac    5100
```

```
tggtactata tggatcaatg gggtgcaatg cagacaggct gggttctggt cggcagcgat    5160
tggtactatt taaacacgga tggatctatg gcatcaagcc aatggattga tggctattat    5220
gttgatgcaa gcggcaagat gaag                                           5244

<210> SEQ ID NO 15
<211> LENGTH: 5235
<212> TYPE: DNA
<213> ORGANISM: Ruminococcus lactaris

<400> SEQUENCE: 15
gcaggcgttt cagttccggc actggcacaa caagcagtta aacagaaag ccaaacacaa       60 atgtcatcag atccggaact ggtctatgtg aataactata gcagcacagc acaagaagc      120 cagaacttta acagcaactg gaaattctac ttcggagatg cgggaaatgc acaaggcgca     180
acatttgatg atagcaaatg gaacaagtt tcactgccgc atgattattc aatcagccaa      240
gaatatagca atcaatggaa gcagaatca ggctatcttg cggaggcac aggctggtat       300 cgcaaaaatt ttacactgag cagcgataca caaggcaaaa gagtccgcat tgatttttgat   360 ggcgtctata tgaatgcaac agtttgggtt aatggccatg aagttggcac acatccgtat    420
ggctatacaa gctttagctt tgatatcaca gattatgtga aatatgatgg cgaaaacaca    480
attgcagtca aagtcgtcaa taatacaccg tcaagcagat ggtattcagg ctcaggcatt    540
tatagagatg tcgatctgac aatcacagat gatgttcatg ttgatctgaa cggcacaaaa    600
gttacaacac cgaacctgga aacagaaaaa ggcagcacag tcaatacaga tgttacagca    660
acagttgcga atgattcaga tgcagcaaaa tcagttgcag ttcgccatac agttttttccg   720 aaagatggca gcgcagatca atcaattggc acagtcacaa caaatgcaca atcaattgca    780
gcaggcgcaa cagcagaaat tcaagcaacg gttccggttt caaatcctga actgtggtca    840
gttgaaaatc gtcactgta tacagtcaga acagaagttc tggtcgacgg ccaagtcaca     900
gatacatatg atacagaata tggctttcgc tattttaact ttgatagcaa cacaggctttt   960 tcactgaatg gcgaaaaatat gaaactgaaa ggcgtctgca tgcatcatga tcaaggctca   1020
cttggcgcag cagcatacga ctcagcaatt gatcgccagg tcaaaatcct gaaagaaatg    1080
ggctgcaata gcattagagt cacacataat ccggcagcac aagatctgat tgatgcgtgc    1140
aatgaacaag gcattctggt tgttgaagaa gcgtttgata cttggacaag accgaaaaat    1200
ggcaacagca acgattatag cgtctggttt aatcagacag ttgcgagcga taatgaaatt    1260
ctgggagcga caaatggcga aacatgggca caatttgatc tggaaagcat gatctcacgc    1320
gattataatg caccgtcagt cattatgtgg tcactgggca atgaagttat ggaaggcatt    1380
agcggaggca cagatgcaga atatgaagcg acagcgacga aactgattaa ctgggcgtat    1440
gatgcggata tacacgtcc gatgacaatt ggcgataaca aactgaaagc gaactggcag    1500
atctcaaaaa catttgcgag actgctgaca gaaaaaggcg aacagtggg ctttaattat    1560 gcagatggca gagttctgga ttcatatcat agcagcaata gcaattggct gctgtatggc    1620
tcagaaacag catcagcgat taatagccgt ggcatctatt atagaacaac aggcggaggc    1680
caaacatcag ataaacagct gacaagctat gataattcaa atgttggctg gggagcaaca    1740
gcatcaaatg catggtatac agttctgaca agagattttg cggcaggcga atatgtttgg    1800
acaggctttg attatctggg cgaaccgaca ccgtggaatg cacaggctc aggcgcagtt    1860 ggctcatggc cgtcaccgaa aaattcttat tttggcatta tcgatacagc aggcttcgca   1920
```

```
aaagatagct attattttta tcagagccag tggaatgatg atgttacaac actgcatgtt   1980
cttccggcat ggaataataa tgtcgtcagc aaagattcat caggcaatgt tccggttgtt   2040
gtttattcag atgcggcatc agtcgaactg ttttttcaag caaaaggcag cgatacaaaa   2100
acaagcctgg gcaaaaaaac atttacacag aaaacaacag acgcaggcta tacatatcag   2160
atctatgaag gctcagataa aaacagcaca acagacaaaa acctgtatct gacatggaat   2220
gttccgtatg cagatggaac agtttcagca gttgcgtata atagcaacgg ccagaaaatt   2280
acagatacag ttggccagtc ctcagttaca acaacaggca aagcgtcaaa actgaaagca   2340
tcagcggatc ataaaaaaat tgcagcggat ggcgaatcac tgtcatatat cacagtcgat   2400
gtcacagatg cgaatggcaa tattgttccg gatgcagaaa atcgcgtcaa atttacagtt   2460
gaaggcgatg cgaactggt tggcgttgat aatggctcat caccggatca tgattcatat   2520
caagcggata accgcaaagc atttccaggc aaagttctgg caattgtgaa aagcacaaaa   2580
gaagctggca caattacagt tacagcatca gcagatggcc tggattcagc atcagtcaaa   2640
atcacaacaa cagcagtcga taatggcagc acagaaaaac aaatcgatag ctttaaaatg   2700
agccgcacat attatgttaa agttggcagc acaccggaac tgccggaaaa aattgtcaca   2760
cgctatacag atggcacatc agaagaactg cctgttactt gggatgcaat tacagaagat   2820
caaattgcag cagcaggctc atttcaagtt aaaggcacag tcaaaggcgg atattcagtt   2880
gcagtcaacg tcaacatgat tgatgaagtt ggcggactgc tgaattattc aacaaataca   2940
gcagttggcg ttgcaccggt tctgccgaca tcaagaccgg cagttctgca agatggcaca   3000
gttatggatg ttacatttcc ggtcacatgg aagataaag cagcaagcgc atatgataaa   3060
gcaggcacag tgacagtcaa tggcacagca atgttctgg gcaaagaaat tgcagttaca   3120
gcgagcgtta gagttcagga agaaacaatc acaattggag attcagtttc agcggatgca   3180
ctgaatctga cacaaagcgt tccggcagat aaacaaagcg atacactgaa cgcaattaaa   3240
gatggctcaa caacaattag ctcaaataca agcggaggcg caaatccgac agtttggagc   3300
aactatgact atagccagga tggcaatacg acagcggata tcattttga atatgcgaca   3360 gaacaaagac tgggccaaat cgttacacat tttgcgagag atagctggtc aatgagatat   3420
cctgatgcag gcgctacaga aatttatgtc tcaccggatg cacaaattg ggcaaaactg   3480 gatacaacag aaacaattgg cacagaaagc ggcaatgtta accgtatac atatgatttt   3540 gcaccggttg gcgcaacatt tgttaaattt catctgacaa acagcacaca agcaacaggc   3600
acaacagcaa aagcatgcac aggcattaca gaaattgaac tgaaagttgc aacaggctca   3660
cgcacaacaa atacaacagc agaactgcaa acactgacag ttaatggcaa agaagttccg   3720
caaacagcac tggatagcaa agtttataca acaccggcaa ttctggcaga aattgaagca   3780
acagcgaaag ataatgcaag cgttacagtt cttccggcat ataatgatgt cattcgcatt   3840
attgtcgaaa gcgaagatca tcaaacacgc aatacatatg aagtcagact gaatgaagcg   3900
gaacaaacaa caccggattc agattcaaga gattatccgg ttagcaaact gacagcatca   3960
gcaggctcag aacaatcaac aacaggcgtt gaaggaccgg catcaaatgc aaaagacggt   4020
gatgaatcaa cactgtggca tacaagatgg tcagcaccgg cagcaacatc agatcaactg   4080
tggtttacat atgaactgga agaagaaacg gtactggacg cactgagata tctgccgaga   4140
caaggcacag cagatggcca aaataatggc agagttaatg aatatcgcgt cgaagttagc   4200
acagatggca gcacatggac aacagttttca acaggcaatt gggaagatag ccaagattgg   4260
aaactggcag aatttacaga accggttgca gcaaaatatg tcagactgac aggcgttcat   4320
```

```
acatatggct catcagcagc aaacgtcgat aaatacatga gcgcagcaga aattagactg    4380
agaatggcag aaagcaaaac ggatattgca gatgcagcaa atggcgttac agttacagca    4440
ccggattcaa ttgaagttgc aaaagcagat gcagaaaacc cggttatgtt tgatctgagc    4500
gatattgttg tcaaagcagg cgatacaaca ctgagatatg cgttgatta tgtcattagc     4560 tatgaaaaca acacagattt tggcacagcg aaactggtca ttaaaggcat tgatggctat    4620
acaggcacac tggaacatga attcacaatc acgcagaaag ccaaagtcat gacaggcatc    4680
acatggaata caaaaccgga aaaagtcatt tatacggaag gtgaaacgct ggatgttaca    4740
ggcctggtta ttaatgtcgt ctatgatgat gatagcacag aagcagttgc atatagcgaa    4800
gcaaatgcgg atgaatttac attttcaccg gcactggata caaaactggc agcgacagat    4860
aaaacagtca cagttacata taaggcgcaa agcctgattt atgatattac agtcaacccg    4920
aaaaaagtcg atccgacaga tccggatcag cctgataaac cggatacacc ggataatggc    4980
aatgataacg gcaacgataa taatggcaac ggcaataaca acggcacaga tgatggcaaa    5040
aaagatccgg gacaatcagg cgttacagat aacaaaaatc agggcaataa cagcaataat    5100
ggaacagcag caggcaataa agcaaatgca gcagcaaaaa caggcgatac agcaaatatg    5160
ctgctgccga tgattgcagc aatgctggca ggcacagcag ttgttggcac aatttcaatt    5220
cgcagacgca gacgc                                                    5235

<210> SEQ ID NO 16
<211> LENGTH: 3375
<212> TYPE: DNA
<213> ORGANISM: Ruminococcus hansenii

<400> SEQUENCE: 16
aaagcagata gccaaacaca aatgtcatca gaaccggaac aagttgcggt taaagattat     60
ggctcaaata gcgcacgcac acagaatttt gatagcgatt ggaaatttaa cctgggagat    120
gttagcaatg cacagacacc gacatttgat gattcaaaat ggcgcacact gtcactgccg    180
catgattata gcatcgaaca ggaatattca caatcactgg aagcagaatc aggctatctt    240
ccgggaggcg ttggctggta tcgcaaaaat tttacactgg gcgaagaagc gaaaggcaaa    300
cgcattcgca ttgattttga tggcgtctat atgaatgcaa cagtctatgt gaatggcaaa    360
gaagttgcac acatccgta tggctataca ccgtttagct ttgatatcac agattatatc    420
agctatgata agaaaaacac aattgcggtc aaagtcgatc atcaaacacc gtcatcaaga    480
tggtattcag gcagcggcat ttatagatca gtcaacctga caacaacaaa tgatgtccat    540
gtcgatctga atggcattaa agtcgaaagc aacaacctgg aaaaagaagc aggcaaaaca    600
gtcaacacag atgtgaaaac aacagttgtg aacggctcaa agaagcgaa aaacatcaca    660 attacacata cagtctttaa aaaaggcgaa aaaccggata agcgatcgg cacatttaca    720 acagaagcgc aagaaattgg cgcaggcaaa aaaacagaaa tcagcgcaac agtcccggtt    780
aaaaatccgg aactgtggtc agttgaaaat ccggcactgt atacaattcg cacagaagtt    840
aaagcaggcg ataaactgct ggatagctat gatacagaat atggctttca ttatctgaac    900
tttgatacag aaacaggctt tcagctgaat ggcaaaaacg ttaaactgaa aggcgtttgc    960
atgcatcatg atcaaggcgc acttggcgca gttgcaaata aagagcaat tgaacgccaa     1020 gtcgaaattc tgcaagaaat gggctgcaat agcattagag tcacacataa tccggcaagc    1080
aaagatctga ttgaagtctg caacgaaaaa ggcattctgg tcattgaaga gttttttgac    1140
```

```
ggctggcata gagcaaaaaa tggcaacagc aacgattata gcgtctggtt tgaaaaagcg    1200
atcgaagaag ataacgcgat tctgggaaaa gaagcggata tgacttgggc agaatatgat    1260
ctgaaagcga ttatgaaacg cgatcaaaat gcaccgagca ttattgaatg gtcactgggc    1320
aatgaaattc aagaaggcgc aggcggatca ggctatgcag aaagagcgga taaactgatc    1380
aaatgggcga agaagcaga cgcaacaaaa acactgacaa ttggcagcaa tgcagttaaa    1440
agaggcgatt gggaacaagt tagcatcggc gataaactta caaaagcagg cggaacatca    1500
ggcacaaatt attcagatgg cgcatcatat gataaaattc ataaagaaca tccggattgg    1560
aaactgtatg gctcagaaac agcatcatca gttaatagcc gtggcattta ttcagttaca    1620
ggcaatcaag aagcaacaag cgatcaacaa ctgacagcgt atgataatag cagagttaat    1680
tggggagcac tggcatcaca agcatggtat gatgttatcc agagagattt tgtcgcaggc    1740
gaatatgttt ggacaggctt tgattatatc ggcgaaccga caccgtggaa tggcacagat    1800 ccggagcaa aaggcacatg gccgtcaccg aaaaacagct actttggcat tatcgataca    1860
gcaggctttc cgaaagattc atattatttt tatcagagcc agtggaatga agaagtcaat    1920
acactgcacg ttcttccggc atggaatgaa gatgtcgtca aaaaaaactc agatggcaca    1980
gttccggttg ttgtttattc agatgcgaaa gaagtcgaac tgtttttac accggcaaat    2040 ggcggagaaa aaaaagcct gggaaaaaaa acatttaaaa cagaaacaac aaaagctggc    2100
tatagctatc aagttctgga aacggcaaa aaaaacata aagatctgta tatggaatgg    2160
caagttccgt atgaagcagg cacacttgaa gcagttgcga agatgcaaa aggcaacgtc    2220 attaaagata cagaaggcag aagcgtcgtt aaaacaacag cgaagaagc aaaactgtca    2280 gcaaaaacgg atcgcaatag cattcaagca gatggcaaag atctgtcata tattacagtc    2340
gatgtcacag ataaagatgg caatattgtt ccggatgcag caaatagagt cacatttgat    2400
gtccaaggcg caggaaaact ggttggcgtt gataatggct catcaccgga tcatgatagc    2460
tataaagcgg ataaccgcaa agcatttttca ggcaaagttc tggcaattgt tcagtcaaca    2520
gaaaaagcag gcgaaattac agttacagca aaagcagatg gcctggaatc aagcacagtc    2580
aaaatcacaa caacaccggt taagaagaa ccgagcgaaa gatatgtcga agctataaaa    2640
tacagcaaaa gctattatgt gaaaacaggc acaaaccgc aactgccgaa aaaaattgaa    2700
gcgcagtata gcgatcgcac aaaagaggat gttgcggtca aatgggatga aatctcagat    2760
gaacaaatta gcaaaacagg cagctttaca gttgaaggca cagttggcaa aagagatatc    2820
acagtcaaca ttaacatgat cgatgatgtt gcagcactgc tgaattattc aggcgcaaca    2880
caaaaaggcg ttaaaccgca acttccggat gttagaccgg cagttctgcc tgatggcaca    2940
gtcctggcag catcatttcc ggttcagtgg gatgaaaaag atgcggatac atttcagaaa    3000
ccggatgaaa ttgttacagt taacggcagc gcagatatct ttggcaaaac aattccggtt    3060
acagcaagca ttagagtgca gaaagaagat atcaaaattg gcagcagcgt tacaaatgtt    3120
gcaaaactga gccaaaatat tcaaggcagc gatacactgg aagcaatcaa agatggcaaa    3180
acagaaatga gcctgaataa tgatggcgga ccgaatgaat cagcatggtc aaattgggat    3240
gcatcacaga aaggcacaaa agaagccgaa ctgacattta catttgatac acagcaacgc    3300
attggcgaaa ttgtcattca ttttgcgaaa gataacaact caatcagatt tccggatgct    3360
ggcacaacag aaatc                                                    3375

<210> SEQ ID NO 17
<211> LENGTH: 3450
```

<212> TYPE: DNA
<213> ORGANISM: Ruminococcus lactaris

<400> SEQUENCE: 17

```
gcaggcgttt cagttccggc actggcacaa caagcagtta gaacagaaag ccaaacacaa      60
atgtcatcag atccggaact ggtctatgtg aataactata gcagcacagc acaaagaagc     120
cagaacttta acagcaactg gaaattctac ttcggagatg cgggaaatgc acaaggcgca     180
acatttgatg atagcaaatg ggaacaagtt tcactgccgc atgattattc aatcagccaa     240
gaatatagca aatcaatgga agcagaatca ggctatcttg gcggaggcac aggctggtat     300
cgcaaaaatt ttacactgag cagcgataca caaggcaaaa gagtccgcat tgattttgat     360
ggcgtctata tgaatgcaac agtttgggtt aatggccatg aagttggcac acatccgtat     420
ggctatacaa gctttagctt tgatatcaca gattatgtga aatatgatgg cgaaaacaca     480
attgcagtca agtcgtcaa taatacaccg tcaagcagat ggtattcagg ctcaggcatt     540
tatagagatg tcgatctgac aatcacagat gatgttcatg ttgatctgaa cggcacaaaa     600
gttacaacac cgaacctgga aacagaaaaa ggcagcacag tcaatacaga tgttacagca     660
acagttgcga atgattcaga tgcagcaaaa tcagttgcag ttcgccatac agttttttccg     720
aaagatggca gcgcagatca atcaattggc acagtcacaa caaatgcaca atcaattgca     780
gcaggcgcaa cagcagaaat tcaagcaacg gttccggttt caaatcctga actgtggtca     840
gttgaaaatc cgtcactgta tacagtcaga acagaagttc tggtcgacgg ccaagtcaca     900
gatacatatg atacagaata tggctttcgc tattttaact ttgatagcaa cacaggcttt     960
tcactgaatg gcgaaaatat gaaactgaaa ggcgtctgca tgcatcatga tcaaggctca    1020
cttggcgcag cagcatacga ctcagcaatt gatcgccagg tcaaaatcct gaaagaaatg    1080
ggctgcaata gcattagagt cacacataat ccggcagcac aagatctgat tgatgcgtgc    1140
aatgaacaag gcattctggt tgttgaagaa gcgtttgata cttggacaag accgaaaaat    1200
ggcaacagca acgattatag cgtctggttt aatcagacag ttgcgagcga taatgaaatt    1260
ctgggagcga caaatggcga acatgggca caatttgatc tggaaagcat gatctcacgc    1320
gattataatg caccgtcagt cattatgtgg tcactgggca atgaagttat ggaaggcatt    1380
agcggaggca cagatgcaga atatgaagcg acagcgacga aactgattaa ctgggcgtat    1440
gatgcggata atacacgtcc gatgacaatt ggcgataaca aactgaaagc gaactggcag    1500
atctcaaaaa catttgcgag actgctgaca gaaaaaggcg gaacagtggg ctttaattat    1560
gcagatggca gagttctgga ttcatatcat agcagcaata gcaattggct gctgtatggc    1620
tcagaaacag catcagcgat taatagccgt ggcatctatt atagaacaac aggcggaggc    1680
caaacatcag ataaacagct gacaagctat gataattcaa atgttggctg gggagcaaca    1740
gcatcaaatg catggtatac agttctgaca agagattttg cggcaggcga atatgtttgg    1800
acaggctttg attatctggg cgaaccgaca ccgtggaatg cacaggctc aggcgcagtt    1860
ggctcatggc cgtcaccgaa aaattcttat tttggcatta tcgatacagc aggcttcgca    1920
aaagatagct attattttta tcagagccag tggaatgatg atgttacaac actgcatgtt    1980
cttccggcat ggaataataa tgtcgtcagc aaagattcat caggcaatgt tccggttgtt    2040
gtttattcag atgcggcatc agtcgaactg ttttttcaag caaaaggcag cgatacaaaa    2100
acaagcctgg gcaaaaaaac atttacacag aaaacaacag acgcaggcta tacatatcag    2160
atctatgaag gctcagataa aaacagcaca acagacaaaa acctgtatct gacatggaat    2220
```

```
gttccgtatg cagatggaac agtttcagca gttgcgtata atagcaacgg ccagaaaatt    2280
acagatacag ttggccagtc ctcagttaca acaacaggca aagcgtcaaa actgaaagca    2340
tcagcggatc ataaaaaaat tgcagcggat ggcgaatcac tgtcatatat cacagtcgat    2400
gtcacagatg cgaatggcaa tattgttccg gatgcagaaa atcgcgtcaa atttacagtt    2460
gaaggcgatg gcgaactggt tggcgttgat aatggctcat caccggatca tgattcatat    2520
caagcggata accgcaaagc attttcaggc aaagttctgg caattgtgaa agcacaaaa     2580 gaagctggca caattacagt tacagcatca gcagatggcc tggattcagc atcagtcaaa    2640
atcacaacaa cagcagtcga taatggcagc acagaaaaac aaatcgatag ctttaaaatg    2700
agccgcacat attatgttaa agttggcagc acaccggaac tgccggaaaa aattgtcaca    2760
cgctatacag atggcacatc agaagaactg cctgttactt gggatgcaat tacagaagat    2820
caaattgcag cagcaggctc atttcaagtt aaaggcacag tcaaaggcgg atattcagtt    2880
gcagtcaacg tcaacatgat tgatgaagtt ggcggactgc tgaattattc aacaaataca    2940
gcagttggcg ttgcaccggt tctgccgaca tcaagaccgg cagttctgca agatggcaca    3000
gttatggatg ttacatttcc ggtcacatgg gaagataaag cagcaagcgc atatgataaa    3060
gcaggcacag tgacagtcaa tggcacagca aatgttctgg gcaaagaaat tgcagttaca    3120
gcgagcgtta gagttcagga agaaacaatc acaattggag attcagtttc agcggatgca    3180
ctgaatctga cacaaagcgt tccggcagat aaacaaagcg atacactgaa cgcaattaaa    3240
gatggctcaa caacaattag ctcaaataca agcggaggcg caaatccgac agtttggagc    3300
aactatgact atagccagga tggcaatacg acagcggata tcattttga atatgcgaca     3360 gaacaaagac tgggccaaat cgttacacat tttgcgagag atagctggtc aatgagatat    3420
cctgatgcag gcgctacaga aatttatgtc                                    3450
```